(12) United States Patent
Milliman et al.

(10) Patent No.: US 7,438,718 B2
(45) Date of Patent: Oct. 21, 2008

(54) ANASTOMOSIS INSTRUMENT AND METHOD FOR PERFORMING SAME

(75) Inventors: Keith Milliman, Bethel, CT (US); Kevin Sniffen, Danbury, CT (US); Joseph P Orban, III, Norwalk, CT (US); Lisa W. Heaton, Shelton, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 665 days.

(21) Appl. No.: 10/480,964

(22) PCT Filed: Jan. 8, 2002

(86) PCT No.: PCT/US02/00345

§ 371 (c)(1), (2), (4) Date: Dec. 10, 2003

(87) PCT Pub. No.: WO02/058568

PCT Pub. Date: Aug. 1, 2002

(65) Prior Publication Data

US 2004/0199182 A1    Oct. 7, 2004

Related U.S. Application Data

(60) Provisional application No. 60/263,891, filed on Jan. 24, 2001.

(51) Int. Cl.
- A61B 17/10 (2006.01)
- A61B 17/08 (2006.01)
- A61B 17/04 (2006.01)

(52) U.S. Cl. ............... 606/142; 606/153; 227/175.1

(58) Field of Classification Search ............ 606/139, 606/142, 219, 104, 116, 117; 227/175.1, 227/176.1, 178.1, 179.1, 180.1, 153
See application file for complete search history.

(56) References Cited

U.S. PATENT DOCUMENTS

| 3,080,564 A | * | 3/1963 | Strekopitov et al. | ......... 227/153 |
| 3,232,089 A | | 2/1966 | Samuels et al. | |
| 3,366,301 A | | 1/1968 | Mallina | |
| 3,519,187 A | | 7/1970 | Kapitanov et al. | |
| 3,955,581 A | * | 5/1976 | Spasiano et al. | ......... 227/175.1 |
| 4,166,466 A | | 9/1979 | Jarvik | |

(Continued)

FOREIGN PATENT DOCUMENTS

EP    384647 A1    2/1990

(Continued)

OTHER PUBLICATIONS

International Search Report—EPO 0120262.
International Search Report—EPO 97112634.
International Search Report—EPO 98110977.
International Search Report—EPO 99118064.
International Search Report—PCT/US01/02043.
International Search Report PCT/US02/00345.
Information Booklet for: LIGACLIP, Ligating Clips, Appliers & Removers For security in Ligation, Ethicon, Inc., 1982.

(Continued)

*Primary Examiner*—Julian W Woo

(57) ABSTRACT

A surgical instrument for anastomosis of first and second blood vessels includes a housing having distal and proximal ends and an actuator disposed therebetween. The actuator includes a handle and a link assembly, the link assembly being movable through a firing stroke in response to movement of the handle. The instrument also includes a disposable loading unit releasably attached to the distal end of the housing in mechanical cooperation with the actuator. The disposable loading unit supports a plurality of surgical fasteners, which deform upon movement of the actuator and the link assembly through the firing stroke.

12 Claims, 42 Drawing Sheets

U.S. PATENT DOCUMENTS

| | | | |
|---|---|---|---|
| 4,350,160 | A | 9/1982 | Kolesov et al. |
| 4,368,736 | A | 1/1983 | Kaster |
| D276,650 | S | 12/1984 | Green et al. |
| 4,872,874 | A | 10/1989 | Taheri |
| 4,930,674 | A | 6/1990 | Barak |
| 4,979,954 | A | 12/1990 | Gwathmey et al. |
| 5,025,779 | A | 6/1991 | Bugge |
| 5,188,638 | A | 2/1993 | Tzakis |
| 5,211,649 | A | 5/1993 | Kohler et al. |
| 5,222,963 | A | 6/1993 | Brinkerhoff et al. |
| 5,234,447 | A | 8/1993 | Kaster et al. |
| 5,282,810 | A | 2/1994 | Allen et al. |
| 5,314,436 | A | 5/1994 | Wilk |
| 5,346,501 | A | 9/1994 | Regula et al. |
| 5,354,304 | A | 10/1994 | Allen et al. |
| 5,366,462 | A | 11/1994 | Kaster et al. |
| 5,403,333 | A | 4/1995 | Kaster et al. |
| 5,403,338 | A | 4/1995 | Milo |
| 5,425,738 | A | 6/1995 | Gustafson et al. |
| 5,431,668 | A | 7/1995 | Burbank, III et al. |
| 5,437,684 | A | 8/1995 | Calabrese et al. |
| 5,443,198 | A | 8/1995 | Viola et al. |
| 5,452,733 | A | 9/1995 | Sterman et al. |
| 5,454,824 | A | 10/1995 | Fontayne et al. |
| 5,467,911 | A * | 11/1995 | Tsuruta et al. ............ 227/175.1 |
| 5,486,187 | A | 1/1996 | Schenck |
| 5,669,918 | A | 9/1997 | Balazs et al. |
| 5,695,504 | A | 12/1997 | Gifford, III et al. |
| 5,702,412 | A | 12/1997 | Popov et al. |
| 5,707,380 | A | 1/1998 | Hinchliffe et al. |
| 5,709,335 | A | 1/1998 | Heck |
| 5,725,537 | A | 3/1998 | Green et al. |
| 5,732,872 | A | 3/1998 | Bolduc et al. |
| 5,779,718 | A | 7/1998 | Green et al. |
| 5,797,934 | A | 8/1998 | Rygaard |
| 5,817,113 | A | 10/1998 | Gifford, III et al. |
| 5,823,956 | A | 10/1998 | Roth et al. |
| 5,827,316 | A | 10/1998 | Young et al. |
| 5,833,698 | A | 11/1998 | Hinchliffe et al. |
| 5,839,639 | A | 11/1998 | Sauer et al. |
| 5,855,614 | A | 1/1999 | Stevens et al. |
| 5,881,943 | A | 3/1999 | Heck et al. |
| 5,891,160 | A | 4/1999 | Williamson, IV et al. |
| 5,904,697 | A | 5/1999 | Gifford, III et al. |
| 5,916,226 | A | 6/1999 | Tozzi |
| 5,944,730 | A | 8/1999 | Nobles et al. |
| 5,947,363 | A | 9/1999 | Bolduc et al. |
| 5,951,576 | A | 9/1999 | Wakabayashi |
| 5,957,363 | A | 9/1999 | Heck |
| 5,957,879 | A | 9/1999 | Roberts et al. |
| 5,961,481 | A | 10/1999 | Sterman et al. |
| 5,964,782 | A | 10/1999 | Lafontaine et al. |
| 5,971,973 | A | 10/1999 | Peters |
| 5,972,030 | A | 10/1999 | Garrison et al. |
| 5,976,159 | A | 11/1999 | Bolduc et al. |
| 5,993,468 | A | 11/1999 | Rygaard |
| 6,015,416 | A | 1/2000 | Stefanchik et al. |
| 6,024,748 | A | 2/2000 | Manzo et al. |
| 6,030,395 | A | 2/2000 | Nash et al. |
| 6,036,705 | A | 3/2000 | Nash et al. |
| 6,056,762 | A | 5/2000 | Nash et al. |
| 6,066,144 | A | 5/2000 | Wolf et al. |
| 6,080,173 | A | 6/2000 | Williamson, IV et al. |
| 6,083,234 | A | 7/2000 | Nicholas et al. |
| 6,110,187 | A | 8/2000 | Donlon |
| 6,171,319 | B1 | 1/2001 | Nobles et al. |
| 6,171,321 | B1 | 1/2001 | Gifford, III et al. |
| 6,176,413 | B1 | 1/2001 | Heck et al. |
| 6,176,864 | B1 | 1/2001 | Chapman |
| 6,183,486 | B1 | 2/2001 | Snow et al. |
| 6,187,019 | B1 | 2/2001 | Stefanchik et al. |
| 6,187,020 | B1 | 2/2001 | Zegdi et al. |
| 6,187,022 | B1 | 2/2001 | Alexander, Jr. et al. |
| 6,190,397 | B1 | 2/2001 | Spence et al. |
| 6,190,590 | B1 | 2/2001 | Randall et al. |
| 6,193,734 | B1 | 2/2001 | Bolduc et al. |
| 6,197,042 | B1 | 3/2001 | Ginn et al. |
| 6,206,913 | B1 | 3/2001 | Yencho et al. |
| 6,231,506 | B1 | 5/2001 | Hu et al. |
| 6,234,995 | B1 | 5/2001 | Peacock, III |
| 6,241,741 | B1 | 6/2001 | Duhaylongsod et al. |
| 6,241,742 | B1 | 6/2001 | Spence et al. |
| 6,241,743 | B1 | 6/2001 | Levin et al. |
| 6,248,117 | B1 | 6/2001 | Blatter |
| 6,253,984 | B1 | 7/2001 | Heck et al. |
| 6,254,615 | B1 | 7/2001 | Bolduc et al. |
| 6,254,617 | B1 | 7/2001 | Spence et al. |
| 6,280,460 | B1 | 8/2001 | Bolduc et al. |
| 6,332,468 | B1 | 12/2001 | Benetti |
| 6,338,712 | B2 | 1/2002 | Spence et al. |
| 6,346,074 | B1 | 2/2002 | Roth |
| 6,350,252 | B2 | 2/2002 | Ray et al. |
| 6,361,543 | B1 | 3/2002 | Chin et al. |
| 6,371,965 | B2 | 4/2002 | Gifford, III et al. |
| 6,387,105 | B1 | 5/2002 | Gifford, III et al. |
| 6,391,039 | B1 | 5/2002 | Nicholas et al. |
| 6,401,721 | B1 | 6/2002 | Maginot |
| 6,440,146 | B2 | 8/2002 | Nicholas et al. |
| 6,443,965 | B1 | 9/2002 | Gifford, III et al. |
| 6,450,390 | B2 | 9/2002 | Heck et al. |
| 6,451,034 | B1 | 9/2002 | Gifford, III et al. |
| 6,461,365 | B2 | 10/2002 | Bolduc et al. |
| 6,471,713 | B1 | 10/2002 | Vargas et al. |
| 6,562,037 | B2 | 5/2003 | Paton et al. |
| 6,726,697 | B2 | 4/2004 | Nicholas et al. |
| 6,769,594 | B2 | 8/2004 | Orban, III |

FOREIGN PATENT DOCUMENTS

| | | |
|---|---|---|
| EP | 594004 A1 | 4/1994 |
| EP | 643946 A | 3/1995 |
| EP | 656191 A2 | 6/1995 |
| EP | 820725 B1 | 7/1997 |
| EP | 820724 A | 1/1998 |
| EP | 885595 A1 | 12/1998 |
| EP | 1088519 A | 4/2001 |
| EP | 1088519 A1 | 4/2001 |
| FR | 1518083 | 3/1968 |
| FR | 2777446 | 10/1999 |
| GB | 935490 | 8/1963 |
| WO | WO88/01486 | 3/1988 |
| WO | WO95/15715 | 6/1995 |
| WO | WO95/17127 | 6/1995 |
| WO | WO95/35065 | 12/1995 |
| WO | WO97/40754 | 11/1997 |
| WO | WO99/11178 | 3/1999 |
| WO | WO00/69343 | 11/2000 |
| WO | WO01/52748 | 7/2001 |

OTHER PUBLICATIONS

Information Booklet for: Deep Surgery Advantage-Dramatic New Access Plus Automatic-Feed in Vessel Ligation, Hemoclip ® automatic ligating clip system, Edward Weck & Company, Inc.Sep. 1996.
Information Booklet for: Auto Suture® Premium Surgliclip™ Titanium disposable automatic clip appliers, United States Surgical Corporation, 1981.
PCT/US03/18295 International Search Report.

* cited by examiner

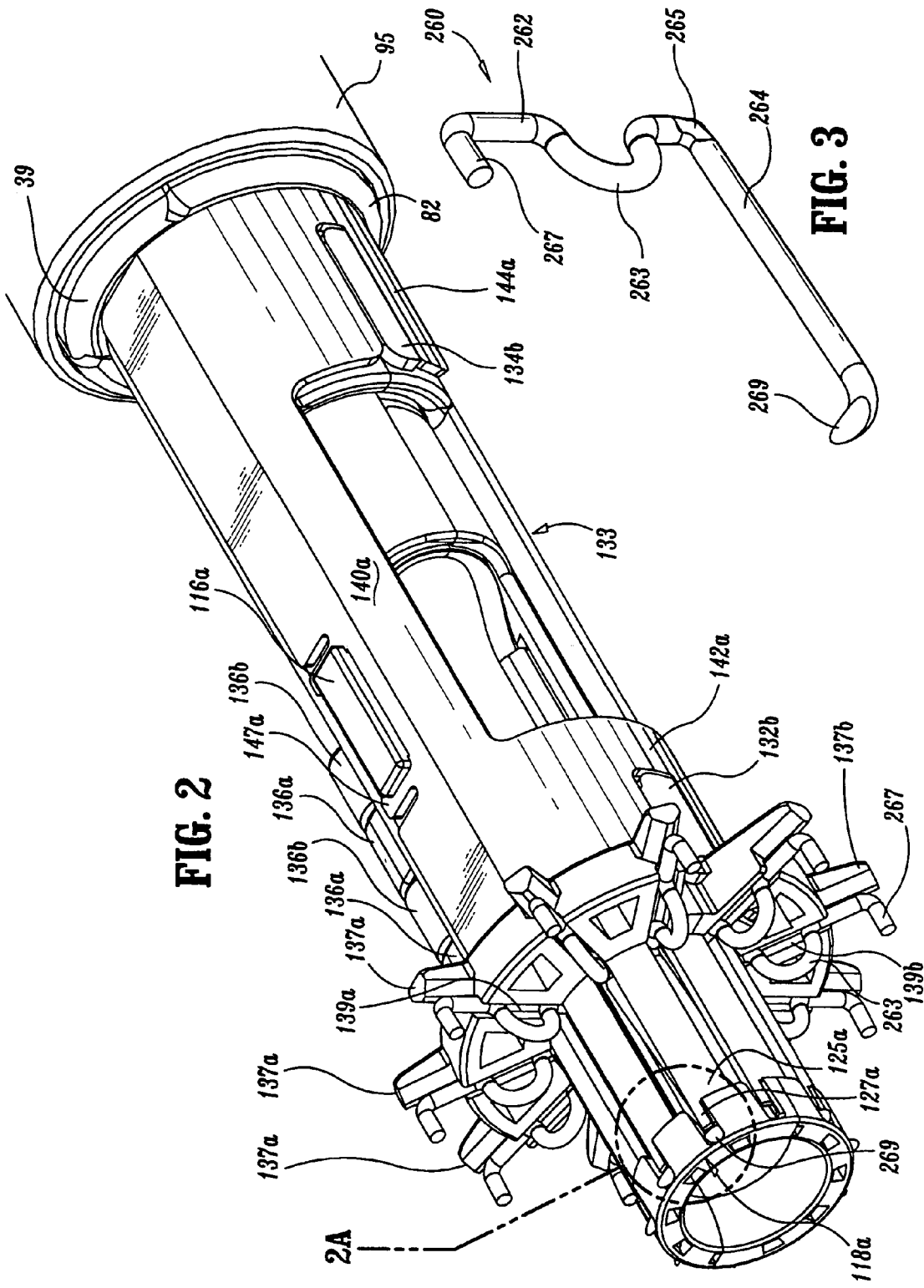

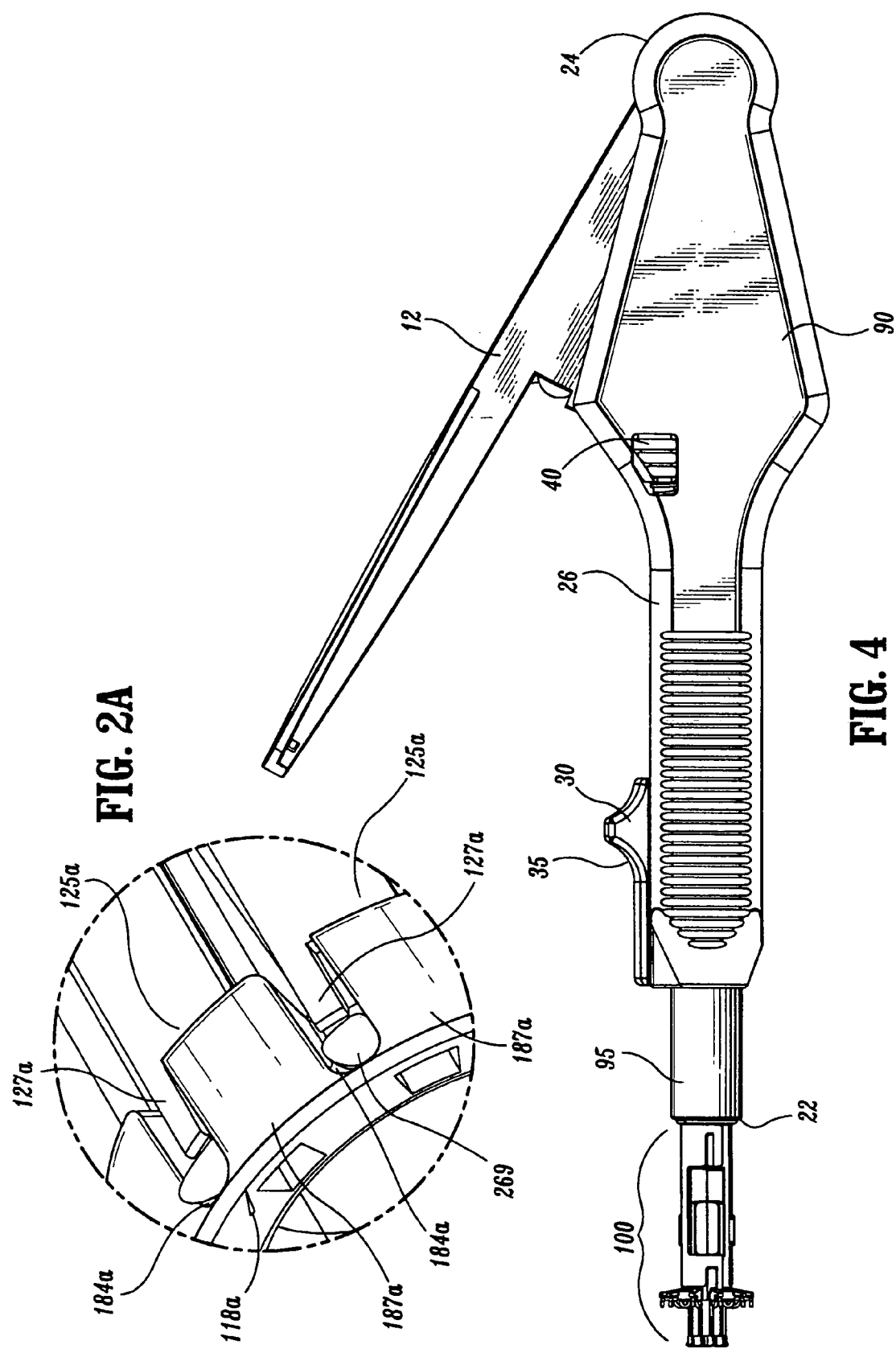

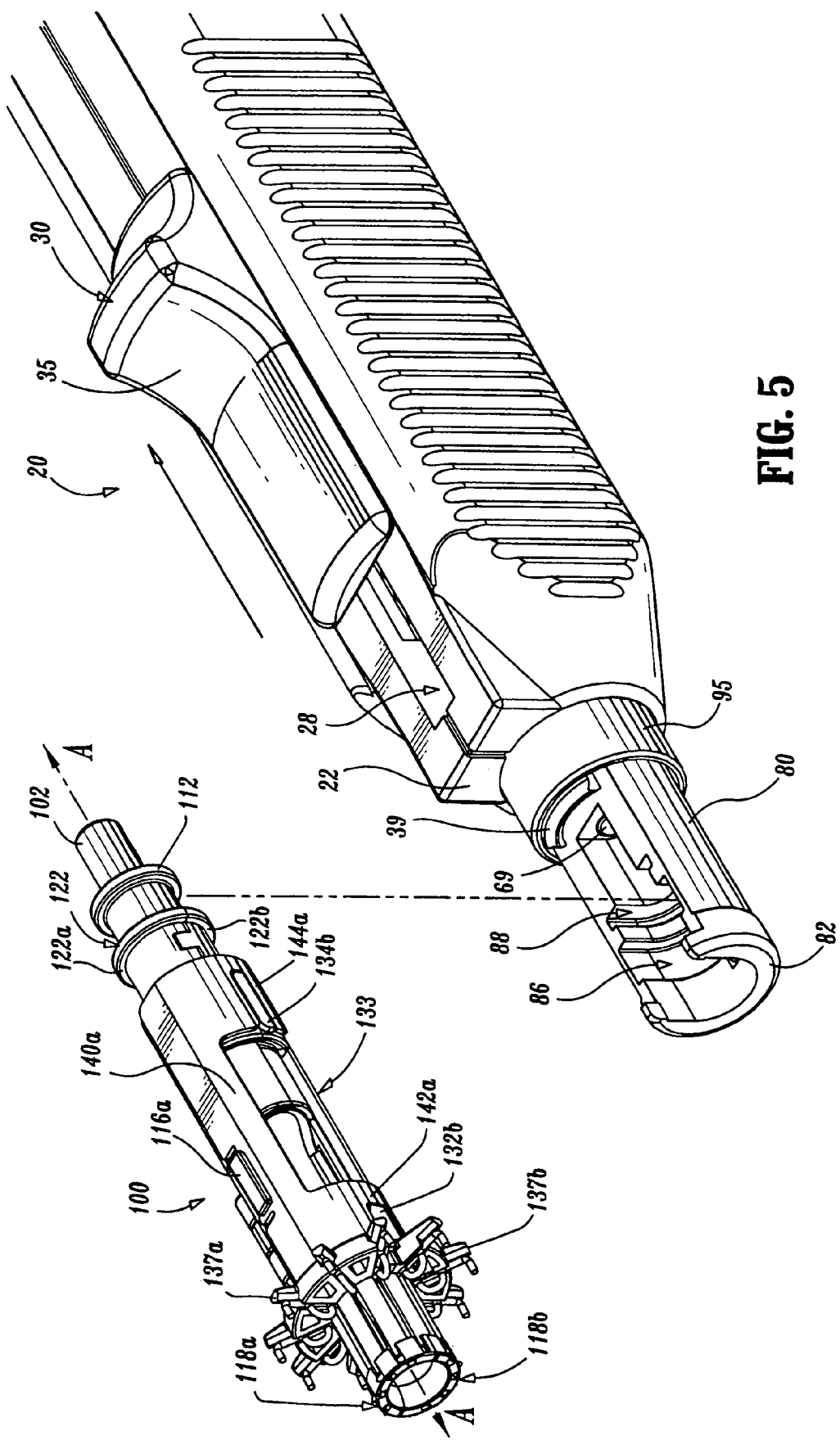

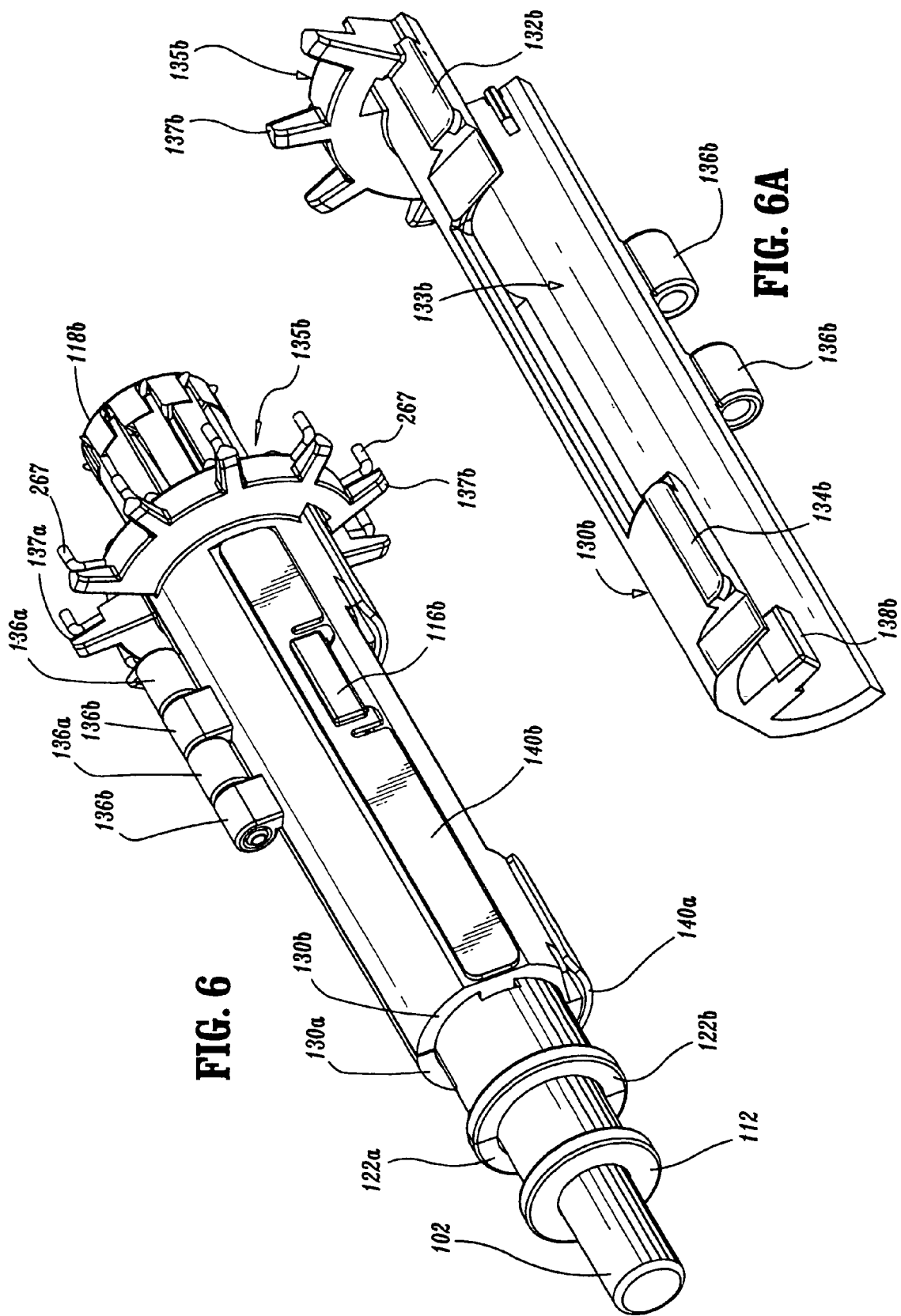

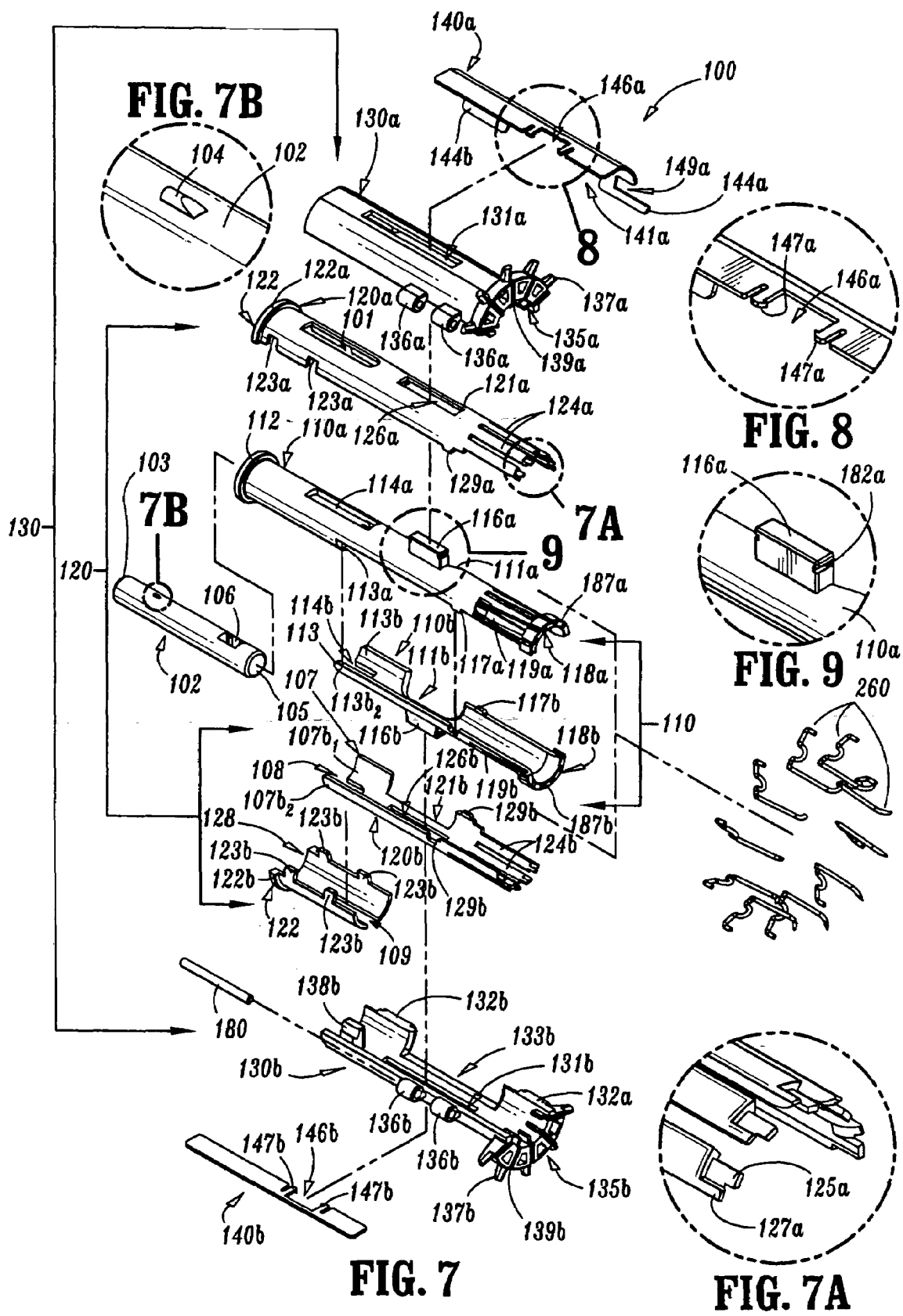

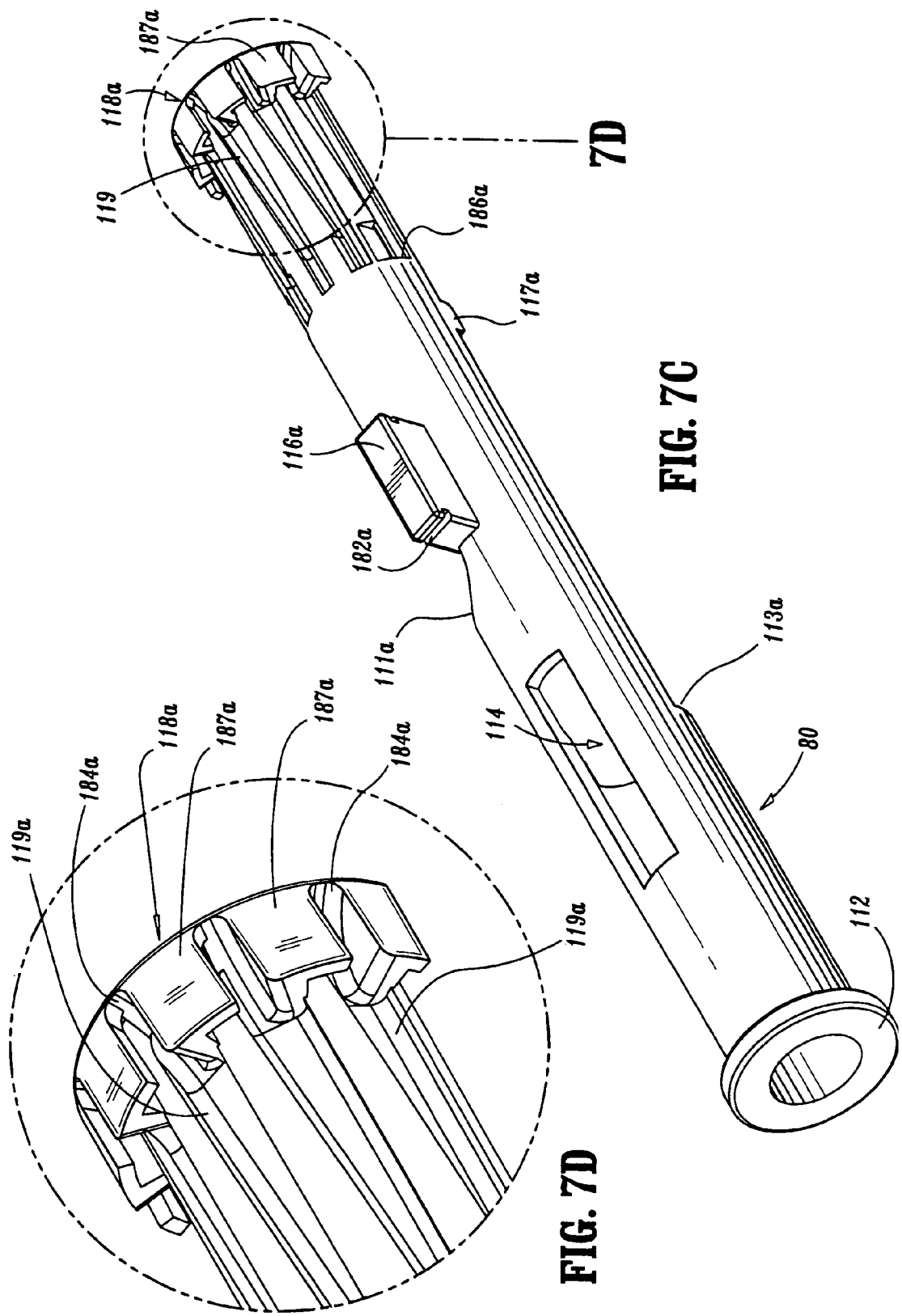

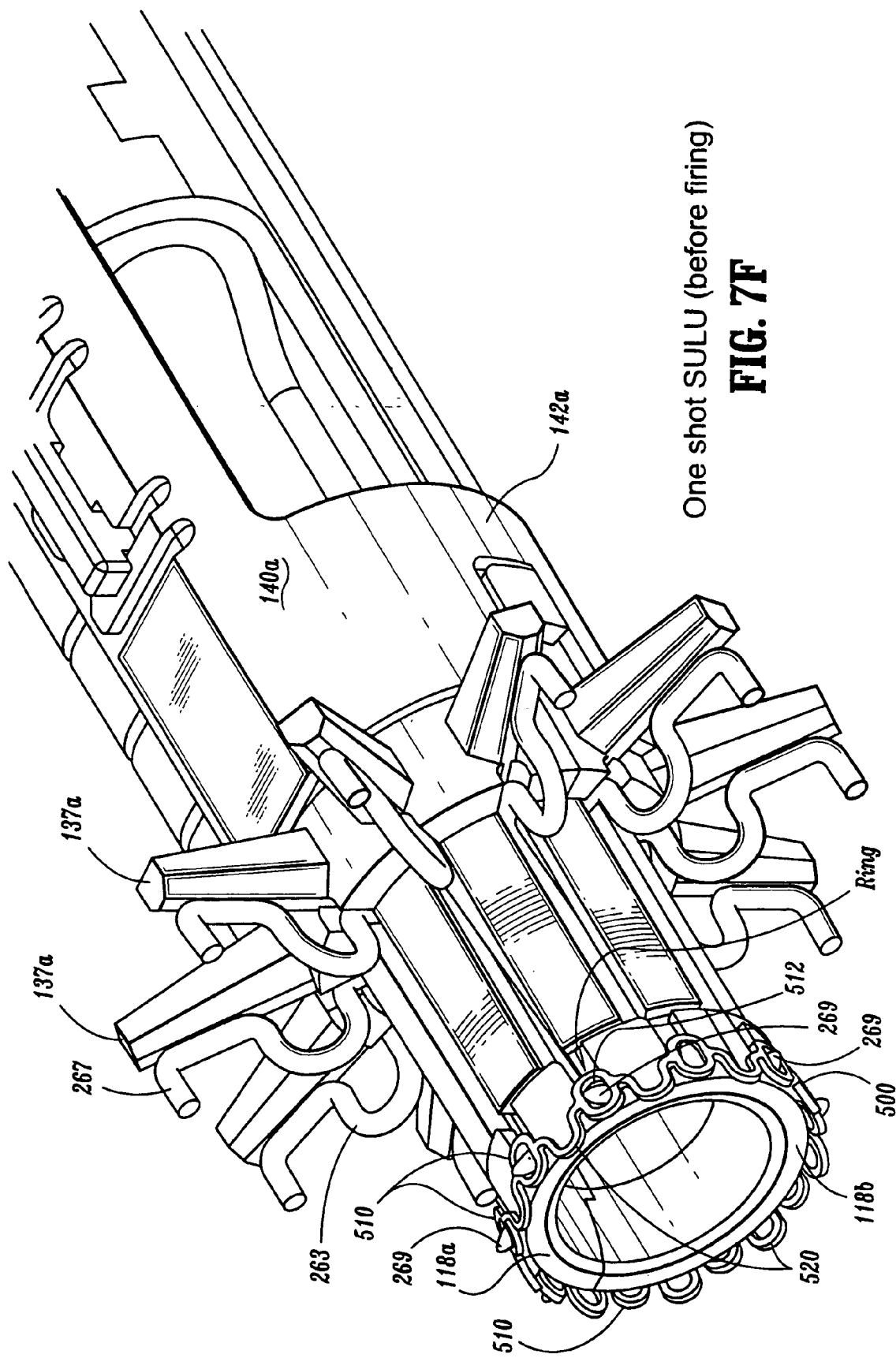

One shot SULU (after firing)

ONE SHOT ANASTOMOSIS (CROSS SECTION)

Inside view of one shot
Anastomosis with ring

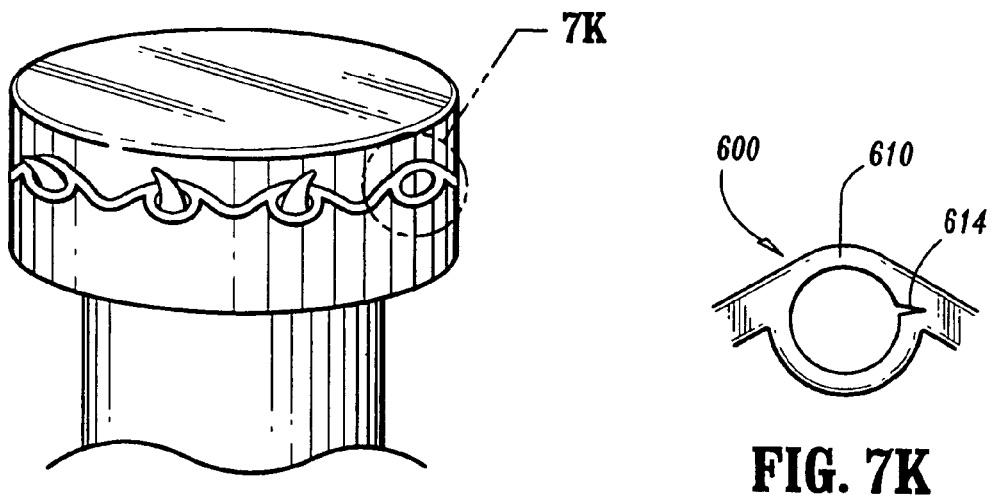
FIG. 7J
FIG. 7K
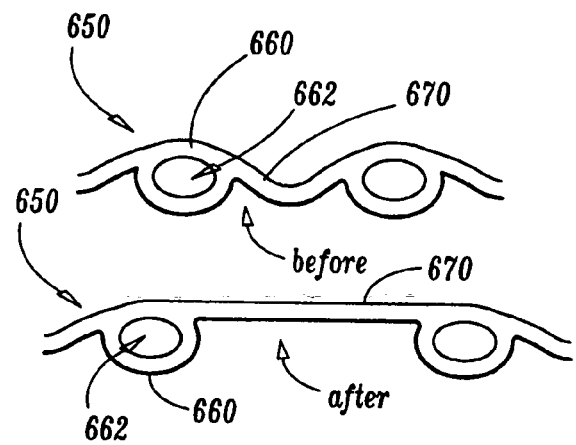
FIG. 7L
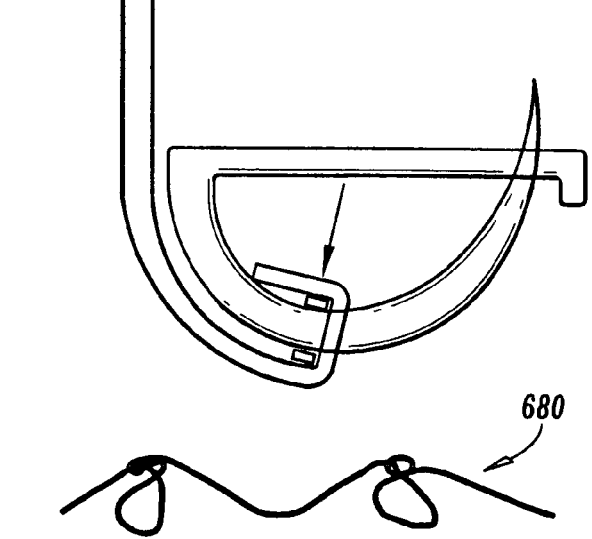
FIG. 7M

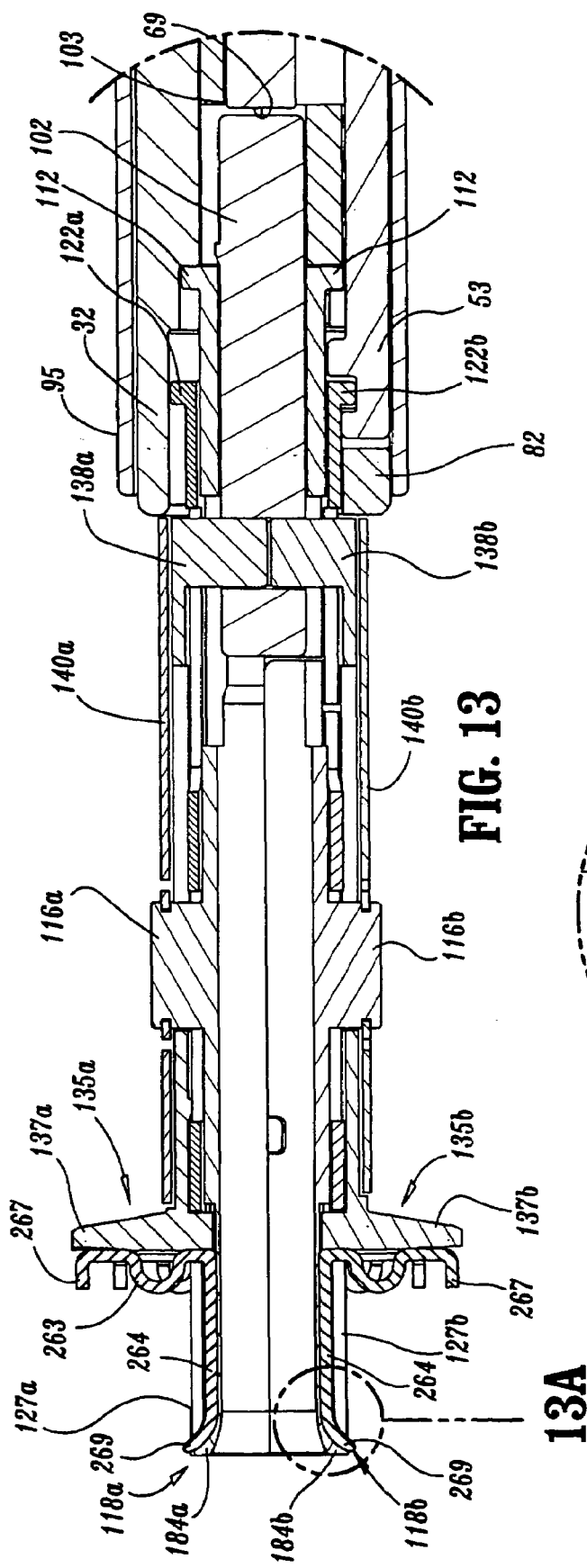
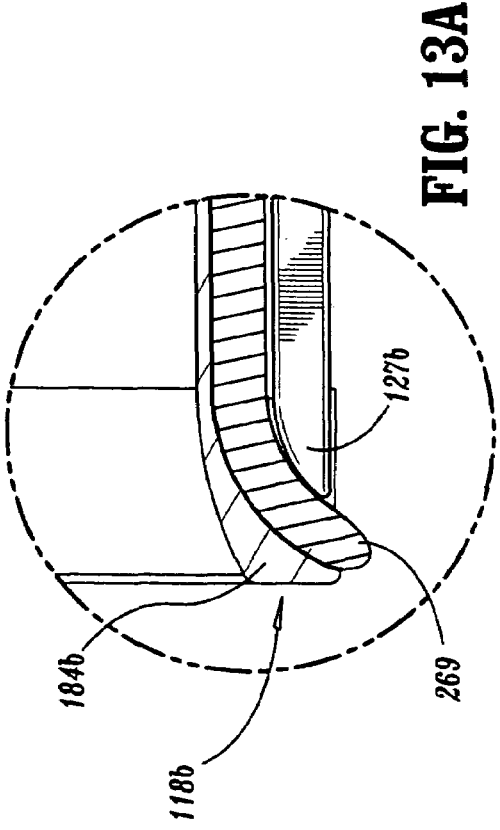
FIG. 13
FIG. 13A

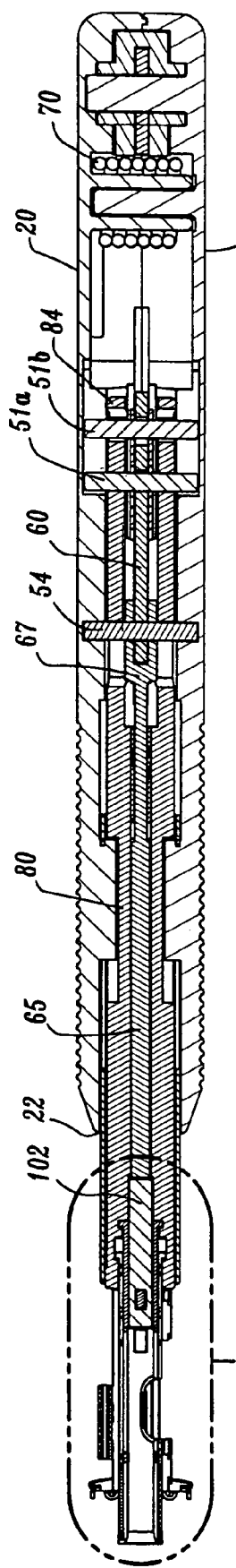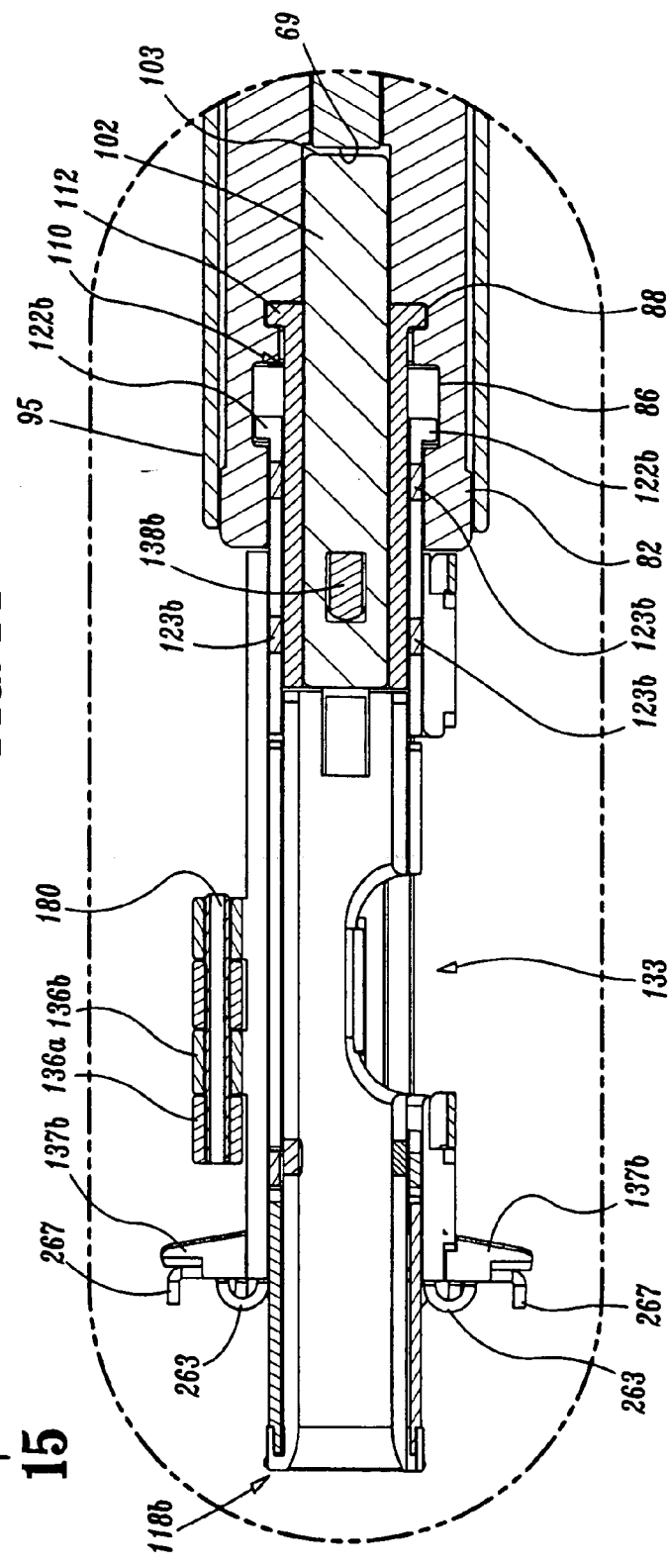
FIG. 14
FIG. 15

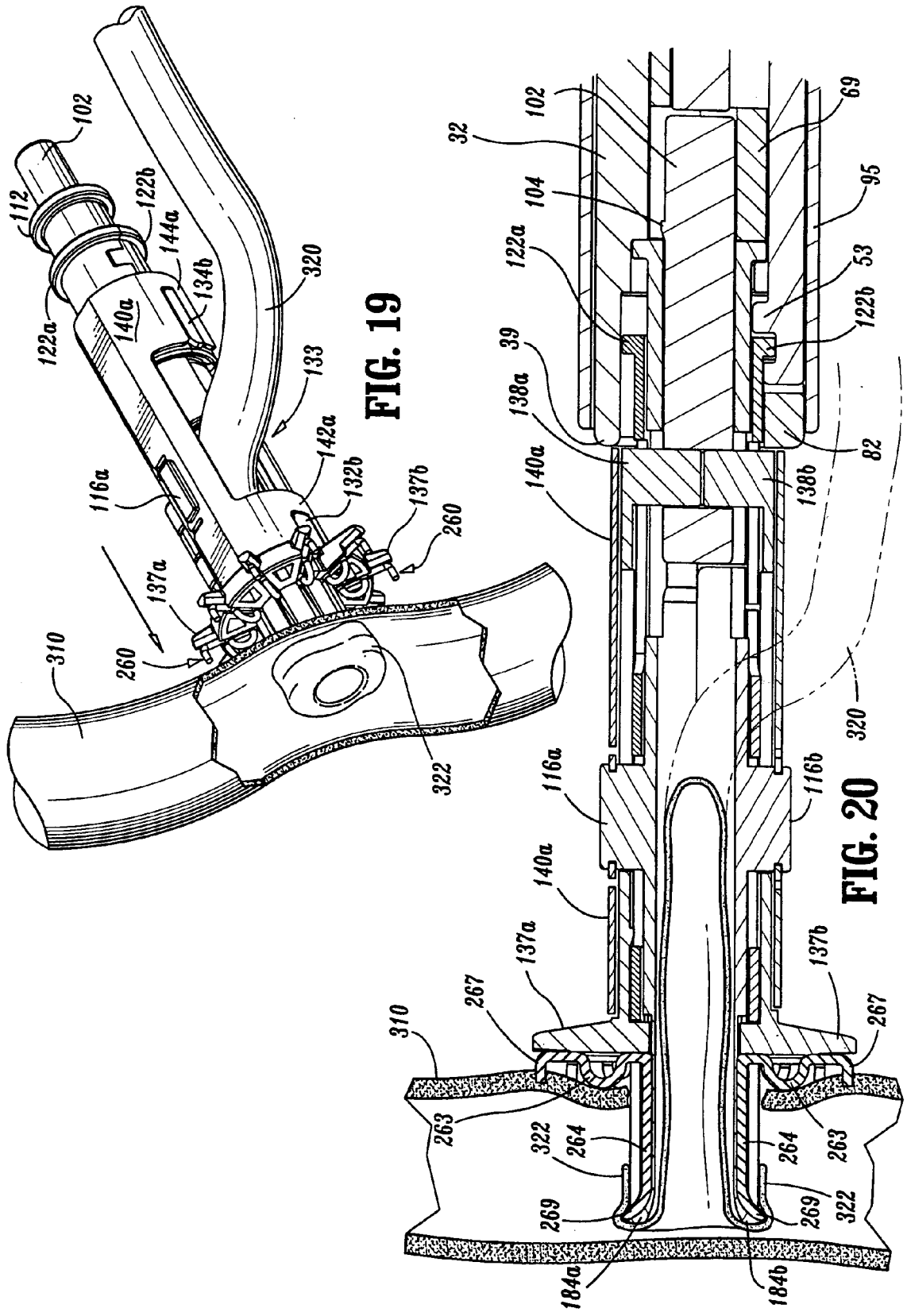

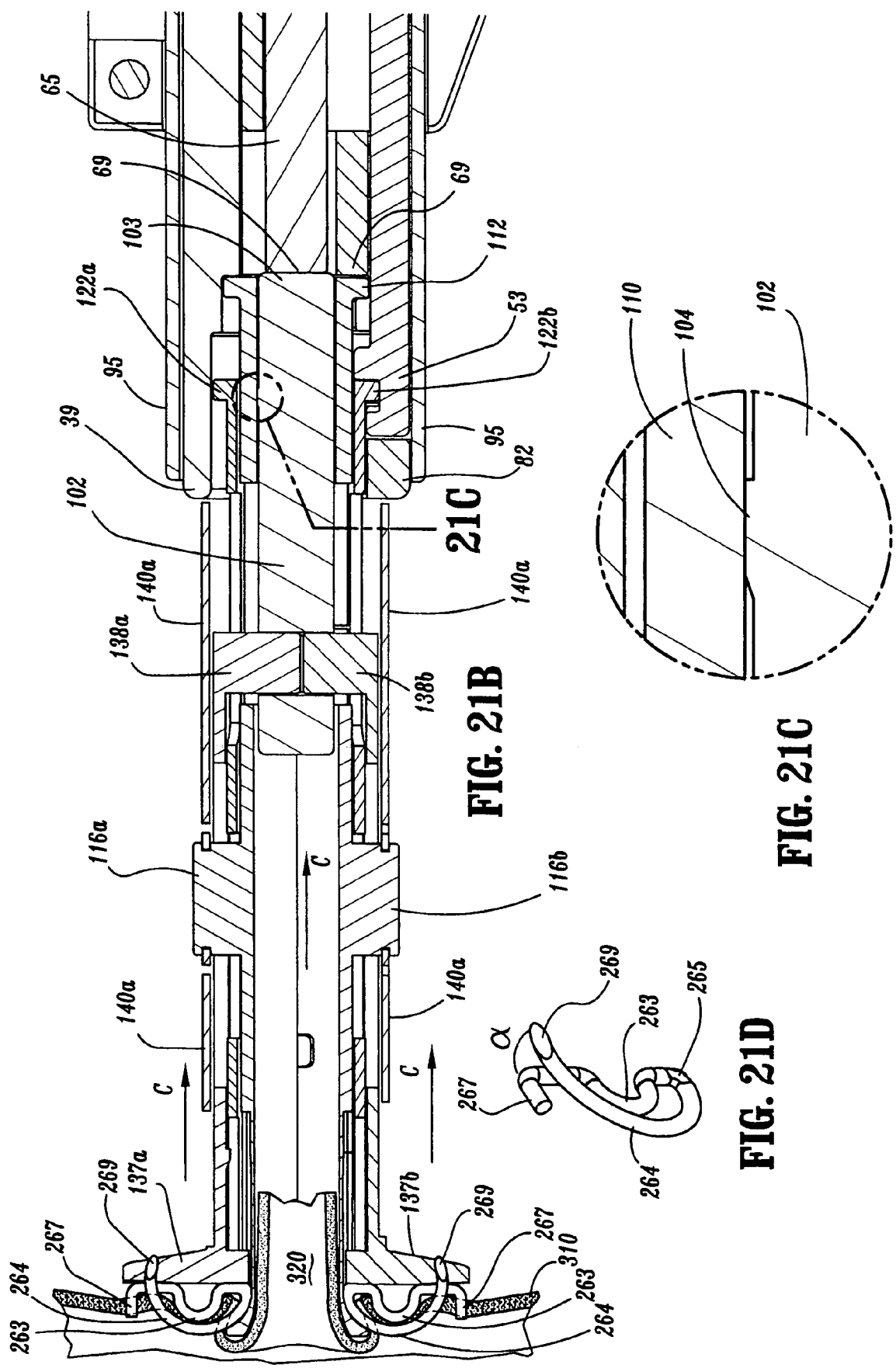

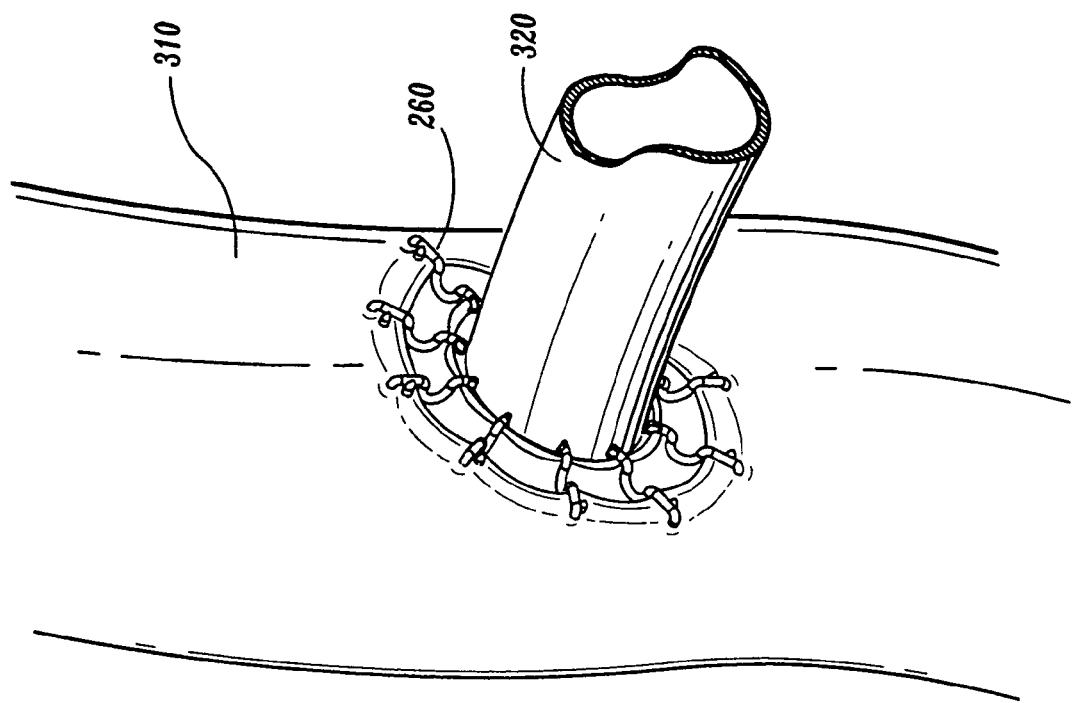
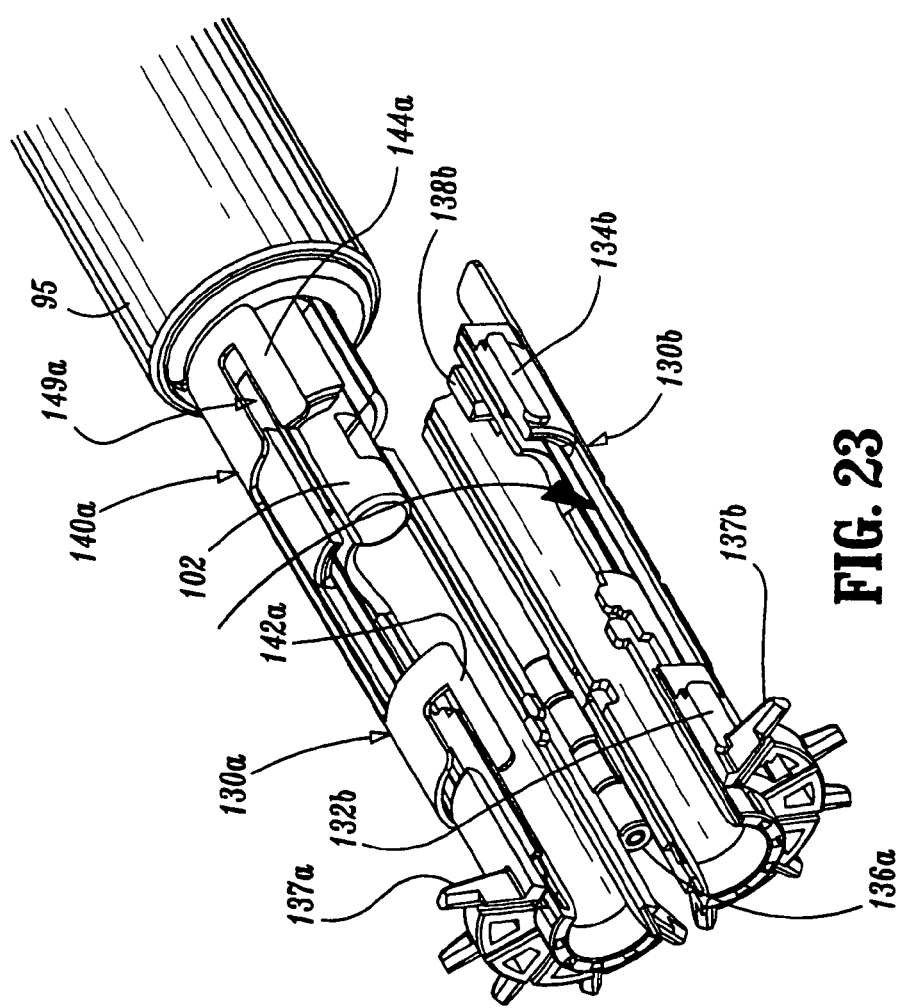
FIG. 24
FIG. 23

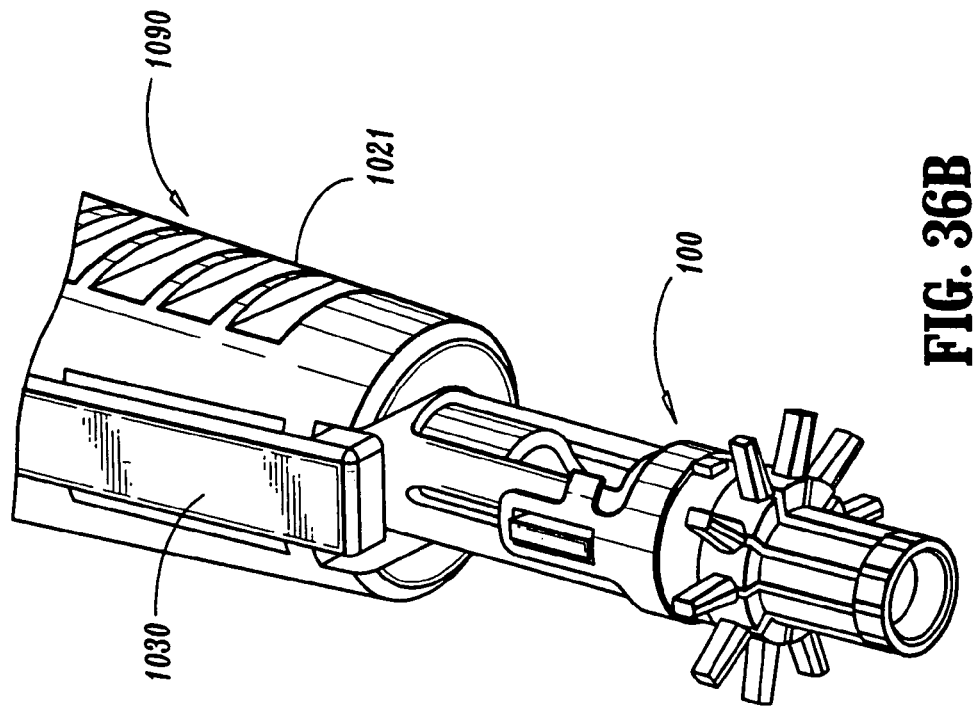
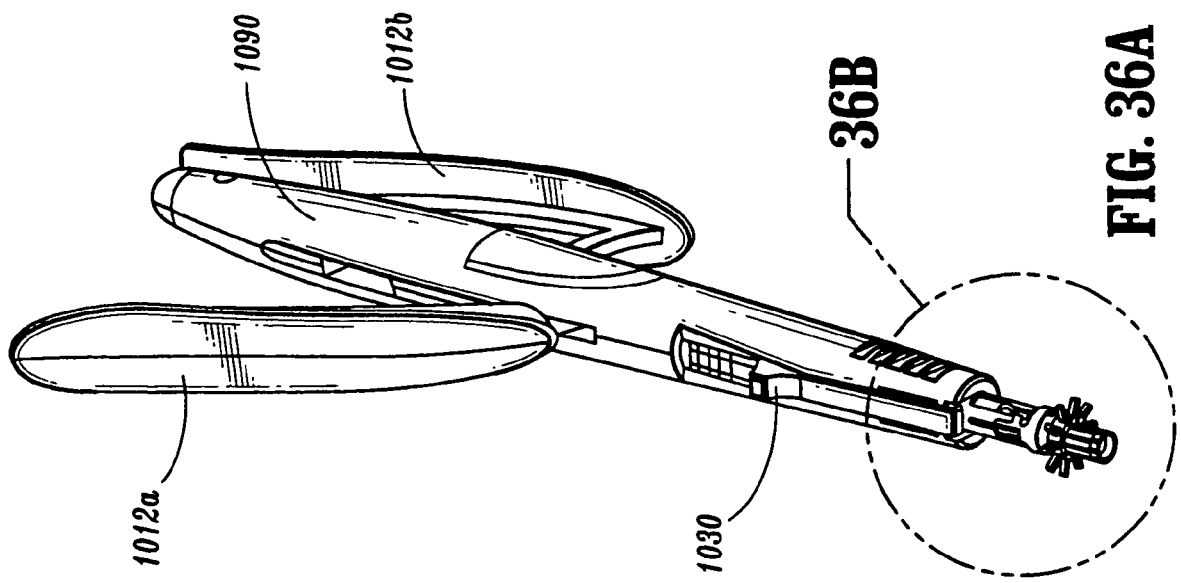

ANASTOMOSIS INSTRUMENT AND METHOD FOR PERFORMING SAME

This application is a 371 of PCT/US02/00345 filed on Jan. 8, 2002 which claims benefit of provisional application No. 60/263,861 filed on Jan. 24, 2001.

BACKGROUND

1. Technical Field

The present disclosure relates to a surgical instrument and method for performing anastomosis of tubular body structures, and more particularly to an instrument for joining vascular tissues, for example, during coronary artery bypass graft procedures.

2. Background of Related Art

Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and/or by modifications in behavior and diet. In other cases, dilatation of coronary arteries may be achieved by such procedures as angioplasty, laser ablation, atherectomy, catheterization, and intravascular stents.

For certain patients, a coronary artery bypass graft ("CABG") is the preferred form of treatment to relieve symptoms and the graft often increases life expectancy. A CABG procedure consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion. Alternatively, the internal mammary artery located in the thoracic cavity adjacent the sternum is likewise suitable for grafting to a coronary artery, such as the left anterior descending artery ("LAD").

The performance of a CABG procedure typically requires access to the heart, blood vessels and associated tissue. Access to the patient's thoracic cavity may be achieved in an open procedure by making a large longitudinal incision in the chest. This procedure, referred to as a median sternotomy, requires a saw or other cutting instrument to cut the sternum to allow the two opposing halves of the rib cages to be spread apart to expose the internal organs of the thoracic cavity.

U.S. Pat. No. 5,025,779 to Bugge discloses a retractor, which is designed to grip opposite sternum halves and spread the thoracic cavity apart. The large opening, which is created by this technique, enables the surgeon to directly visualize the surgical site and perform procedures on the affected organs. However, such procedures that involve large incisions and substantial displacement of the rib cage are often traumatic to the patient with significant attendant risks. The recovery period may be extensive and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating "window". The retractor includes a rigid frame and a translation frame slideably connected to the rigid frame. Lower and upper blades are rotatably mounted to the rigid frame and the translation frame respectively. The "window" approach enables the surgeon to gain access through a smaller incision and with less displacement of the ribs, and consequently, less trauma to the patient.

Once access to the thoracic cavity has been achieved, surgery on the heart may be performed. Such procedures typically require that the heartbeat be arrested while maintaining circulation throughout the rest of the body. Cardioplegic fluid, such as potassium chloride (KCI) is delivered to the blood vessels of the heart to paralyze the myocardium. As disclosed in WO 95/15715 to Sterman et al. for example, cardioplegic fluid is infused into the myocardium through the coronary arteries by a catheter inserted into the ascending aorta.

Alternatively, cardioplegic fluid is infused through the coronary veins in a retrograde manner by a catheter positioned in the interior jugular vein accessed at the patient's neck. Such procedures require the introduction of multiple catheters into the blood vessels adjacent the heart, which is a complicated procedure requiring that the desired vessels be properly located and accessed. The progression of the guide wires and catheters must be closely monitored to determine proper placement. Furthermore, the introduction of catheters form punctures in the blood vessels that must be subsequently closed, and there is an increased risk of trauma to the interior walls of the vessels in which the catheters must pass.

Alternatively, the CABG procedure may be performed while the heart is permitted to beat. Such a procedure is now commonly referred to as minimally invasive direct coronary artery bypass (MIDCAB) when performed through a thoracotomy (when performed through a sternotomy, the procedure is commonly called open coronary artery bypass (OP-CAB). A surgical instrument is used to stabilize the heart and restrict blood flow through the coronary artery during the graft procedure. Special care must be given to procedures performed on a beating heart, e.g. synchronizing procedures to occur at certain stages in the cardiac cycle, such as between heartbeats.

To perform a CABG procedure, the harvested vessel segment, such as the saphenous vein, is grafted to the coronary artery by end-to-side anastomosis. Typically, sutures are used to graft the vessel segments. However, conventional suturing is complicated by the use of minimally invasive procedures, such as the window approach, e.g., limited access and reduced visibility to the surgical site may impede the surgeon's ability to manually apply sutures to a graft. Additionally, it is difficult and time consuming to manually suture if the CABG procedure is being performed while the heart is beating as the suturing must be synchronized with the heart beat.

As can be appreciated, the process of manually suturing the harvested vessel segment to a coronary artery is time consuming and requires a great deal of skill on the part of the surgeon. The resulting sutured anastomosis will also be dependent on the skills of the surgeon. In minimally invasive procedures such as in MIDCAB, the ability to suture is even more complicated due to limited maneuverability and reduced visibility. U.S. Pat. No. 5,707,380 to Hinchliffe et al., the entire contents of which are hereby incorporated by reference, discloses an apparatus and a procedure that enable remote anastomosis without piercing of vessels during both conventional and minimally invasive procedures. A continuing need exists, however, for improved surgical instruments and methods for performing remote anastomoses during both conventional and minimally invasive procedures.

SUMMARY

A surgical instrument for anastomosis of first and second blood vessels includes a housing having distal and proximal ends and an actuator disposed therebetween. The actuator includes a handle and a link assembly, the link assembly being movable through a firing stroke in response to movement of he handle. The instrument also includes a disposable loading unit releasably attached to the distal end of the housing in mechanical cooperation with the actuator. The disposable loading unit supports a plurality of surgical fasteners, which deform upon movement of the actuator and the link assembly through the firing stroke.

Preferably, the link assembly includes at least three links and the firing stroke of the handle includes three stages, namely, a first, pre-firing stage wherein the links are disposed at an angle relative to a horizontal axis disposed though the housing; an intermediate stage wherein the links are fully-extended and substantially parallel to the horizontal axis; and a third, post-firing stage wherein the links are disposed at an angle relative to the horizontal axis. Movement of the link assembly from the first to the second stage deforms the surgical fasteners and movement of the link assembly from the second stage to the third stage releases the surgical fasteners from the disposable loading unit.

In one embodiment, the link assembly biases a spring through the first and second stages of the firing stroke which, in turn, mechanically facilitates movement of the link assembly from the second to third stages to release the surgical fasteners. In another embodiment, the surgical instrument includes a second handle to facilitate activation of the actuator. Still, another embodiment of the surgical instrument includes a handle, which has a tab, which locks the handle in proximate relation to the housing after completion of the firing stroke.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

An illustrative embodiment of the subject surgical instrument and method are described herein with reference to the drawings wherein:

FIG. 2 is an enlarged, partial perspective view of a single use loading unit (hereinafter "SULU") constructed in accordance with a preferred embodiment of the present disclosure;

FIG. 2A is an enlarged, perspective view of the indicated area of detail of FIG. 2;

FIG. 3 is a perspective view of a surgical fastener which is designed for operative engagement with the SULU for creating vascular anastomosis between two luminal vessels;

FIG. 4 is a side view the surgical instrument of FIG. 1;

FIG. 5 is an enlarged, perspective view of a distal end of the actuator assembly shown in a pre-loading position to receivingly engage the SULU;

FIG. 6 is a reverse, perspective view of the SULU of FIG. 2;

FIG. 6A is a reverse, perspective view of a lower half of the SULU of FIG. 2;

FIG. 7 is a perspective view with parts separated of the SULU of FIG. 2;

FIG. 7A is a greatly enlarged, perspective view of the indicated area of detail of FIG. 7;

FIG. 7B is a greatly enlarged, perspective view of the indicated area of detail of FIG. 7;

FIG. 7C is an enlarged, perspective view of a base portion of a first retracting sleeve;

FIG. 7D is a greatly enlarged, perspective view of the indicated area of detail of FIG. 7C;

FIG. 7F is an enlarged, partial perspective view of the SULU of FIG. 2 with the retaining ring of FIG. 7E positioned about the surgical fastener prior to firing the SULU;

FIG. 7J is an enlarged view of an alternate embodiment of the retaining ring which may be incorporated with the SULU to maintain the vascular anastomosis between the two luminal vessels;

FIG. 7K is an enlarged view of the area of detail of FIG. 7J showing a slit formed along an inner periphery of one of the apertures of the ring;

FIG. 7L is an enlarged view of another alternate embodiment of the retaining ring, which straightens after firing the SULU;

FIG. 7M is an enlarged view of another alternate embodiment of a retaining ring which is constructed of a thin wire-like material;

FIG. 8 is a greatly enlarged, perspective view of the indicated area of detail of FIG. 7;

FIG. 9 is a greatly enlarged, perspective view of the indicated area of detail of FIG. 7;

FIG. 13 is a horizontal cross-sectional view of the indicated area of detail of FIG. 12;

FIG. 13A is a greatly enlarged horizontal cross sectional view of the area indicated in detail of FIG. 13;

FIG. 14 is a top cross-sectional view of the surgical instrument taken along section line 14-14 of FIG. 12;

FIG. 15 is a greatly enlarged top cross-sectional view of the area indicated in detail of FIG. 14;

FIG. 19 is an internal, perspective view of the second vessel with the SULU and the everted first vessel shown inserted therein;

FIG. 20 is a side cross-sectional view of the SULU and the everted first vessel shown inserted within the second vessel in pre-firing position;

FIG. 21B is a side cross-sectional view showing the movement of the SULU during the first firing stage to deform the surgical fasteners;

FIG. 21C is a greatly enlarged side cross-sectional view of the area indicated in detail in FIG. 21B;

FIG. 21D is a greatly enlarged perspective view of the surgical fastener shown in a "stapled" configuration;

FIG. 23 is a perspective view of the SULU showing the pivotable movement of the two supports, which open after firing to release the first vessel;

FIG. 24 is a view showing a completed anastomosis;

FIG. 33-37B shows another embodiment of the surgical instrument constructed in accordance with an embodiment of the present disclosure.

DETAILED DESCRIPTION

Figure 1:
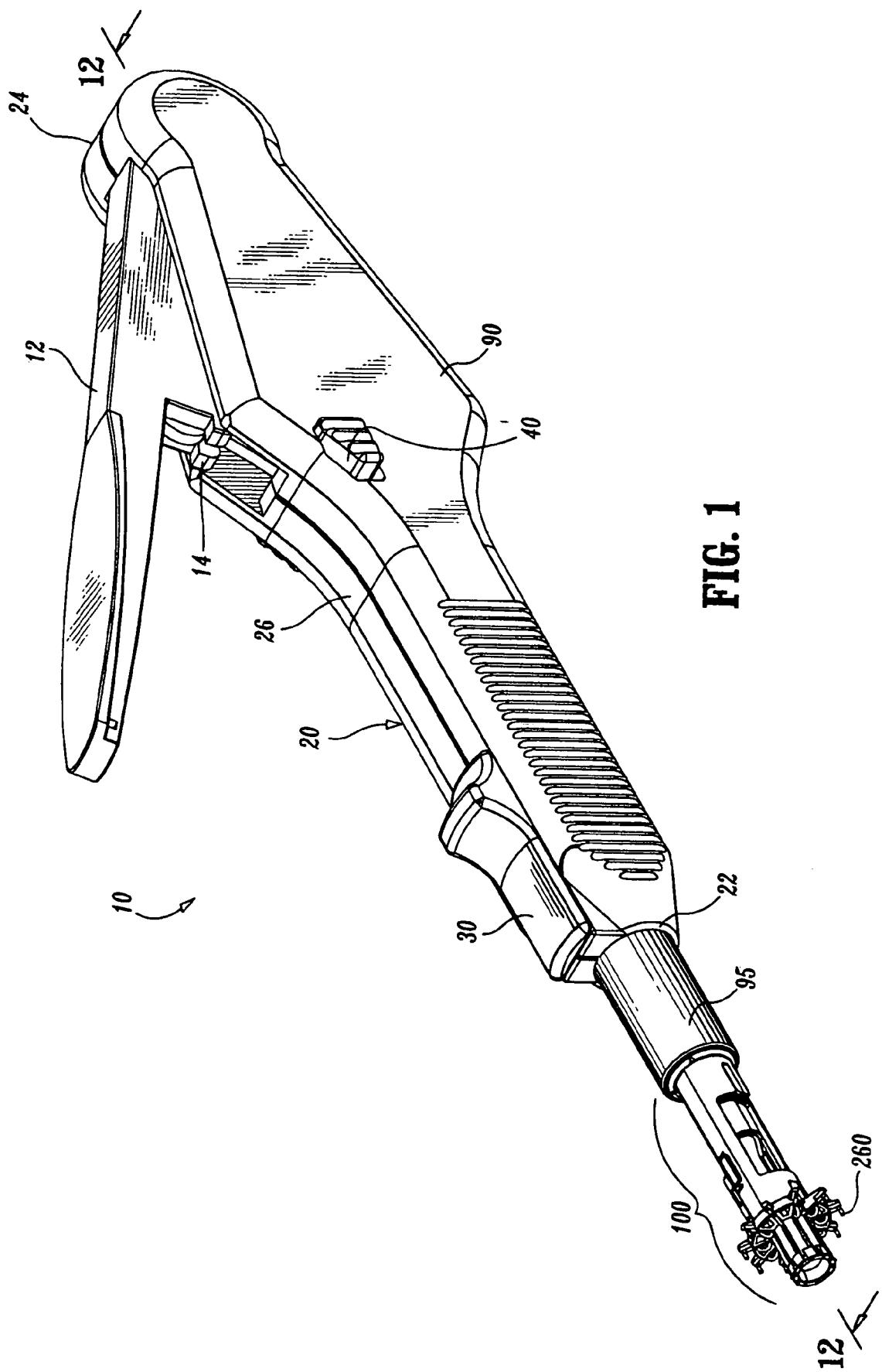
FIG. 1 is a perspective view of a surgical instrument constructed in accordance with an embodiment of the present disclosure.
Figure 4A:
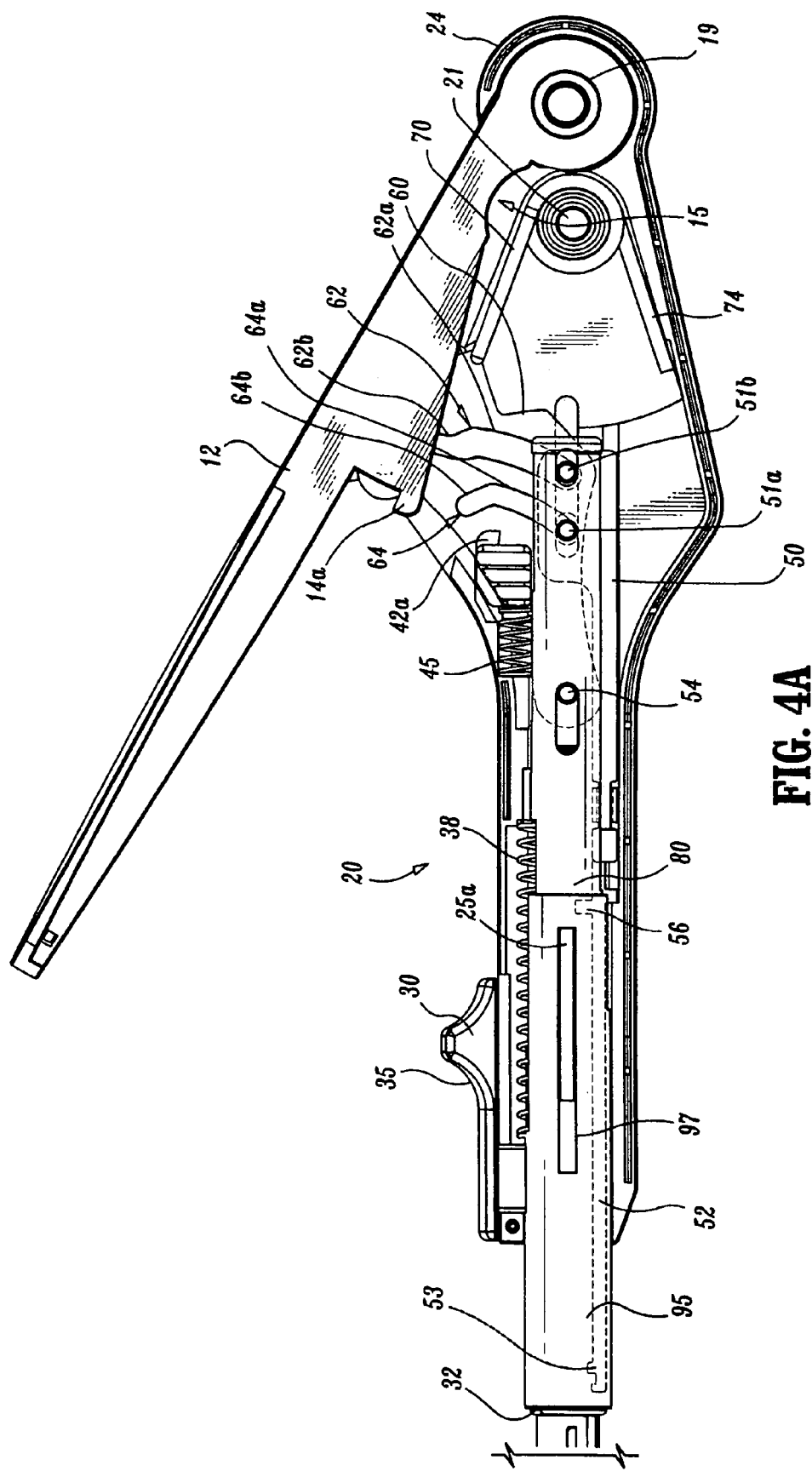
FIG. 4A is a left, side view of a handle/actuator assembly of the surgical instrument of FIG. 1 shown without a cover plate attached thereto.

Preferred embodiments of the surgical instrument and method disclosed herein will be described in terms of a coronary artery bypass procedure wherein a vascular anastomosis is created by joining a section of a harvested vessel, e.g., the saphenous vein, to bypass an occlusion in a coronary artery, e.g., the left anterior descending artery ("LAD"). Alternatively, the presently disclosed surgical instrument may also be utilized in performing anastomosis of other tubular luminal body structures.

In the drawings and in the description which follows, the term "proximal", as is traditional, will refer to the end of the apparatus which is closer to the user, while the term "distal" will refer to the end which is further from the user.

Referring now in detail to the drawing figures in which like reference numerals identify similar or identical elements, one embodiment of the present disclosure is illustrated generally in FIG. 1 and is designated therein as surgical instrument 10. Surgical instrument 10 includes two principal components, namely, an actuator assembly 20 and a disposable loading unit ("DLU") or a single use loading unit ("SULU") 100, which along with their internal working components, mechanically cooperate to deform a surgical fastener 260 to complete an anastomosis between two vessels, e.g., an saphenous vein 320 and an aorta 310 (FIG. 21B).

The particular surgical instrument 10 shown in the various figures is preferably designed to deform an array of surgical fasteners similar to fastener 260 shown in FIG. 3 which is generally L-shaped and includes a base leg 264 and an upwardly extending support leg 262. Preferably, base leg 264 includes a distal end 269, which is sufficiently shaped to penetrate the saphenous vein 320 and aorta 310 upon deformation of the surgical fastener 260. The upwardly extending support leg 262 is attached to base leg 264 at a pivot point 265 and includes an inwardly extending prong 267 disposed at its free end designed to penetrate the aorta 310 and secure surgical fastener 260 in position after anastomosis. It is envisioned that pivot point 265 may also be dimensioned to include a relief or coined section 261 which may facilitate formation of the surgical fastener 260 which will be explained in more detail below with respect to the operation of the surgical instrument 10 (See FIGS. 7N and 7S).

Turning back in detail to FIG. 3, a convexity 263 projects inwardly between the base leg 264 and the support leg 262 and is preferably sufficiently dimensioned to cooperate with the base leg 264 to retain the saphenous vein 320 against aorta 310 in fluid communication after anastomosis as will be explained in greater detail below with respect to FIGS. 21B and 24. It is envisioned that the surgical fastener 260 can be arranged on the SULU in different patterns/arrays depending upon a particular purpose.

As best seen in FIGS. 1, 4, 10 and 11, actuator assembly 20 includes a proximal end 24, a distal end 22 and a housing 26 defined therebetween for storing the internal working components of the actuator assembly 20. Preferably, a plate 90 covers the internal components of the actuator assembly 20 when assembled. More particularly, housing 26 includes at least one mechanical interface 23a which reciprocates with a corresponding mechanical interface 23b (FIG. 10) disposed on cover plate 90 to matingly engage the two components 26 and 90.

Actuator assembly 20 also includes a handle 12 which initiates firing of the surgical instrument 10 and a spring-loaded thumb tab 30 for loading the SULU 100 onto the actuator assembly 20 both of which will be explained in greater detail below. Preferably, handle 12 is provided with an ergonomic surface, which is contoured and configured to be comfortably gripped by the hand of the user during operation of the instrument.

Figure 11:
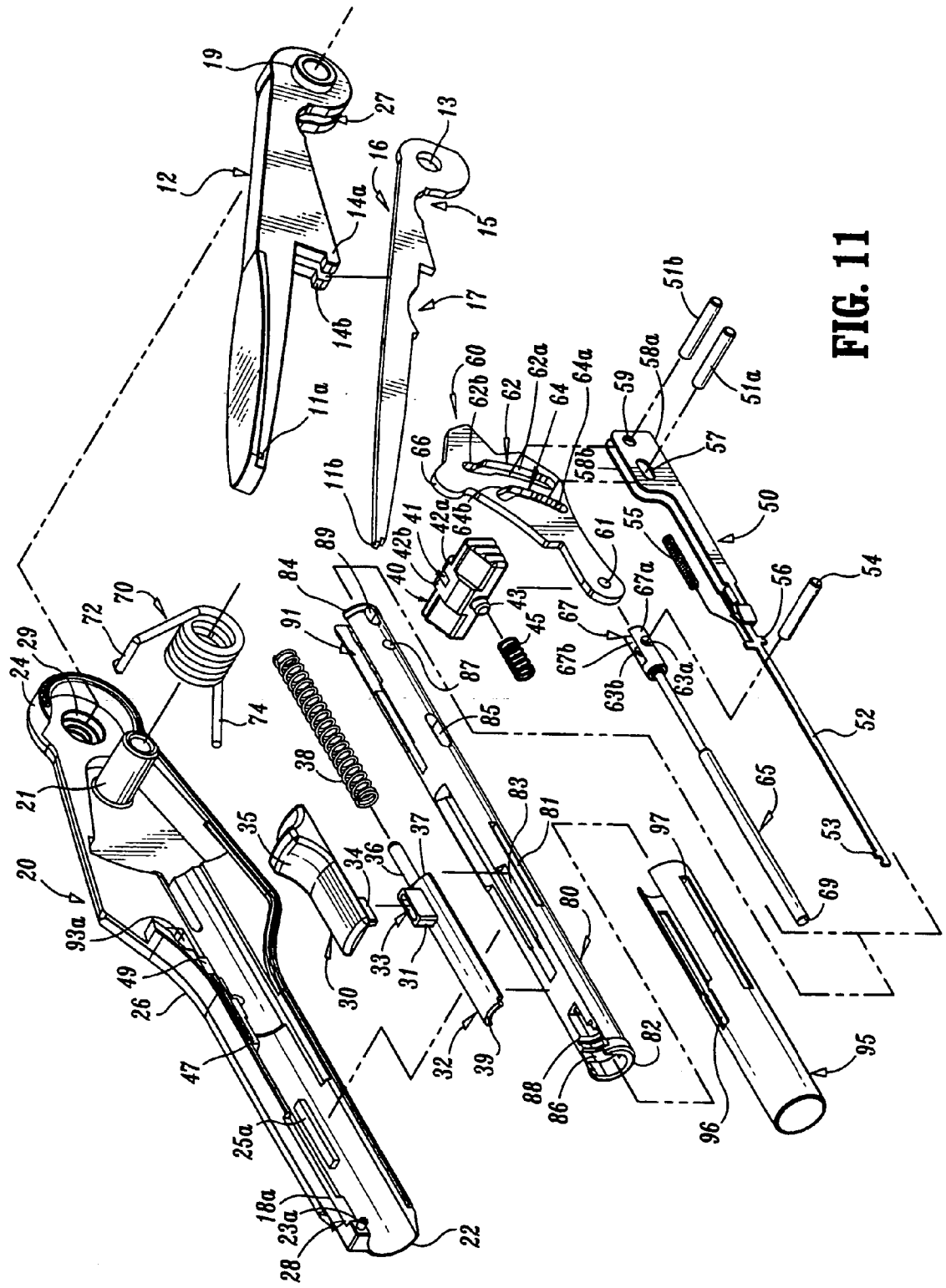
FIG. 11 is a perspective view the actuator assembly of FIG. 10 shown with parts separated.

Turning now to FIG. 11 which illustrates in detail the internal working components of the actuating assembly 20, which are preferably assembled and stored within housing 26.

More particularly, the actuating assembly 20 includes a torsion spring 70, which mounts about post 21, which protrudes from housing 26. Spring 70 includes a lower arm 74, which is biased against a lower portion of the housing, and an upper arm 72, which is biased against a rotating two-stage cam 60.

Handle 12 includes a bushing 19 which protrudes laterally from the proximal end of the handle 12 and pivotally engages a corresponding recess 29 disposed within the proximal end 24 of housing 26 to allow pivotal movement of the handle 12 with respect to housing 26. Handle 12 also includes a vertically extending slot 27 disposed at its proximal end 24 which receives the proximal end of a lever 16 which moves in conjunction with the handle 12. A pair of flanges 14a and 14b downwardly extend from the handle 12 and receive lever 16 therebetween. A mechanical interface 11a disposed on handle 12 engages a corresponding mechanical interface 11b disposed on lever 16 to secure the lever 16 to the handle 12. Preferably, lever 16 has a first recess 17 shaped to engage and control the movement of the cam 60 during downward movement of the handle 12, the purpose of which will be explained in more detail with respect to FIG. 21A. Lever 16 also includes a second recess 15, which helps to limit lateral movement of the spring 70 within housing 26.

Figure 10:
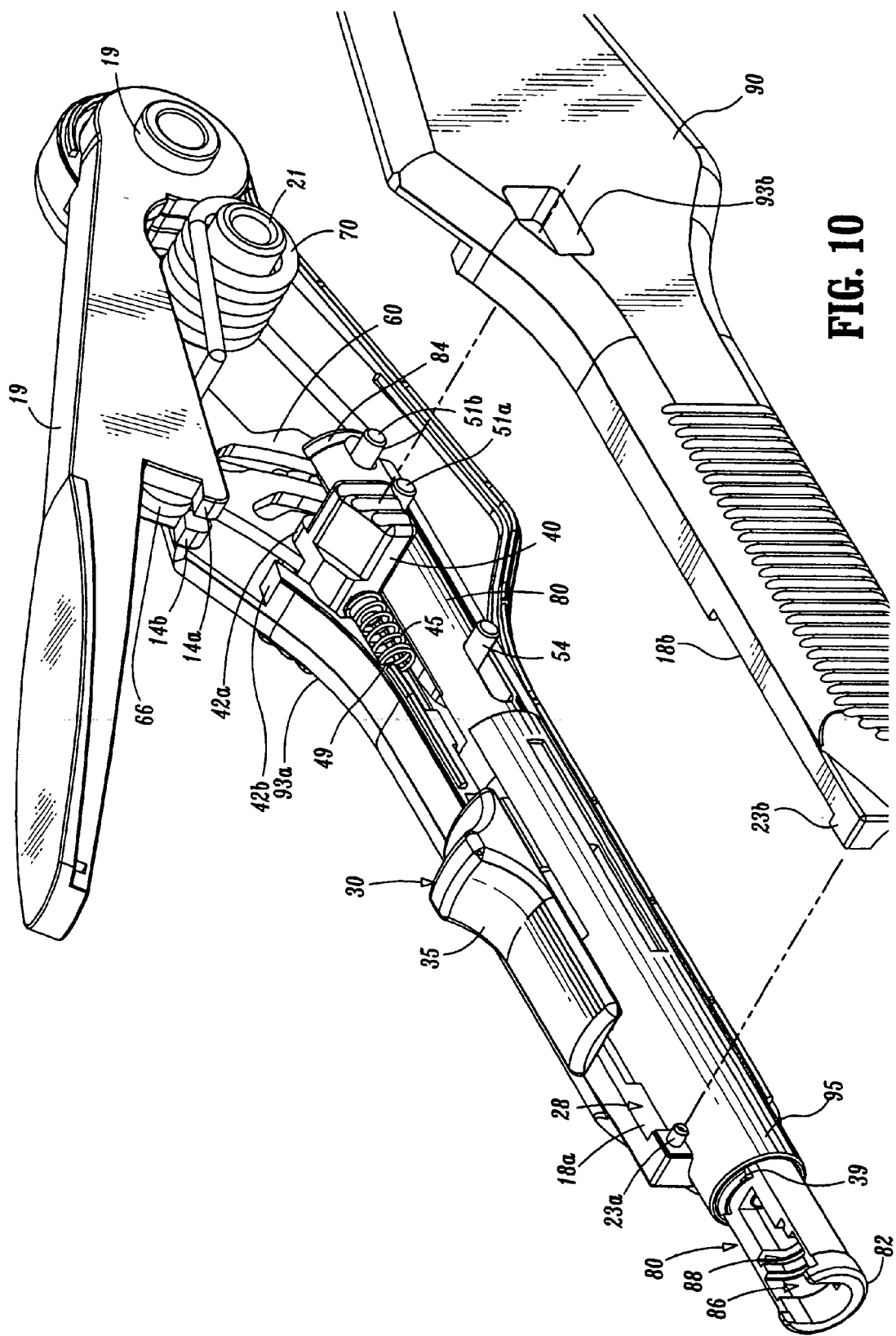
FIG. 10 is a perspective view of the actuator assembly with the cover plate shown separated.

As mentioned above, actuating assembly 20 also includes a spring-loaded thumb tab 30 which rests atop housing 26 within a longitudinally extending slot 28 disposed near the distal end 22 thereof. As best seen in FIG. 10, slot 28 is formed by notches 18a and 18b of the housing 26 and cover plate 90, respectively. Tab 30 includes a thumb guide 35, which cooperates with a sliding sleeve 32 to facilitate proximal movement of the tab 30 for loading the SULU. A downwardly depending flange 34 disposed on tab 30 engages a corresponding slot 33 located in a mount 31 disposed atop the sliding sleeve 32. Preferably, sliding sleeve 32 includes a post 36, which is dimensioned to receive a tension spring 38 thereon. Spring 38 is biased between a block 47 disposed within housing 26 and a proximal edge 37 of sliding sleeve 32 such that spring 38 biases sliding sleeve 32 to a distal-most position proximate distal-end 22. Preferably, a distal end 39 of sleeve 32 is arcuate or semi-circular and is dimensioned to slidingly engage a corresponding end 82 of a first retractor 80 to lock the SULU 100 within the actuator assembly 20 after the SULU 100 is loaded as will be discussed in more detail below.

Actuator assembly 20 also includes first retractor 80 and a second retractor 50 which each move by way of movement of the handle 12, which, in turn, imparts movement to the two-stage cam 60. First retractor 80 includes distal and proximal ends 82 and 84, respectively, and is generally tubular in dimension with the exception of an elongated furrow 83 extending proximally from distal end 82 for slidingly supporting sleeve 32. Retractor 80 also includes a slot 85 for receiving a pin 54 for affixing the retractor 80 to the cam 60 and another pair of slots 87 and 89 located near the proximal end 84 for receiving two cam followers 51a and 51b, respectively. Preferably, the proximal end 84 is bifurcated to facilitate insertion of the second retractor 50 therein.

Figure 16:
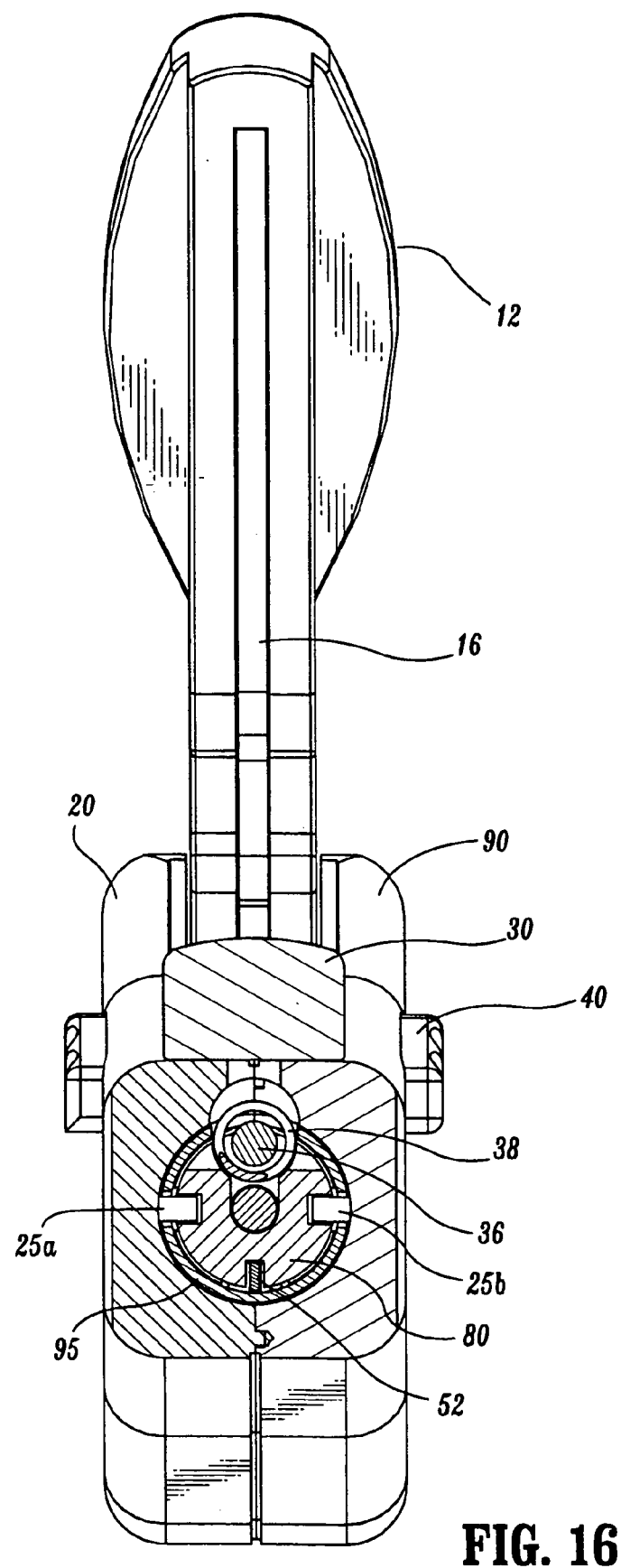
FIG. 16 is a front cross-sectional view of the surgical instrument taken along section line 16-16 of FIG. 12.

As best seen in FIGS. 11 and 16, a guide 81 engages an elongated rib 25a in housing 26 and an elongated rib 25b in cover plate 90 to slidingly mount the retractor 80 to housing 26. Guide 81 is dimensioned slightly longer than rib 25a to permit proximal movement of the first retractor 80 relative to the housing 26 upon activation of the handle 12. Preferably, a protective tube 95 is telescopically disposed about the first retractor 80 and moves in conjunction with the sliding sleeve 32 by way of slot 96 which secures mount 31 of the sliding sleeve 32 therein. It is anticipated that protective tube 95 also helps to restrict lateral movement of the first retractor 80 during retraction. Tube 95 also includes an elongated channel 97 which generally aligns with guide 81 located in the first retractor 80 to mount both components to ribs 25a and 25b.

It is contemplated that proximal movement of tab 30 will impart reciprocating proximal movement to the sliding sleeve 32 to expose carriages 86 and 88 disposed within the first retractor 80 which are designed to receive a pair of first and second retracting sleeves 110 and 120 (FIGS. 7-9) of the SULU 100. More particularly, and as best seen in FIG. 5, carriage 86 is generally circular in shape and is designed to receive an outer lip 122 formed by the union of end 122a and 122b of second retracting sleeve 120 of the SULU 100. Preferably, carriage 86 is dimensioned larger that the lip 122 so as to permit proximal movement of the second retracting sleeve 120 relative to the first retracting sleeve 110 as will be explained in more detail with respect to FIG. 22A. Carriage 88 is likewise circular in shape and receives outer lip 112 of the first retracting sleeve 110.

Figure 12:
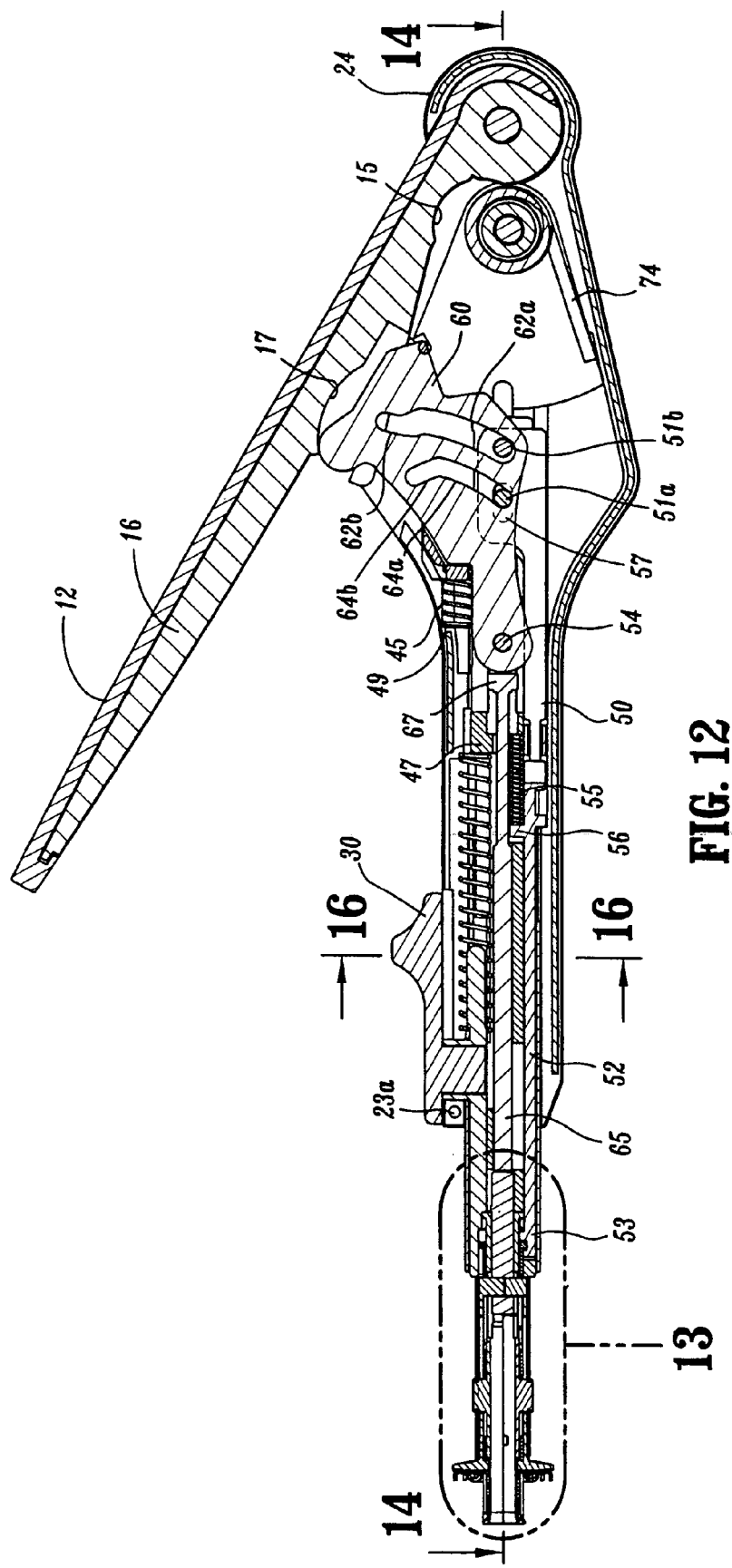
FIG. 12 is a horizontal cross-sectional view of the surgical instrument of FIG. 1 shown loaded for firing.

Actuator assembly 20 also includes a handle lock 40, which rests atop the first retractor 80 and extends laterally between the housing 26 and the cover plate 90. More particularly, handle lock 40 is mounted within slots 93a and 93b as best seen in FIG. 10. Handle lock 40 includes a post 43 which receives a spring 45 for biasing handle lock 40 against a ledge 49 of the housing 26 (FIG. 12). Handle lock 40 also includes a pair of flanges 42a and 42b which align with flanges 14a and 14b disposed on handle 12. As shown best in FIGS. 21 and 22, downward movement of the handle 12 forces the handle lock 40 initially distally against spring 45 until flanges 14a and 14b clear flanges 42a and 42b at which point spring 45 forces handle lock 40 proximally to lock flanges 42a and 42b atop flanges 14a and 14b and to lock handle 12 in a downwardly disposed position. Preferably, flanges 42a and 42b define a slot 41 for receiving lever 16 therebetween.

Actuator assembly 20 also includes a second retractor 50 which includes an elongated arm 52 having a key-like distal end 53 and a T-shaped heel section 56. Preferably, T-shaped heel section 56 attaches to a tension spring 55 disposed proximally thereof. Second retractor 50 is preferably bifurcated at its proximal end forming two longitudinally extending fins 58a and 58b each having a slot 57 and aperture 59 for receiving cam followers 51 and 51b, respectively. It is contemplated that spring 55 is biased against an elongated stop 65 which rests atop arm 52 and biases heel section 56 proximally when the second retractor 50 is retracted which will be explained in more detail below with respect to the operation of the surgical instrument 10.

As mentioned above, the first retractor 80 is affixed to two-stage cam 60 by pin 54. More particularly, cam 60 includes an aperture 61 located near the distal end thereof for receiving pin 54 which affixes the cam 60 to the first retractor 80. Cam 60 also includes a pair of generally vertical arcuately-shaped slots 62 and 64 which each include two discrete stages, namely 62a, 62b and 64a, 64b, respectively, for imparting movement to corresponding followers 51a and 51b. A nub 66 is located near the uppermost portion of the cam 60 and is dimensioned to slideably engage recess 17 located in lever 16 as best illustrated in FIG. 12.

Figure 21:
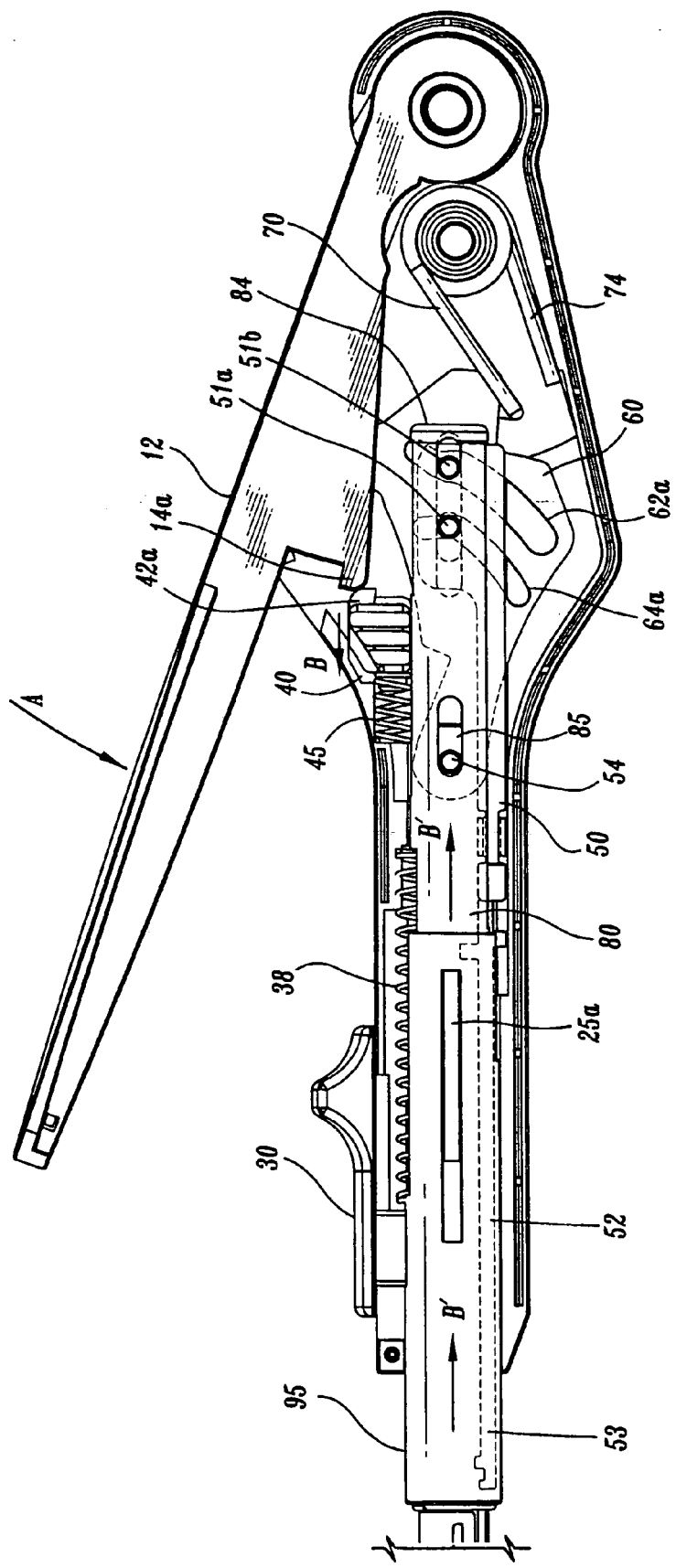
FIG. 21 is a side view of the actuator assembly without the cover plate during a first firing stage of the instrument and showing the internal movement of a first retractor within the actuator assembly.
Figure 21A:
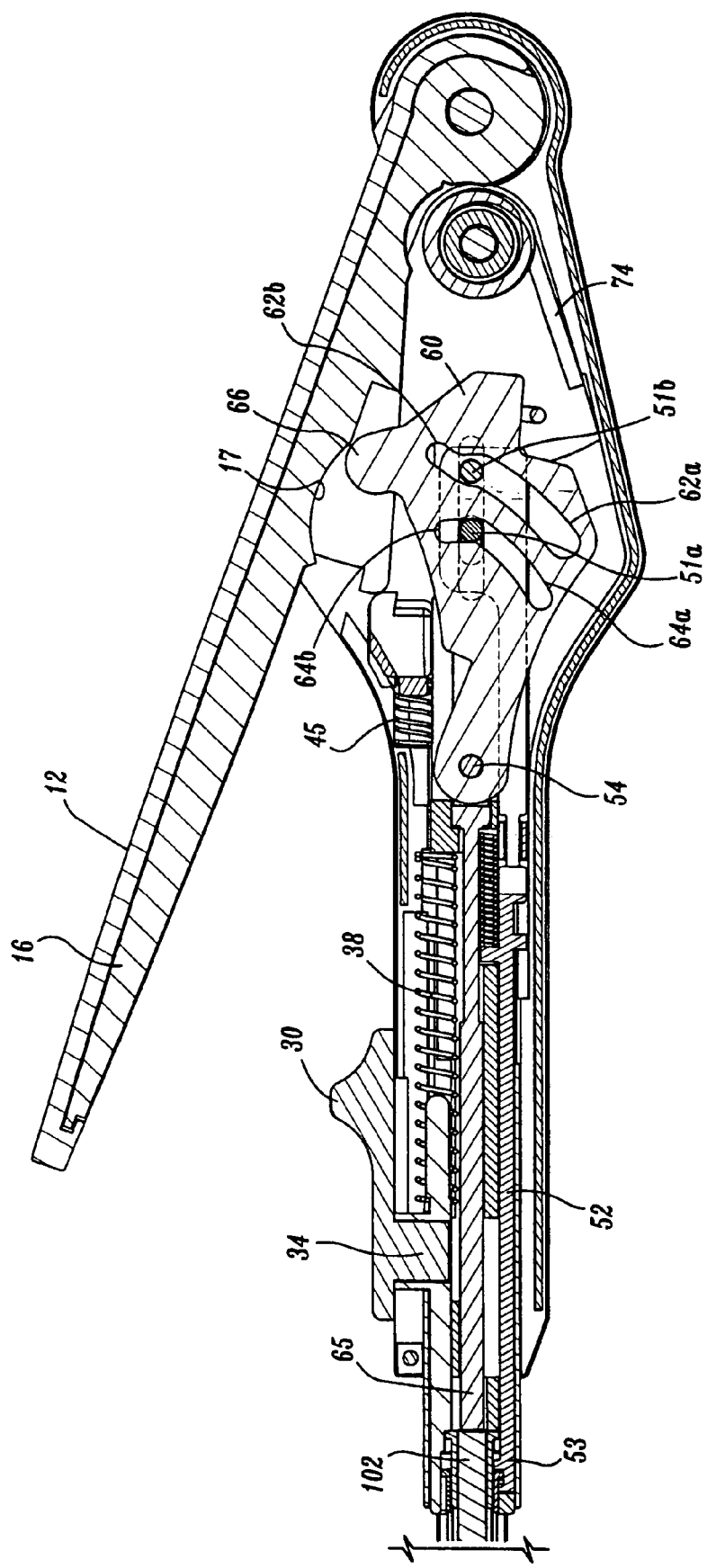
FIG. 21A is a side cross-sectional view showing the relevant positions of the internal working components of the actuator assembly after the first firing stage.
Figure 22:
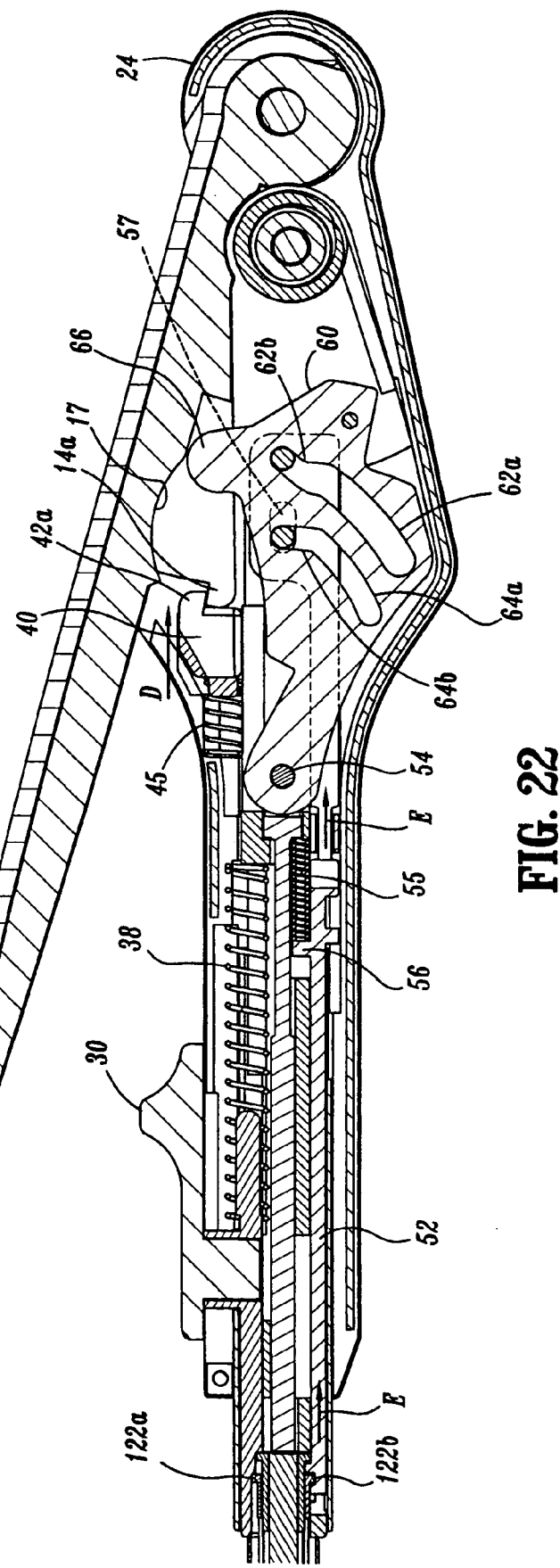
FIG. 22 is a side cross-sectional view of the actuator assembly during the second firing stage and showing the internal movement of a second retractor within the actuator assembly.

It is contemplated that during downward movement of handle 12, lever 16 will bias nub 66 downwardly such that nub 66 rides proximally along recess 17 and causes cam 60 to pivot downwardly about pin 54 as shown best in FIGS. 21A and 22. In turn, followers 51a and 51b will ride along slots 64 and 62 and cause the first and second retractors 80 and 50 to move in a proximal direction which will be explained in more detail below. Preferably, recess 17, nub 66 and slots 64 and 62 can be dimensioned to control the movement and timing of the cam followers 51*a* and 51*b*. For example, it is envisioned that the stages 64*a*, 64*b* and 62*a* and 62*b* can be dimensioned to control the timing and movement of the first and second retractors, which, in turn, can effect the efficiency of the anastomosis.

Elongated stop 65 is preferably affixed to the distal end of cam 60 and rests atop the second retractor 50. Elongated stop 65 includes a distal end 69 and a proximal end 67 which includes two extending portions 67*a* and 67*b* each having an aperture 63*a* and 63*b*, respectively, disposed therethrough. Preferably, end 69 of stop 65 is sufficiently dimensioned such that it engages a corresponding biasing post 102 located within the SULU 100.

Preferably, the second retractor 50, the cam 60 and the elongated stop 65 are pre-assembled prior to insertion into the first retractor 80. More particularly and as best illustrated in FIGS. 10-12, elongated stop 65 is positioned atop arm 52 of the second retractor 50 between T-shaped heel section 56 and end 53. Apertures 63*a* and 63*b* of stop 65 align with aperture 61 of cam 60 such that once the cam 60 and the elongated stop 65 are inserted within slot 91 of the first retractor 80, pin 54 locks the two components 65 and 60 together through slot 85.

Cam 60 is positioned between the extending fins 58*a* and 58*b* of the second retractor 50 such that, when the retractor 50 and cam 60 are inserted within slot 91 of the first retractor, followers 51*a* and 51*b* are inserted through slot 87 and slot 89, respectively, and slideably couple the two components 50 and 60 within the first retractor 80. Handle lock 40 is then positioned atop the first retractor 80 as described above. First retractor 80 is then mounted on ribs 25*a* and 25*b* of housing 26 and cover plate 90, respectively and tab 30 along with sliding sleeve 32 are engaged thereon. Handle 12 and lever 16 are then assembled as described above and pivotably mounted about post 21. Spring 70 is then positioned accordingly so as to bias handle 12 against housing 26.

Turning now to FIGS. 7-9 which show an exploded view of the internal working components of the SULU 100 which as mentioned above includes first retracting sleeve 110 and second retracting sleeve 120 which cooperate to deform fasteners 260 and securely fasten the saphenous vein 320 to the aorta 310 in fluid communication as shown in FIG. 24.

More particularly and as best seen in FIGS. 7-7D, first retracting sleeve 110 includes a tube-like base 110*a* and an arcuate sleeve cap 110*b* which together define the first retracting sleeve 110. Base 110*a* includes a circular lip 112 located at its proximal end and a semi-circular anvil 118*a* located at the opposite end. A locking tab 116*a* having an elongated slit 182*a* located therein is disposed between lip 112 and anvil 118*a*. A longitudinally-extending slot 114*a* is disposed between the lip 112 and the locking tab 116*a*. At least one interface 117*a* downwardly depends from base 110*a* to mechanically engage a corresponding mechanical interface 117*b* disposed on sleeve cap 110*b* (FIG. 7). A flange 113*a* is preferably disposed beneath slot 114*a* and is sufficiently dimensioned to engage corresponding flanges 113*b*$_1$, and 113*b*$_2$ located on sleeve cap 110*b*. Slot 114*a* is sufficiently dimensioned to receive a tab 138*a* (FIG. 13) which projects from an upper surgical fastener support 130*a* which is explained in more detail below.

Figure 17:
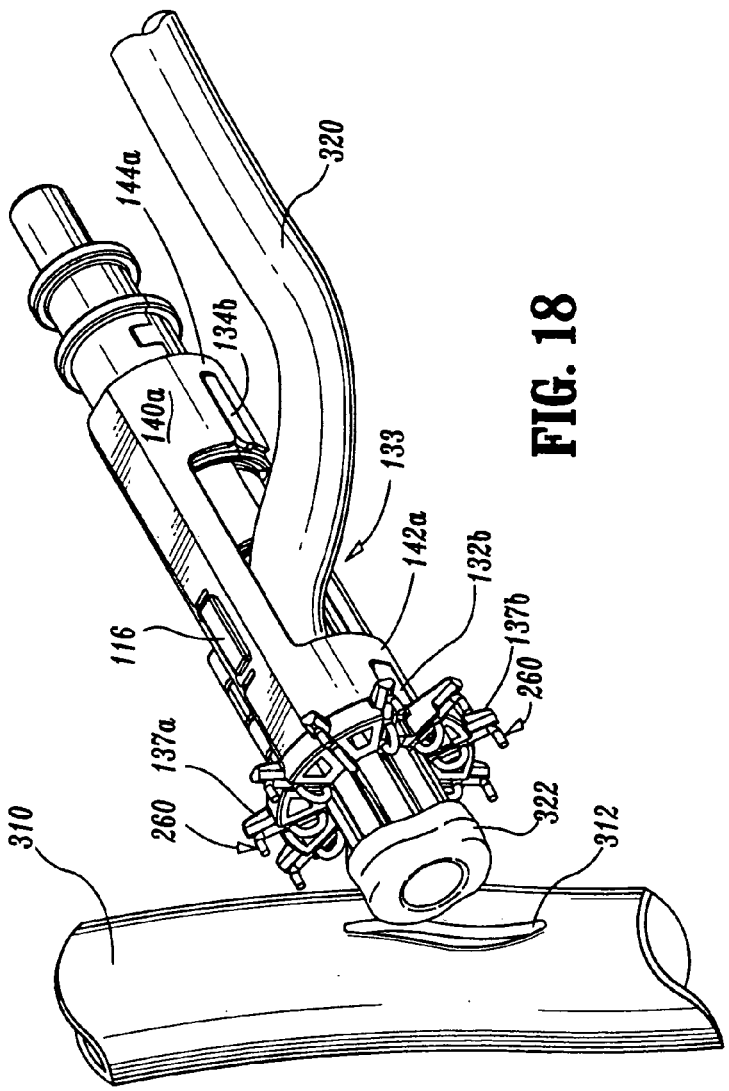
FIG. 17 is a perspective view of the SULU with a first vessel inserted therethrough.

Sleeve cap 110*b* includes a semi-circular anvil 118*b* and a bifurcated proximal end 113 composed of flanges 113*b*$_1$, and 113*b*$_2$ which together define a slot 114*b* for receiving a tab 138*b* which projects from a lower surgical fastener support 130*b* which is explained in more detail below. Sleeve cap 110*b* also includes mechanical interfaces 117*b* which couples with corresponding mechanical interfaces 117*a* disposed on base 110*a* to engage sleeve cap 110*b* with base 110*a*. A locking tab 116*b* having an elongated slit 182*b* located therein is disposed between proximal end 113 and anvil 118*b*. A longitudinally-extending opening 111*b* is preferably disposed proximate locking tab 116*b* and aligns with a corresponding opening 111*a* in base 110*a* (FIG. 7C) such that the saphenous vein 320 can be received therethrough as seen best in FIGS. 17 and 18.

FIGS. 2A and 7D show a greatly enlarged view of anvil 118*a* which includes a semi-annular array of fastener support channels or cradles 119*a* each configured and dimensioned to support a surgical fastener 260 therein. Sleeve cap 110*b* also includes fastener support channels 119*b* which, when base 110*a* and sleeve cap 110*b* are assembled, align to form a circular array about the internal surfaces of anvil 118*a* and 118*b*. It is envisioned that anvils 118*a* and 118*b* can be designed to support different arrays of surgical fasteners 260 depending upon a particular purpose. Each channel 119*a* and 119*b* is preferably separated by an anchor 187*a* and 187*b* (FIG. 7) which releasably retains a projecting finger 124*a*, 124*b* of second retracting sleeve 120 (FIG. 2A). Support channels 119*a* and 119*b* each include proximal ends 186*a* and 186*b* and distal ends 184*a* and 184*b* which are radially offset from one another to seat surgical fastener 260 within channels 119*a* and 119*b* in a radially offset manner the purpose of which will be explained below with respect to the operation of the surgical instrument 10. The distal end 184*a* of each channel 119*a* is preferably arched so as to correspond to the arcuate shape of the end of the surgical fastener 260 as best seen in FIG. 13A. It is anticipated that arching the distal end 184*a* will cause the surgical fastener 260 to deform upwardly and proximally upon retraction of the first retracting sleeve 110 by the first retractor 80 as explained below with reference to FIGS. 21-22.

FIGS. 7-7D also show second retracting sleeve 120 which includes an upper cuff 120*a*, a lower cuff 120*b* and an outer cap 128 which together define the second retracting sleeve 120. More particularly, upper cuff 120*a* includes a semi-annular lip 122*a* at one end and a plurality of retention fingers 124*a* at the opposite end. Upper cuff 120*a* also includes a first slot 101 which preferably aligns with slot 114*a* of the first retracting sleeve 110*a* to receive tab 138*a* of upper fastener support 130*b* therethrough (FIG. 20). A second slot 126*a* receives locking tab 116*a* when cuff 120*a* is slideably mounted atop base 110*a*. Interfaces 129*a* mechanically engage corresponding interfaces 129*b* located on lower cuff 120*b*.

Lower cuff 120*b* includes a bifurcated proximal end 107 which comprises flanges 107*b*$_1$, and 107*b*$_2$ which define a slot 108 for receiving tab 138*b* of lower fastener support 130*b* therethrough and a plurality of retention fingers 124*b* which extend from the opposite end thereof. A slot 126*b* is disposed between the flanges 107*b*$_1$, 107*b*$_2$ and the fingers 124*b* for receiving locking tab 116*b* of the sleeve cap 110*b* when cuff 120*b* is slideably mounted thereon. A longitudinally-extending opening 121*b* is disposed proximate slot 126*b* and aligns with a corresponding opening 121*a* in upper cuff 120*a* and also aligns with openings 111*a* and 111*b* of the first retracting sleeve 110 such that the saphenous vein 320 can be received therethrough as seen best in FIGS. 17 and 18.

A semi-circular cuff cap 128 is disposed atop lower cuff 120*b* and mechanically interfaces with upper cuff 120*a* such that semi-circular lips 122*a* and 122*b* for circular lip 122. More particularly, cuff cap 128 includes a plurality of detents 123*b* which mechanically engage a corresponding plurality of notches 123*a* located in upper cuff 120*a* such that the cuff cap 128, upper cuff 120*a* and lower cuff 120*b* all move in unison upon retraction of the second retracting sleeve 120. Sleeve cap 128 is preferably bifurcated at its distal end forming slot 109, which is dimensioned to receive tab 138b.

As can be appreciated, fingers 124a and 124b move upon retraction of the second retracting sleeve 120 to release the surgical fasteners 260 after firing. More particularly and as best seen in FIGS. 2A and 7A, the distal end of each finger 124a is forked and includes a first prong 127a which retains a surgical fastener 260 within the fastener support channels 119a and a second prong 125a which interlocks with anchor 187a to releasably lock the finger 124a to the first retracting sleeve 110 until released by the second retractor 50 (FIGS. 22A and 22B) which will be explained in more detail with respect to the operation of the surgical instrument 10. Likewise, each finger 124b of lower cuff 120b includes prongs 127b and 125b which operates in the same manner.

As mentioned previously, the SULU 100 also includes fastener support 130 which has an upper support 130a and a lower support 130b which, when assembled, internally house the first and second retracting sleeves 110 and 120, respectively, along with their individual working components. Upper support 130a and lower support 130b each include a distal end 135a and 135b each having an array of braces 137a and 137b, respectively, which project radially from distal ends 135a and 135b. As best illustrated in FIG. 2, each brace 137a and 137b supports an upwardly extending support leg 262 of a surgical fastener 260 disposed within one of the channels 119a or 119b. A plurality of radially extending slots 139a and 139b are disposed between each support brace 137a, 137b for retaining a surgical fastener 260 therein and for restricting unwanted lateral movement of each fastener 260. It is anticipated that each surgical fastener 260 is positioned within a slot 139a, 139b such that convexity 263 projects outwardly from brace 137a, 137b and, after anastomosis, cooperates with the base leg 264 to retain the saphenous vein 320 against LAD and/or aorta 310 (FIGS. 21B and 24).

Upper support and lower support 130a and 130b, respectively, also include hinges 136a and 136b which, when the SULU 100 is assembled, matingly engage one another to allow pivotable movement between the supports 130a and 130b from an open position (FIG. 23) to a closed position (FIG. 2). Preferably, a pin 180 secures the two hinges 136a and 136b together (FIG. 6). Upper and lower supports 130a and 130b each include a longitudinally-extending opening 133a (FIG. 23) and 133b which aligns with openings 121a, 121b, 111a and 111b described above to receive saphenous vein. 320 therethrough as seen best in FIGS. 17 and 18. Longitudinally oriented slots 131a and 131b are disposed adjacent openings 133a and 133b on the upper and lower support members 130a and 130b, respectively, for receiving locking tabs 116a and 116b in much the same manner as described above with respect to slots 126a and 126b of the second retracting sleeve 120.

Lower support 130b includes a pair of shoulders 132a and 132b disposed on opposite sides of opening 133b for slideably receiving a corresponding pair of flanges 144a and 144b associated with an upper locking sleeve 140a. More particularly, each flange 144a and 144b extends distally from the upper locking sleeve 140a to define a notch 149a and 149b, respectively, therein for receiving shoulders 132a and 132b of lower support 130b.

Figure 21E:
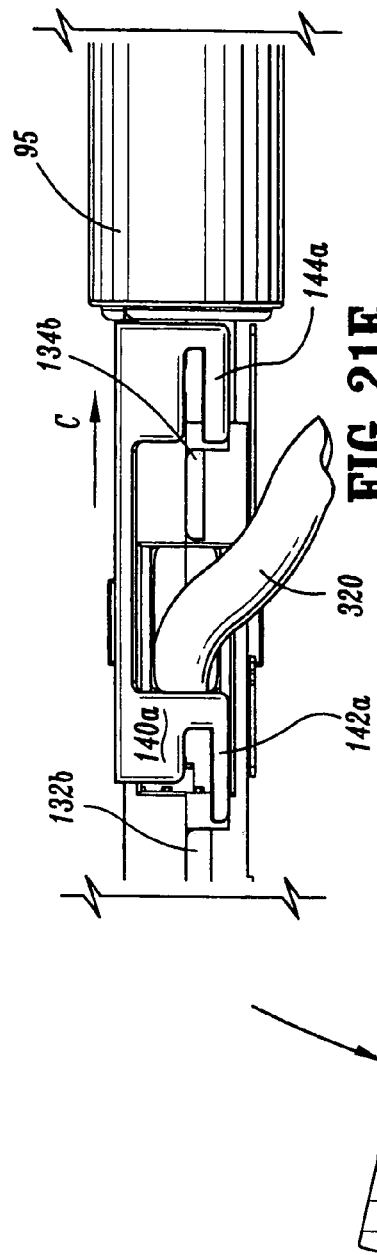
FIG. 21E is a side view showing the relevant movement of a locking sleeve after the first firing stage.

Upper locking sleeve 140a includes a C-shaped clip 146a (FIG. 8) disposed therein which has pair of opposing hooks 147a for snap-lockingly engaging slit 182a of locking tab 116a of first retracting sleeve 110. A lower locking sleeve 140b operates in a similar manner and includes a pair of opposing hooks 147b for snap-lockingly engaging slit 182b of locking tab 116b of first retracting sleeve 110. Upper locking sleeve 140a also includes an opening 141a which aligns with openings 133a, 133b, 121a, 121b, 111a and 111b described above to receive saphenous vein 320 therethrough as seen best in FIGS. 17 and 18. It is envisioned that upon retraction of the second retracting sleeve 120, upper locking sleeve 140a will move proximally relative to shoulders 132b and 134b and disengage shoulders 132a, 132bwhich, in turn, will allow the upper and lower supports 130a and 130b to pivot about pin 180 and release the saphenous vein 320 (FIGS. 21E and 23). This will be explained in greater detail with respect to the operation of the instrument as described below.

SULU 100 also includes a biasing post 102, which mechanically aligns upper and lower supports 130a and 130b in fixed relation relative to one another. More particularly, biasing post 102 includes a proximal end 103 and a distal end 105 and has a vertically oriented cavity 106 disposed therethrough for receiving tabs 138a and 138b of the upper and lower supports 130a and 130b, respectively. As mentioned above, tabs 138a and 138b pass through slots 114a, 114b of the first retracting sleeve 110 and through slots 101, 108 and 109 of the second retracting sleeve 120 and mechanically align with one another within cavity 106 as best seen in FIG. 21B.

Figure 22A:
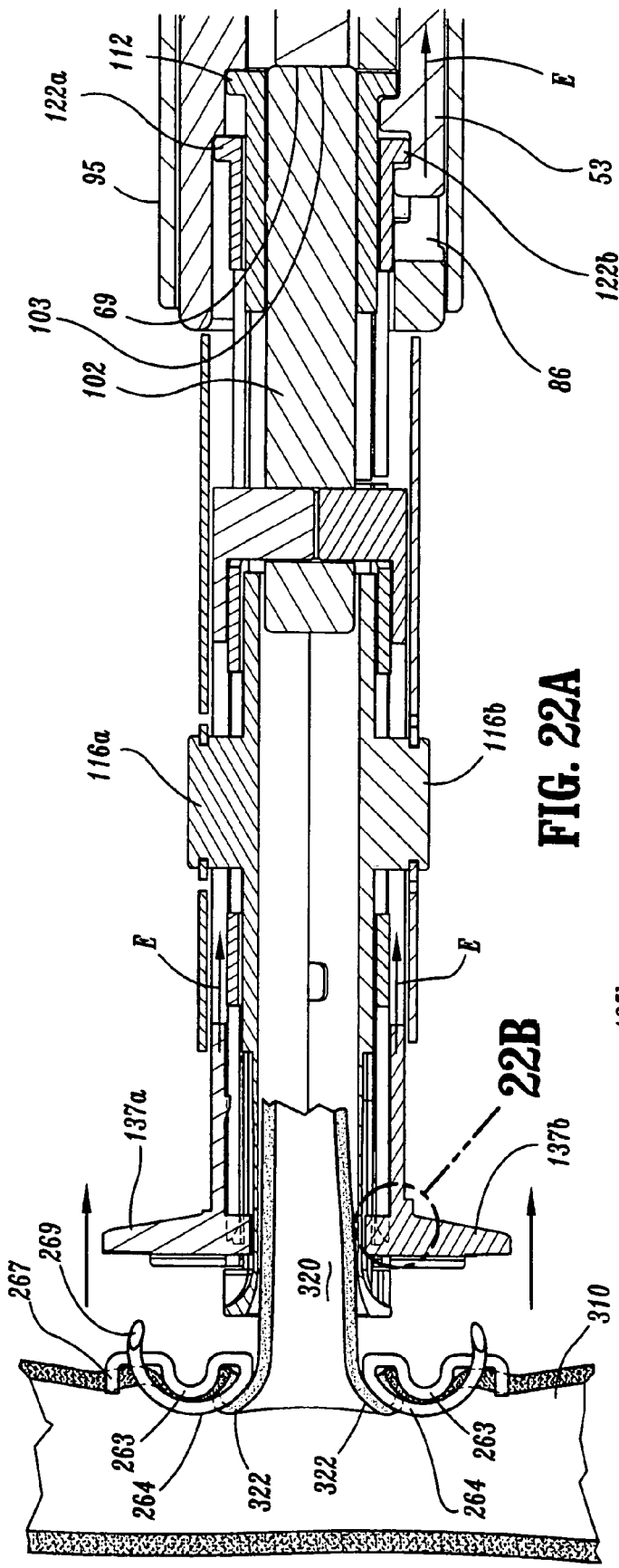
FIG. 22A is a side cross-sectional view of the SULU during the second firing stage and showing the movement of a second retracting sleeve which moves as a direct result of the movement of the second retractor to release the surgical fasteners.
Figure 22B:
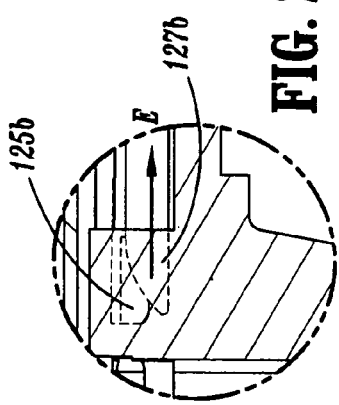
FIG. 22B is a greatly enlarged side cross-sectional view showing the retracting movement of a finger-like retention prong which moves as a direct result of the movement of the second retractor.

Biasing post 102 also includes a tapered spacer 104 disposed along the outer periphery thereof for frictionally locking the first retracting sleeve 110 in a retracted position after the first retracting sleeve 110 is withdrawn by the first retractor 80. More particularly, when the SULU 100 is assembled and prior to firing the surgical instrument 10, biasing post 102 is disposed relative to the first retracting sleeve 110 such that spacer 104 is proximal to lip 112 (FIG. 13). During retraction of the first retracting sleeve 110, lip 112 is forced over spacer 104 and the first retracting sleeve 110 is locked into retracted position and prevented from recoiling. As explained in greater detail below, locking the first retracting sleeve 110 in a retracted position also pre-disposes the second retracting sleeve 120 for retraction relative to the first retracting sleeve (FIG. 22A).

FIGS. 7E-7I show one embodiment of a retaining ring or strap 500 which is designed for use in connection with the SULU 100. It is envisioned that the retaining ring 500 will maintain a consistent anastomosis between the two luminal vessels 310 and 320 after the SULU 100 is fired and the surgical fasteners 260 are released.

Figure 7E:
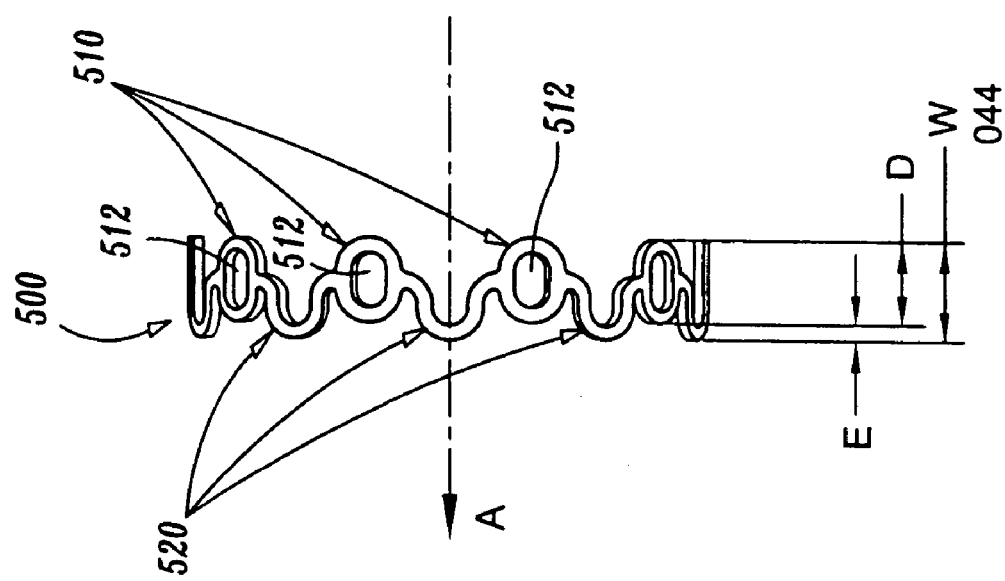
FIG. 7E is an enlarged view of a retaining ring, which may be incorporated with the SULU to maintain a vascular anastomosis between the two luminal vessels.

More particularly and as best shown in FIG. 7E, the retaining ring 500 is preferably constructed from a thin sheet-like, semi-pliable material which is biologically compatible with the various luminal vessels. Retaining ring 500 is generally circular in shape but may be dimensioned in other shapes depending upon the particular configuration of the surgical fasteners 260 when positioned in the SULU 100, e.g., ovoid. Retaining ring 500 includes a series of alternating loops 510 and arcuate portions 520, which are, formed radially about an axis "A" extending through ring 500. Each loop 510 defines an aperture 512 therein which is dimensioned to receive the distal end 269 of a surgical fastener 260.

It is envisioned that the overall width "W" of the retaining ring 500 is dependent upon both the radial dimensions of a major diameter "D" of the loops 510 and the distance "E" which the arcuate portions 520 extend beyond the diameter of the loops 510. It is envisioned that either of these dimensions "D" and/or "E" may be varied to alter the overall width "W" of the ring 500 depending upon a specific purpose.

As best shown in FIG. 7F, retaining ring 500 is positioned over the anvils 118a, 118b of SULU 100 such that the distal end 269 of each surgical fastener 260 is positioned through a respective aperture 512 of loop 510 and an arcuate portion 520 is positioned between each surgical fastener 260. It is envisioned that the ring 500 is held in light friction fit or tensile engagement with the surgical fasteners 260 to prevent inadvertent slippage prior to firing of the SULU 100.

Figure 7G:
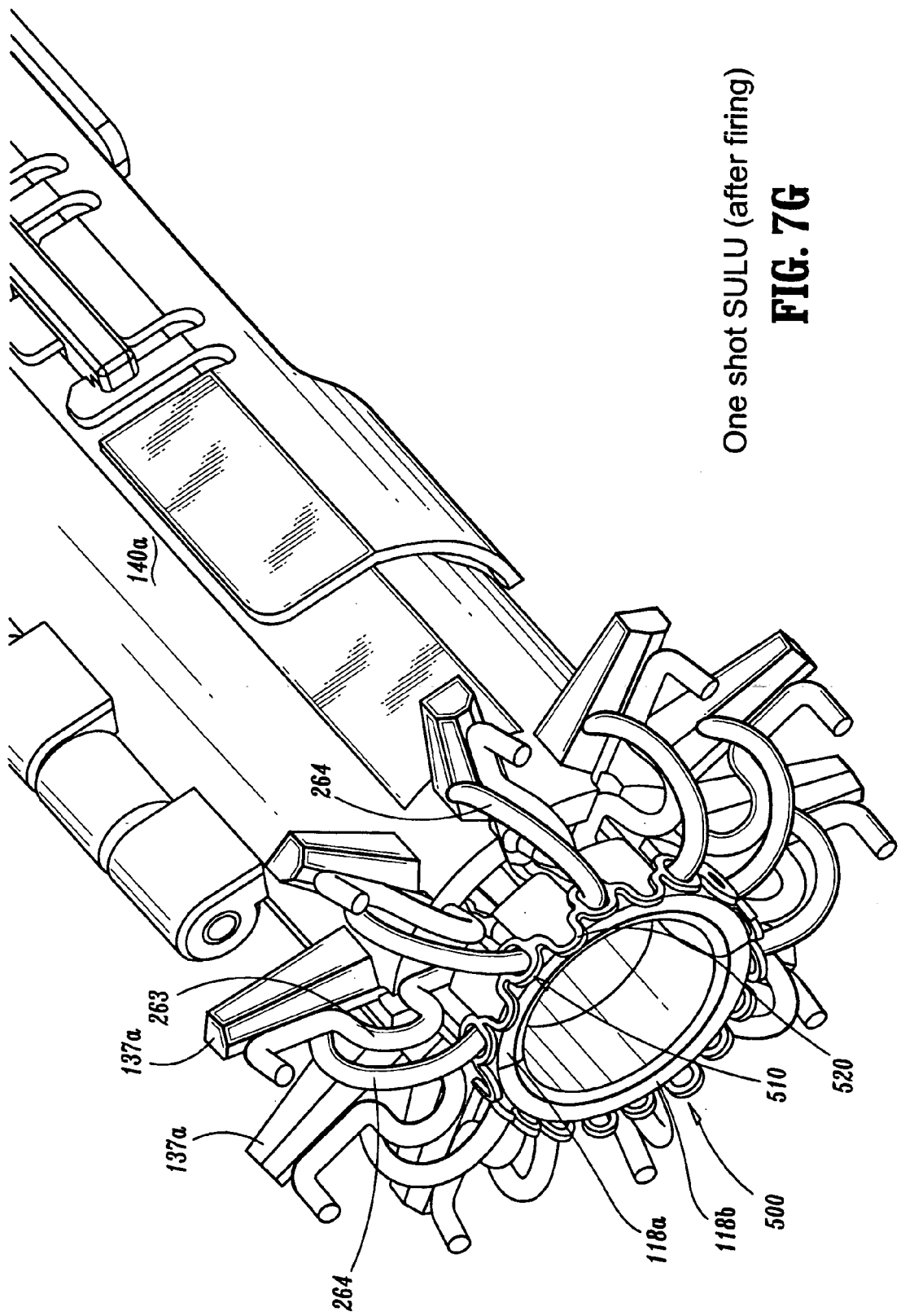
FIG. 7G is an enlarged, partial perspective view of the SULU of FIG. 2 with the retaining ring of FIG. 7E positioned about the surgical fastener after firing the SULU.
Figure 7H:
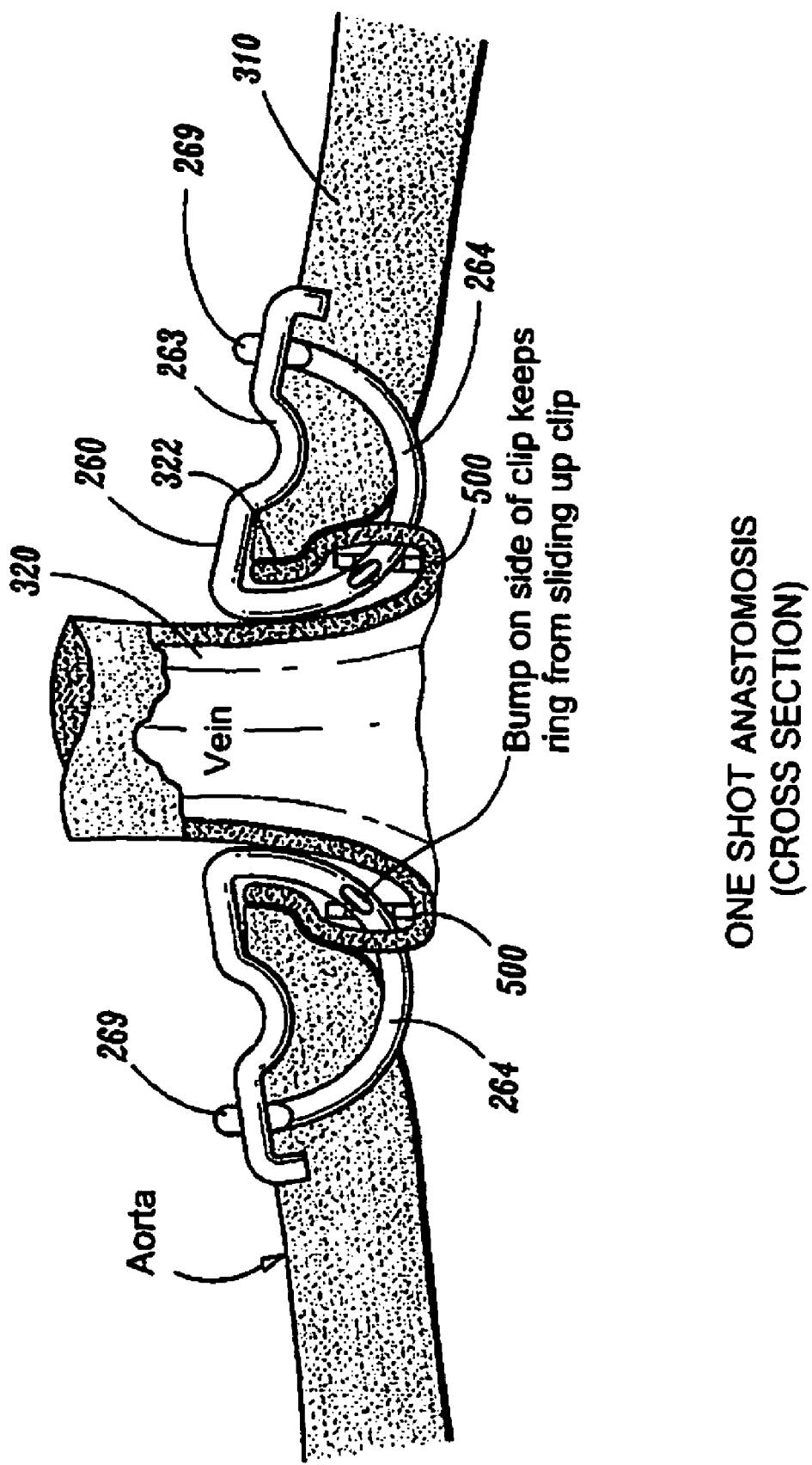
FIG. 7H is cross section of the two luminal vessels showing the position of the retaining ring of FIG. 7E relative to a surgical fastener after firing the SULU.

FIGS. 7G and 7H show the position of the ring and the surgical fasteners after firing the SULU 100. As can be appreciated and as explained in more detail below (i.e., with respect to loading the instrument 10, the everting of vein 320 over the anvils 118a, 118b and the firing of the instrument 10), when fired, the distal ends 269 of the surgical fasteners 260 are forced rearward towards the proximal end of the SULU 100. Simultaneously during deformation, the distal ends 269 are forced through the apertures 512 such that the distal ends 269 pierce vein 320 thereby securing the vein 320 between the ring 500 and the distal end 269 of the surgical fastener 260 (See FIG. 7H). It is envisioned that the pivot point 265 may also be dimensioned to include a relief or coined section 261 which may facilitate formation of the surgical fastener 260 (See FIGS. 7N and 7S).

As can be appreciated, the ring 500 prevents the vein 320 from slipping along the base leg 264 of the fastener 260. More particularly and as best seen in FIG. 7H, the arcuate portions 520 which, as mentioned above, extend beyond the loops 510, abut the outer surface of the vein 320 and prevent the ring 500 from moving along base leg 264 of fastener 260. The inner periphery of the aperture 512 may also be coated with a friction-like material, which also limits slippage of the rings 500 against the base leg 264 which, as a result, also prevents the vein 320 from sliding. As best illustrated in FIGS. 7N-7S, it is also envisioned that fastener 260 may be manufactured to include a protuberance 268 which extends beyond the outer surface of base leg 264. Preferably, protuberance 268 is dimensioned to engage and/or abut against the ring 500 to prevent the ring 500 from sliding along the base leg 264 of fastener 260. Alternatively, the fastener 260 may be dimensioned to include a coined surface (not shown) along base leg 264, which will also prevent the ring 500 from sliding.

Figure 7I:
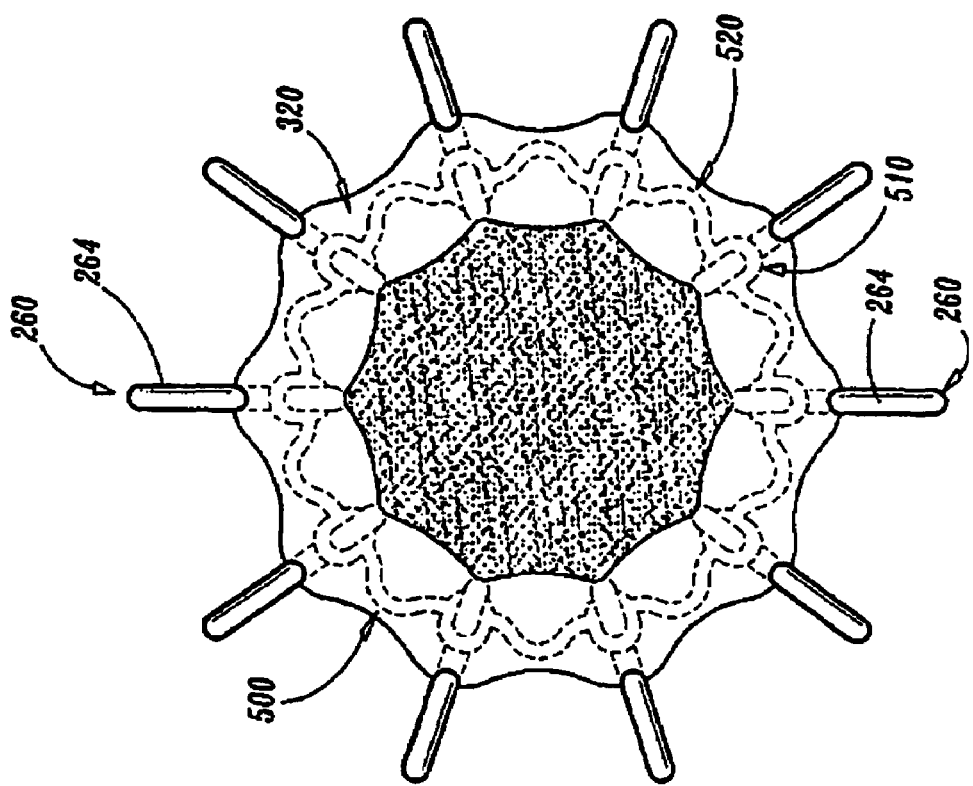
FIG. 7I is an enlarged, internal view of the two luminal vessels showing the position of the retaining ring of FIG. 7E relative to a surgical fastener after firing the SULU.
Figure 7N:
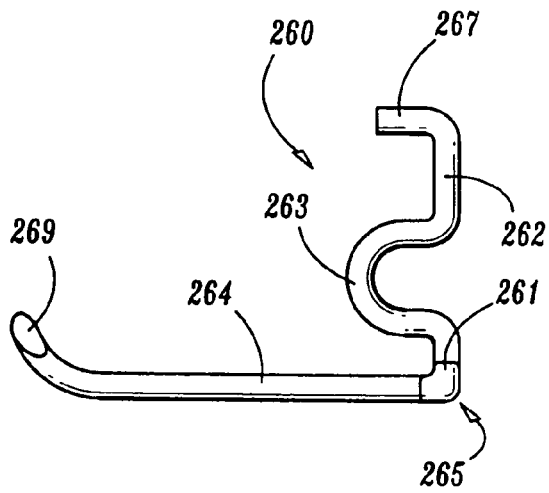
FIG. 7N-7S shows an alternate embodiment of the surgical fastener of FIG. 3 having a protuberance extending from a base leg thereof.
Figure 7O:
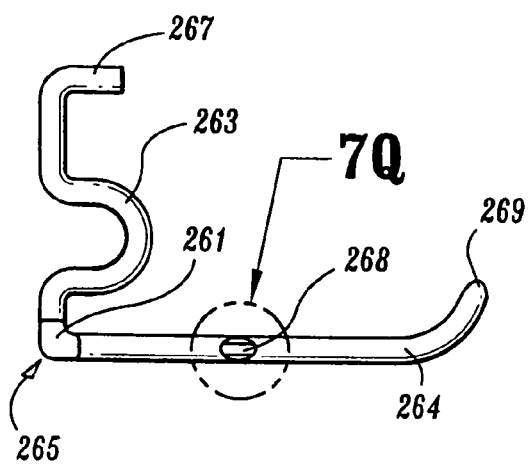
Figure 7P:
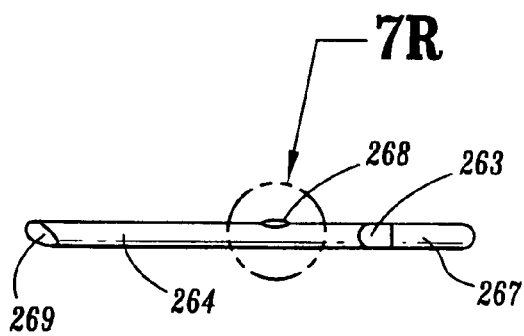
Figure 7Q:
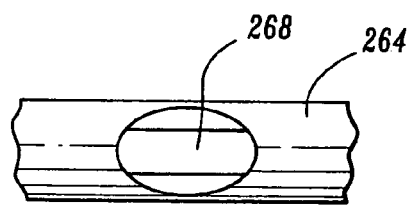
Figure 7R:
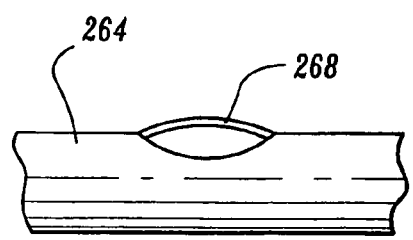
Figure 7S:
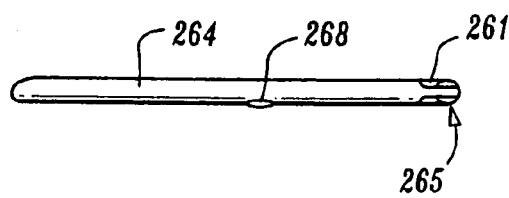

As can be appreciated, preventing the slippage of the vein 320 along fastener 260 will maintain a reliable and consistent anastomosis between the luminal vessels 310 and 320 as best shown by the internal view of FIG. 7I.

FIGS. 7J and 7K show an alternate embodiment of a retainer ring 600 in accordance with the present disclosure. More particularly, retaining ring 600 includes many of the features of retaining ring 500, i.e., alternating loops 610 and arcuate portions 620 and apertures 612 associated with each loop 610, with the exception that ring 600 includes a slit 614 disposed along the inner periphery of aperture 612. It is envisioned that slit 614 will permit the ring 600 to wedge against the base leg 264 of surgical fastener 260 after firing of the SULU 100. As can be appreciated, this will also prevent the vein 320 from sliding.

FIGS. 7L and 7M show other alternate embodiments of retaining rings. More particularly, FIG. 7L shows an alternate embodiment of a retaining ring 650 which includes arcuate portions which straighten after the SULU 100 is fired. It is envisioned that straightening the ring 650 expands the overall radial dimensions of the ring 650 and, as such, holds the loops 660 in friction-fit engagement against the base leg 264 of the surgical fasteners 260 after the SULU 100 is fired. FIG. 7M shows another embodiment of the retaining ring 680 fabricated from a thin wire-like material.

Turning now in detail to the loading of the SULU 100 within actuator assembly 20 as best seen in FIG. 5, thumb tab 30 is moved proximally by way of thumb guide 35 against spring 38 which, in turn, moves sleeve 32 and protective cover 95 proximally to expose carriages 86 and 88. The SULU 100 is then loaded within actuator assembly 20 by placing lip 112 within carriage 88 and lip 122 within carriage 86. As best shown in FIG. 13, lip 122 is positioned near the distal end of carriage 86 which allows lip 122 and, hence, second retracting sleeve 120, to move independently from the first retracting sleeve upon activation of the second retractor 50. In contrast, carriage 88 is dimensioned smaller than carriage 86 such that lip 112 fits snugly within carriage 88. Once the SULU is positioned within carriages 86 and 88, thumb tab 30 is released and spring 38 biases sleeve 32 and protective cover 95 distally over lips 112 and 122 to lock the SULU 100 within the actuator assembly 20.

FIGS. 33-37B shown another embodiment of the surgical instrument according to the present disclosure and is generally referred to herein as surgical instrument 1000. More particularly, surgical instrument 1000 essentially operates along the same or similar principals as surgical instrument 100 in which like reference numerals identify similar or identical elements with the exception that instrument 1000 is generally designed to operate in a more ergonomic fashion. Other features are also evident. The major difference between handle 12 of the previously described embodiment shown in FIG. 1 and handle 1012 shown in FIGS. 33-37B is the reduced firing or activation force required for activation of the instrument. More particularly, the lower firing force is achieved by using an alternative link mechanism 1060 (in lieu of the rotating cam mechanism 60) which reduces the overall firing or actuating force. Link mechanism 1060 includes links 1061, 1062 and 1063 which cooperate with springs 1055 to both deform the surgical fasteners 260 and release the fasteners after deformation as explained in more detail below. In view thereof, handle 1012 may be dimensioned smaller and lighter in weight than the handle 12 of instrument 10.

As shown, handle 1012 is preferably dimensioned as a two-part handle which facilities use and handling of the handle for the user. More particularly, handle 1012a pivots about pivot 1019 from a first pre-firing position or open position to a second closed or flush position with housing 1090 (or two part housing 1090a and 1090b of FIGS. 37A and 37B). As can be appreciated, this is the firing motion of the instrument 1000. A lower handle 1012b is preferably positioned on an opposite end of the housing 1090 and includes a finger rest 1013 to facilitate handling and use of the instrument 1000.

The enhanced ergonomic features of instrument 1000 are different from instrument 10 as well. More particularly, the inclusion of gripping surfaces, e.g., gripping ribs 1021 (FIG. 33), hand rest 1023 (FIG. 33) and finger rests 1013 and 1027 (FIG. 34), can be disposed at various positions along the housing 1090 to facilitate handling of the instrument 1000. Moreover, these gripping areas (ribs 1021, hand rest 1023 and finger rests 1013 and 1027) also provides the user with an enhanced ergonomic "feel" when firing the instrument. For example, once inserted in the aortotomy, the instrument may be handled along the various gripping surfaces with either hand to facilitate activation of the handle 1012.

It is envisioned that housing 1090 may be designed to include other ergonomically advantageous features or designs to improve handling, use and/or aesthetic appeal of instrument 1000, e.g., spline-like shapes, gripping pads, hand rests, additional finger rests, etc. Other features may also be incorporated on the handle 1012a, 1012b to stabilize the instrument during firing, e.g., flanges 1011 and/finger rest 1027.

Figure 33:
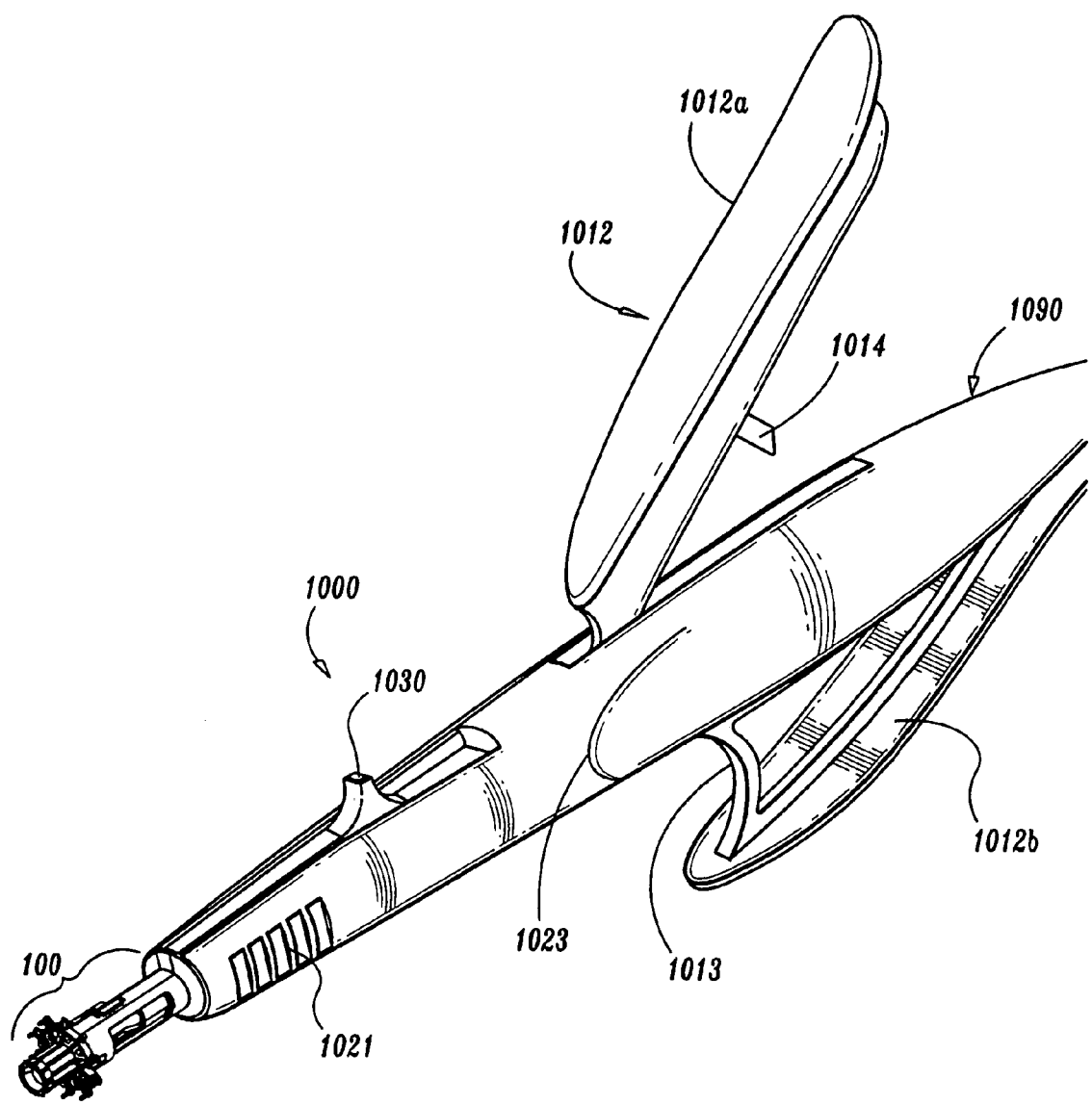
Figure 34:
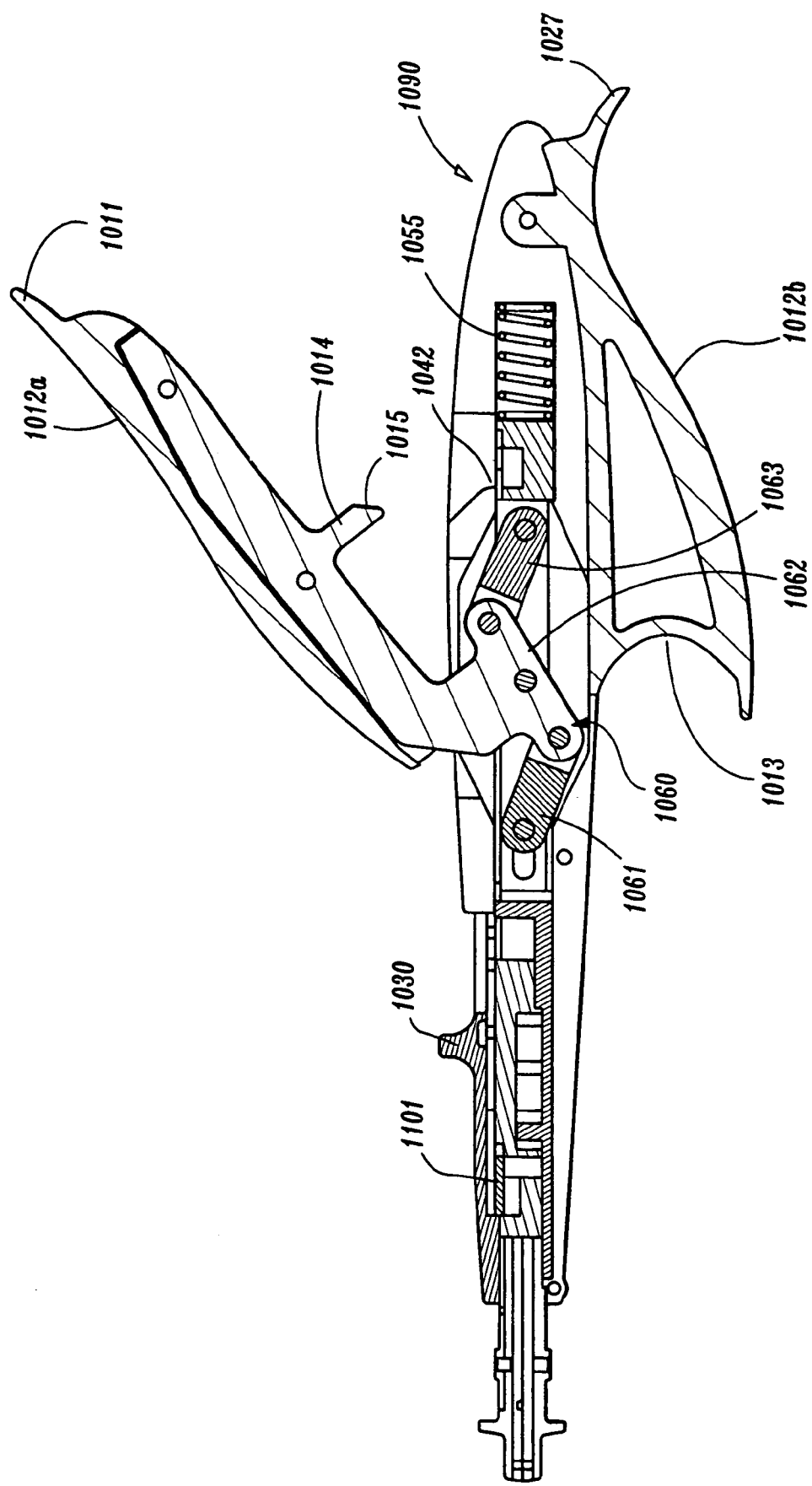
Figure 35:
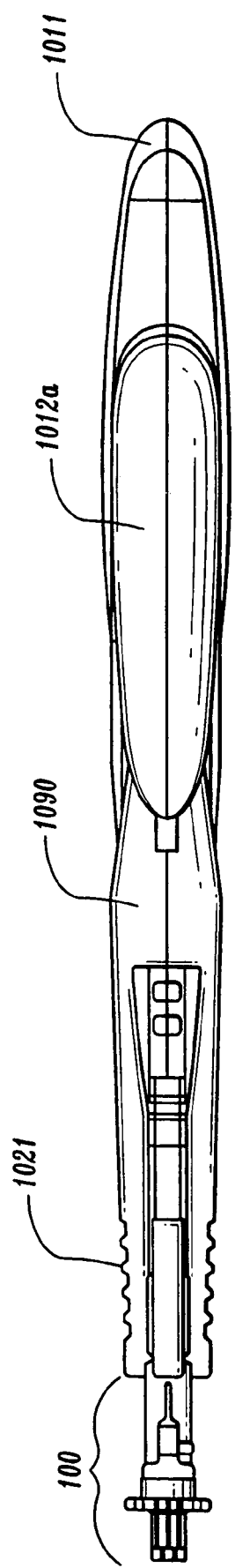

As best shown in FIGS. 33-35, a protruding tab 1014 on the underside of handle 1012a operates in a similar fashion to locking flange 14 of instrument 10. More particularly, tab 1014 engages a corresponding mechanical interface 1042 disposed in the housing 1090. The initial downward movement of the handle 1012a pivots the link mechanism about pivot 1019, which causes deformation of the fasteners 260 in a similar manner as described above with respect to instrument 10. More particularly, when link mechanism 1060 pivots about link 1019, the assembly of links 1061, 1062 and 1063 rotate to a generally horizontal straightened or fully-extended position which causes both deformation of the surgical fasteners 260 (in the same or generally similar manner as described above with respect to instrument 10) and compression of spring 1055.

Continued downward movement of handle 1012a causes links 1061 and 1063 to deflect from the horizontal straightened or fully-extended position which unbiases the spring 1055 which, in turn, causes the release of the surgical fasteners 260 in a similar manner as described above with respect to instrument 10. The movement of tab 1014 controls the movement of the link 1060 in a similar manner as the second stage of cam 60, i.e., to bias a spring 1055 and release the fasteners 260 during movement of the handle 1012a toward the end of the firing stroke. More particularly, the angled face 1015 of the tab 1014 cams a slide 1042 backwards which cooperates with the SULU 100 to release the fasteners 260 after firing.

A spring-loaded lockout mechanism 1101 may be included as is best shown in FIG. 34. The lockout 1101 is preferably disposed within the housing 1090 to prevent the handle 1012a from being actuated if the thumb tab 1030 is not fully forward, i.e., the SULU 100 is not locked onto the instrument 1000 for firing. As can be appreciated, this prevents accidental firing of the handle 1012 if the SULU 100 is not properly seated on housing 1090.

Figure 37A:
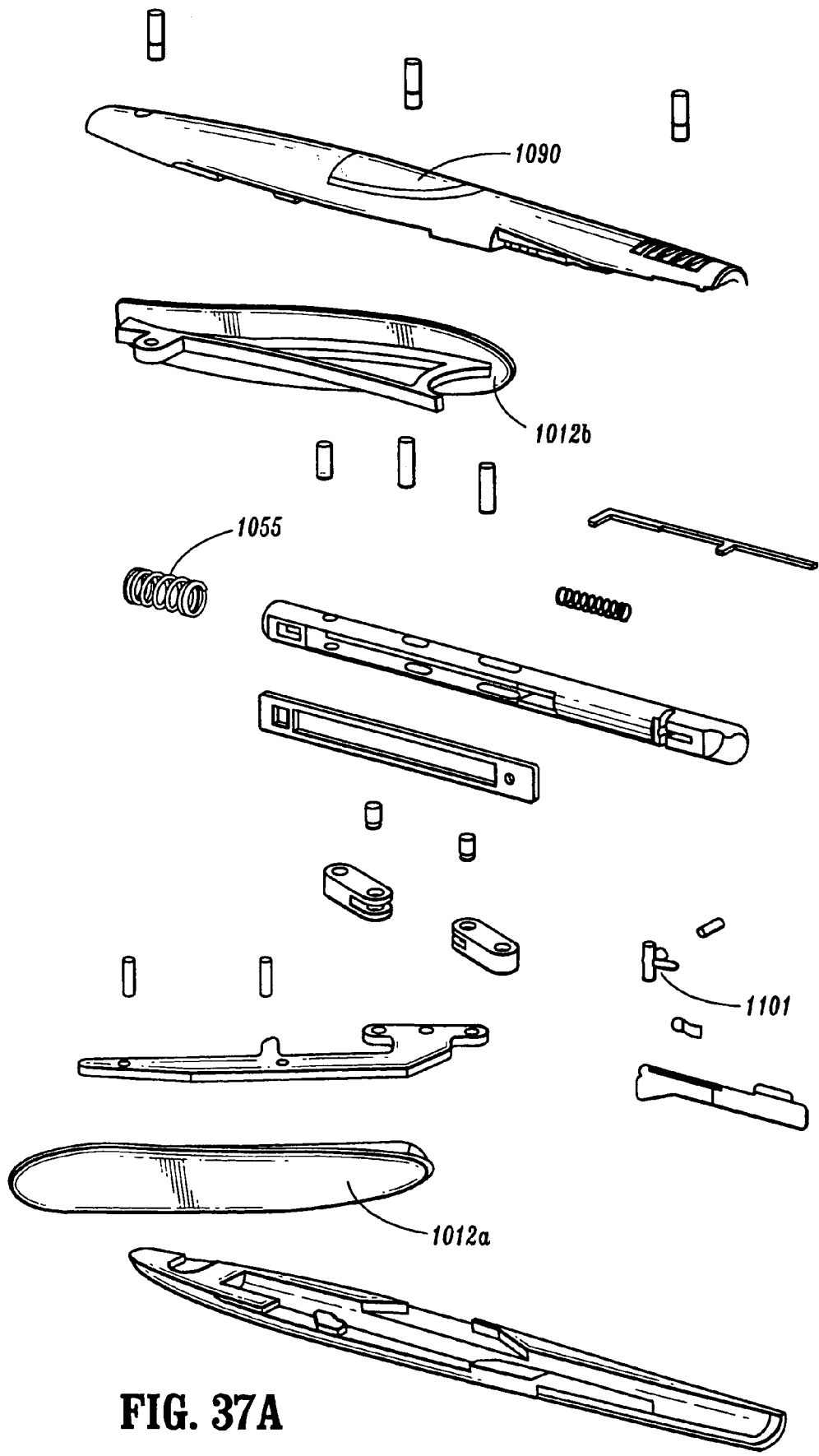
Figure 37B:
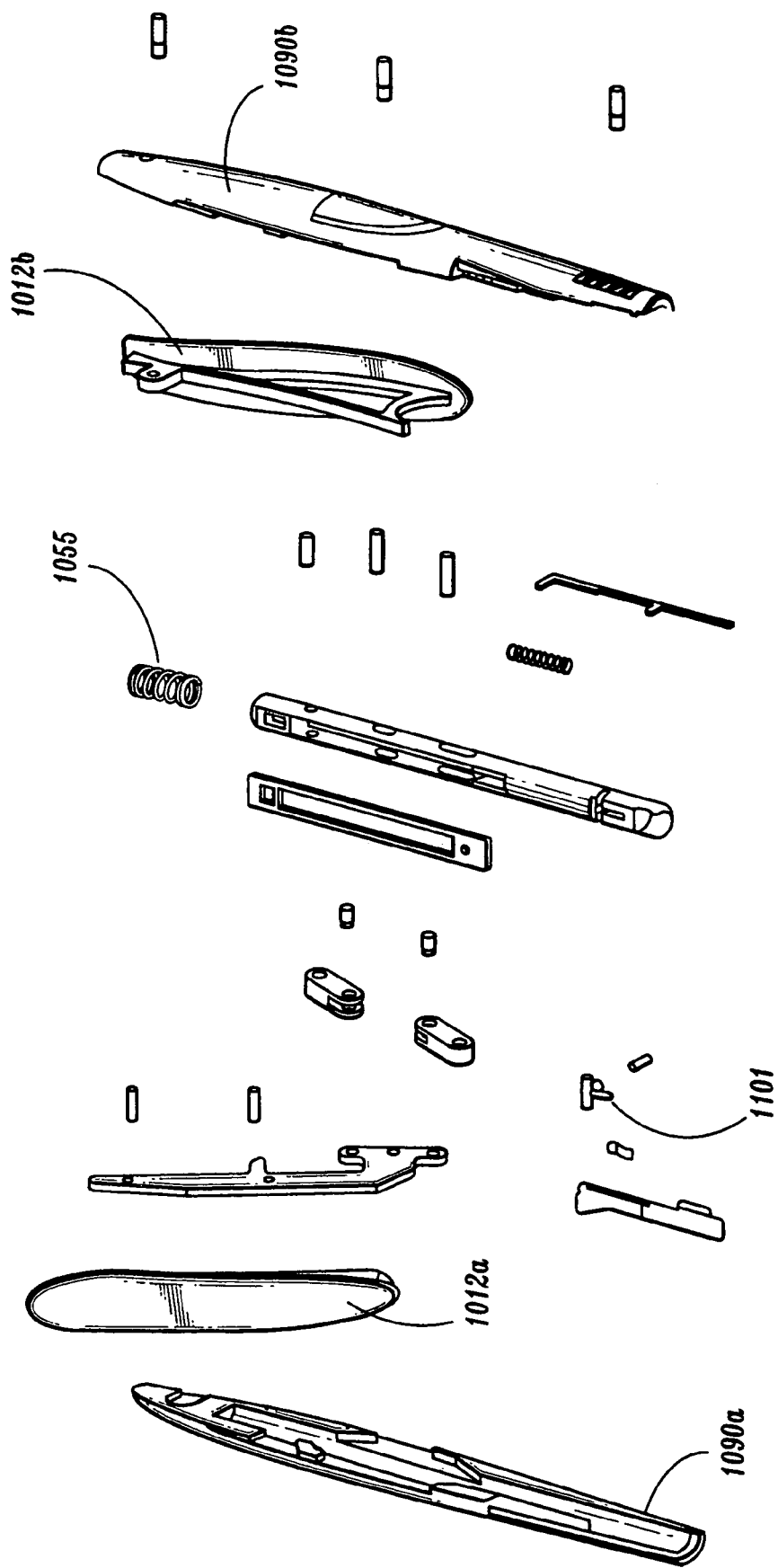

FIGS. 36A and 36B show a front perspective view of the SULU 100 when loaded onto the instrument 1000. FIGS. 37A and 37B show an exploded view of the internal working components of the housing 1090 of the instrument 1000.

In use and as shown in FIGS. 17-24, surgical instrument 10 (or instrument 1000 as shown in FIGS. 33-37B as described above) facilitates the performance of a vascular anastomosis and either eliminates and/or minimizes the need for manual suturing of the vessels. The method and usage described herein will be addressed in terms of vascular anastomosis performed on a beating heart. However, the presently disclosed surgical instrument 10 may also be used in performing anastomoses of other tubular or luminal body structures without departing from the scope of the present disclosure. For example, surgical instrument 10 may be used in conventional open CABG procedures using a median sternotomy or other large incision without stopping the heart. Alternatively, the thoracic "window" procedure may be used to achieve access to the heart. The "window" approach involves a smaller incision and less displacement of the ribs, and therefore is less traumatic to the patient. For this approach, conventional surgical techniques are used to determine the location of the incision to access the chest cavity.

Figure 25:
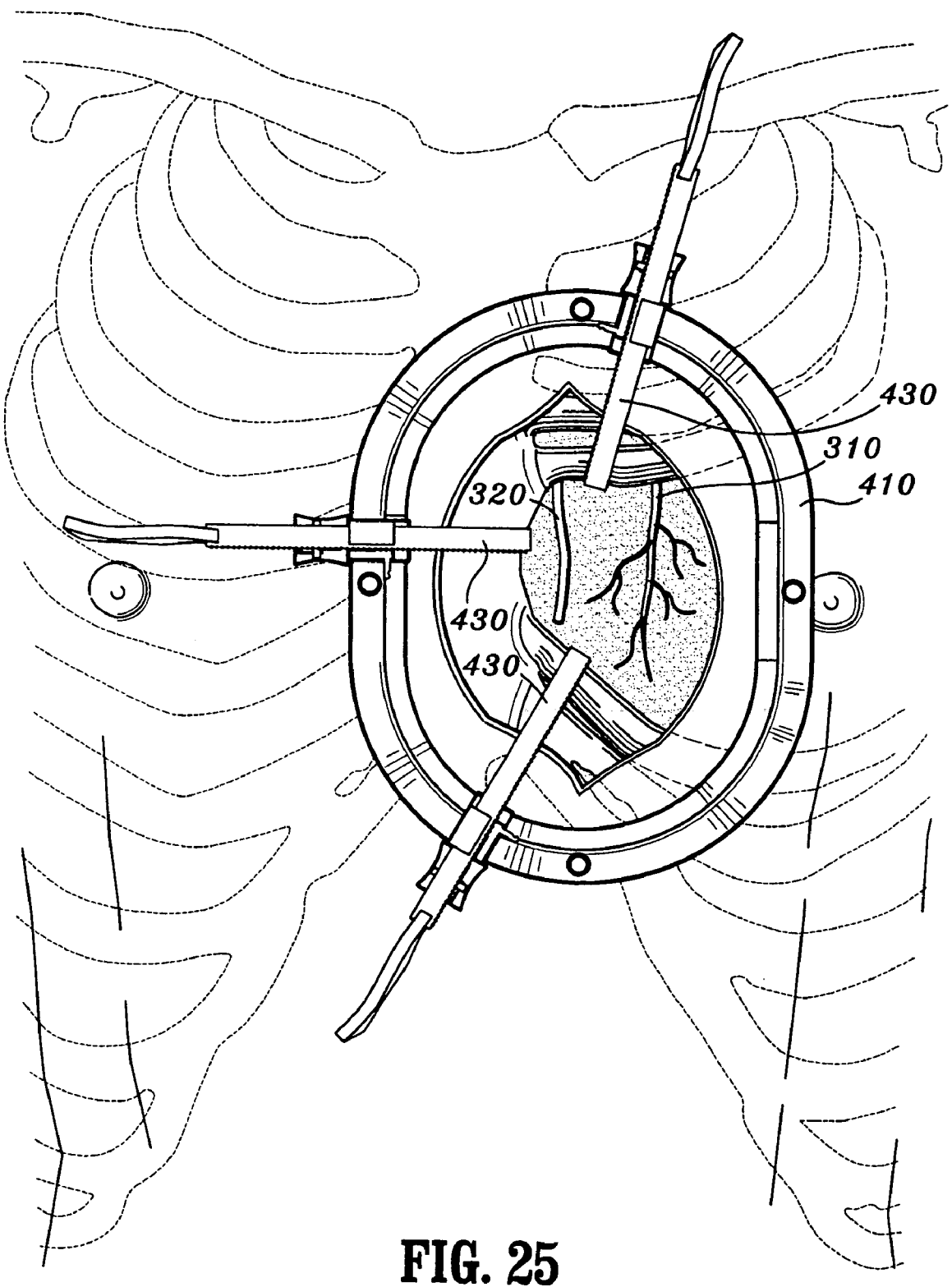
FIG. 25 is a view showing an operating "window" with the patient's heart exposed.

To gain access to the heart, after an incision is made, a surgical retractor assembly may be used to separate the ribs at the site of the incision as shown in FIG. 25. Specifically, a base 410 is placed on the chest of the patient with the central opening defined by the base being positioned over the operative site. Retractor assemblies 430 are mounted to the base 410 at various locations. Each retractor assembly 430 includes a blade having a hook to engage either a rib or the sternum therewith. The retractor assemblies are mounted and used to retract ribs until a sufficiently large opening in the chest cavity is defined to provide direct access to the heart. For example, the sternum and the fourth and fifth ribs can be split apart to create a window. Other configurations of spreading the ribs and/or selectively cutting individual ribs away from the sternum may also be utilized for a particular procedure.

Once the desired access to the heart is achieved, the graft vessel, e.g., the saphenous vein 320 is dissected and harvested from the leg, and a free end of the vessel is exposed. The occluded coronary artery, e.g., the LAD 310, is then prepared for receiving the saphenous vein 320 graft. The heart is positioned in the desired orientation either by traction sutures passing through the pericardium or by manipulation with heart manipulation instruments which are held by the surgical personnel or clamped in a fixed orientation to a base such as the retractor assembly base. Blood flow through the aorta 310 can be restricted by cardiopulmonary bypass and pericardial cooling. Alternatively, a dampening instrument may be applied directly on the aorta 310 to restrict blood flow and reduce movement of the heart near the aorta 310.

Alternatively, the present disclosure also provides for a novel method for creating the vascular anastomosis without restricting the blood flow through the luminal structure 310 via a dampening instrument, e.g., cross clamp or partial occluding clamp, as described above. More particularly, two particular clamping techniques are widely known and used. One clamping technique involves fully cross clamping the luminal structure 310 while the heart is stopped to sew the distal anastomosis. The heart is then restarted and the proximal anastomosis is sewn utilizing a partial occluding clamp. This technique is described in The Manual of Cardiac Surgery Second Edition by Harlan, Starr and Harwin and describes in particular left-sided graft. The other technique involves fully cross clamping the aorta while sewing the proximal and distal anastomosis.

Other commonly known techniques involve performing coronary artery bypass grafting without the use of cardiopulmonary bypass. More particularly, this technique involves utilizing either a mechanical and/or vacuum-assisted instruments for distal or proximal anastomosis stabilization, e.g., the Precision-Op™ instrument jointly owned by United States Surgical a division of the Tyco HealthCare Group and Heartport, Inc. These techniques are also described in The Manual of Cardiac Surgery Second Edition.

In contrast, the present disclosure also relates to a novel method for creating a vascular anastomosis without the utilization of any of the aforementioned dampening instruments. The method is shown in the schematic illustrations of FIGS. 27-30. More particularly, the present disclosure relates to a method for creating a vascular anastomosis including the steps of: creating an aortotomy in the first luminal structure, e.g., aorta 310; covering the aortotomy to stop blood flow through the aortotomy; inserting an anastomotic device having a second luminal structure, e.g., vein 320, associated therewith into the aortotomy; and actuating the anastomotic device to create an anastomosis between the first and second luminal structures.

It is envisioned that the user's finger, a surgical instrument or, perhaps, another object may be employed to cover the aortotomy to stop the blood flow. Moreover, the. anastomosis can be formed utilizing one of the embodiments described and/or referenced herein. The aortotomy may be made in the first luminal structure 310 with a scalpel, trocar, punching device and/or any other instrument known in the art. For example, one such device known as an aortic punch may be employed for use in creating the aortotomy and is shown in FIGS. 31-32B.

Aortic punch 800 includes left and right housings 810a and 810b, respectively, which, when mechanically engaged form a complete cavity 813 for housing the internal working components of the aortic punch 800 which are described in further detail below. It is envisioned that the two housings 810a and 810b are engaged by way of mechanical interfaces 840 which are positioned at various locations along each housing 810a, 810b. For example, housing 810a may include a first mechanical interface, e.g., a slot 840a, which engages a corresponding detent or tab 840b on housing 810b. It is envisioned that numerous mechanical interfaces may be employed to join the two housing halves 810a, 810b either permanently for use with a disposable unit or selectively for use with a reusable instrument. Once assembled, the two proximal ends of the housings 810a, 810b form a mutual flange 814 which biases each plunger 812, 822 during activation thereof.

Figure 31:
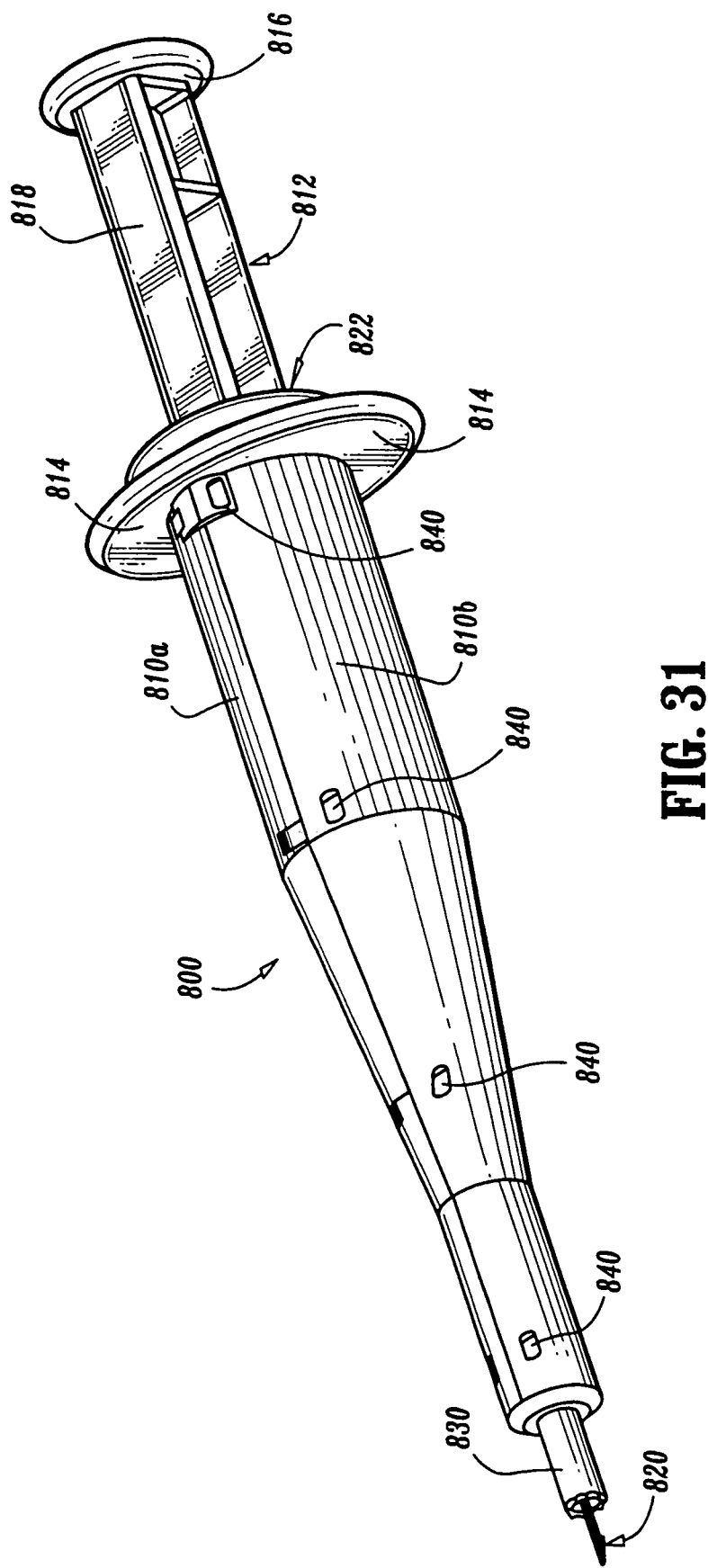
FIG. 31 is a perspective view of an aortic punch for creating an aortotomy in an aortic vessel according to the present disclosure.

As best illustrated in FIG. 31, which depicts the assembled instrument, aortic punch 800 includes two plunger-like actuators, 812 and 822, respectively, a cutting assembly 830 and a piercing needle 820. The two plungers 812 and 822, respectively, are independently operable by the user and move the cutting assembly 830 and needle 820 relative to one another to create the aortotomy in an aortic wall, e.g., luminal structure 310.

Figure 32A:
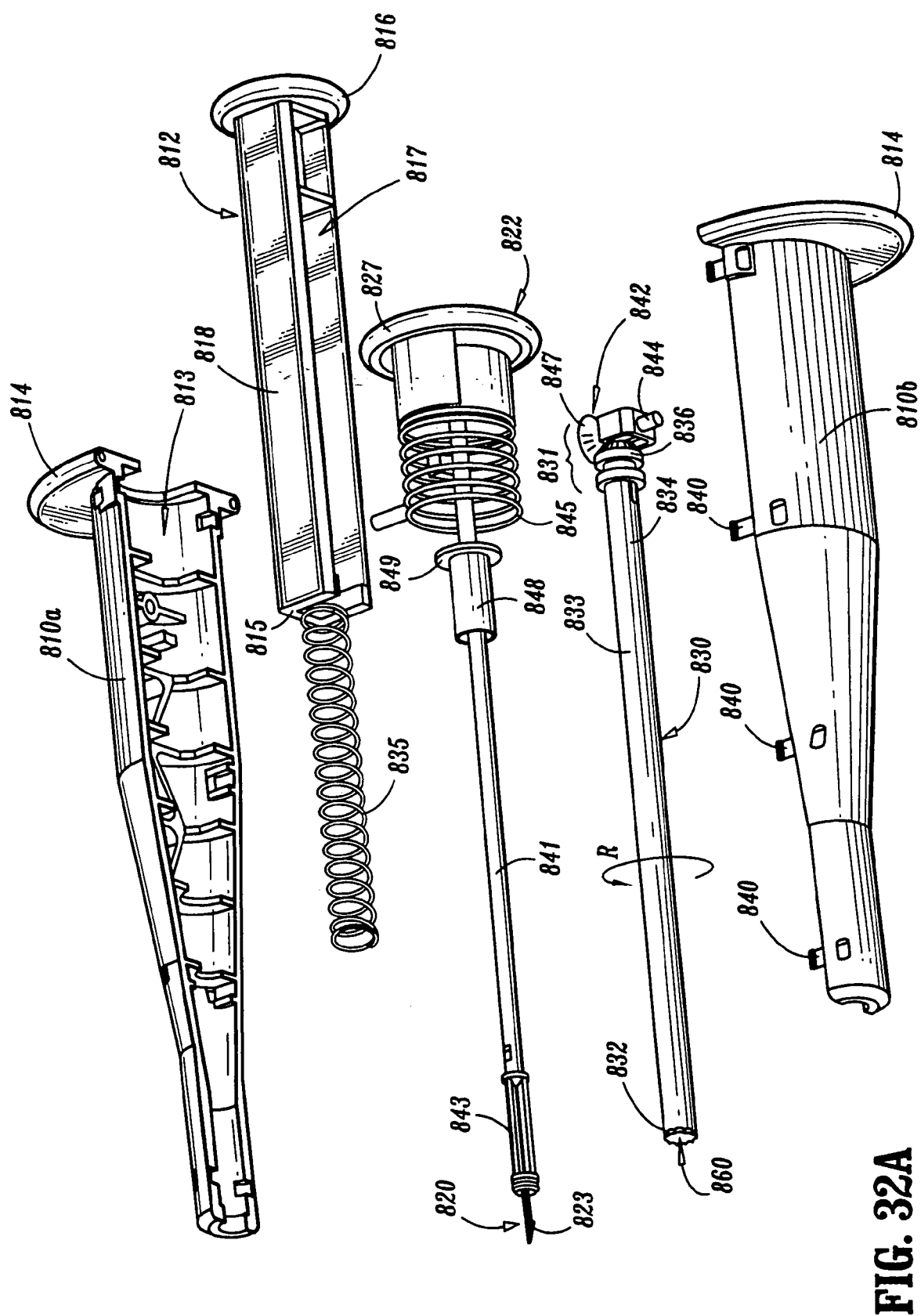
FIG. 32A is a right, perspective view with parts separated of the aortic punch of FIG. 31.
Figure 32B:
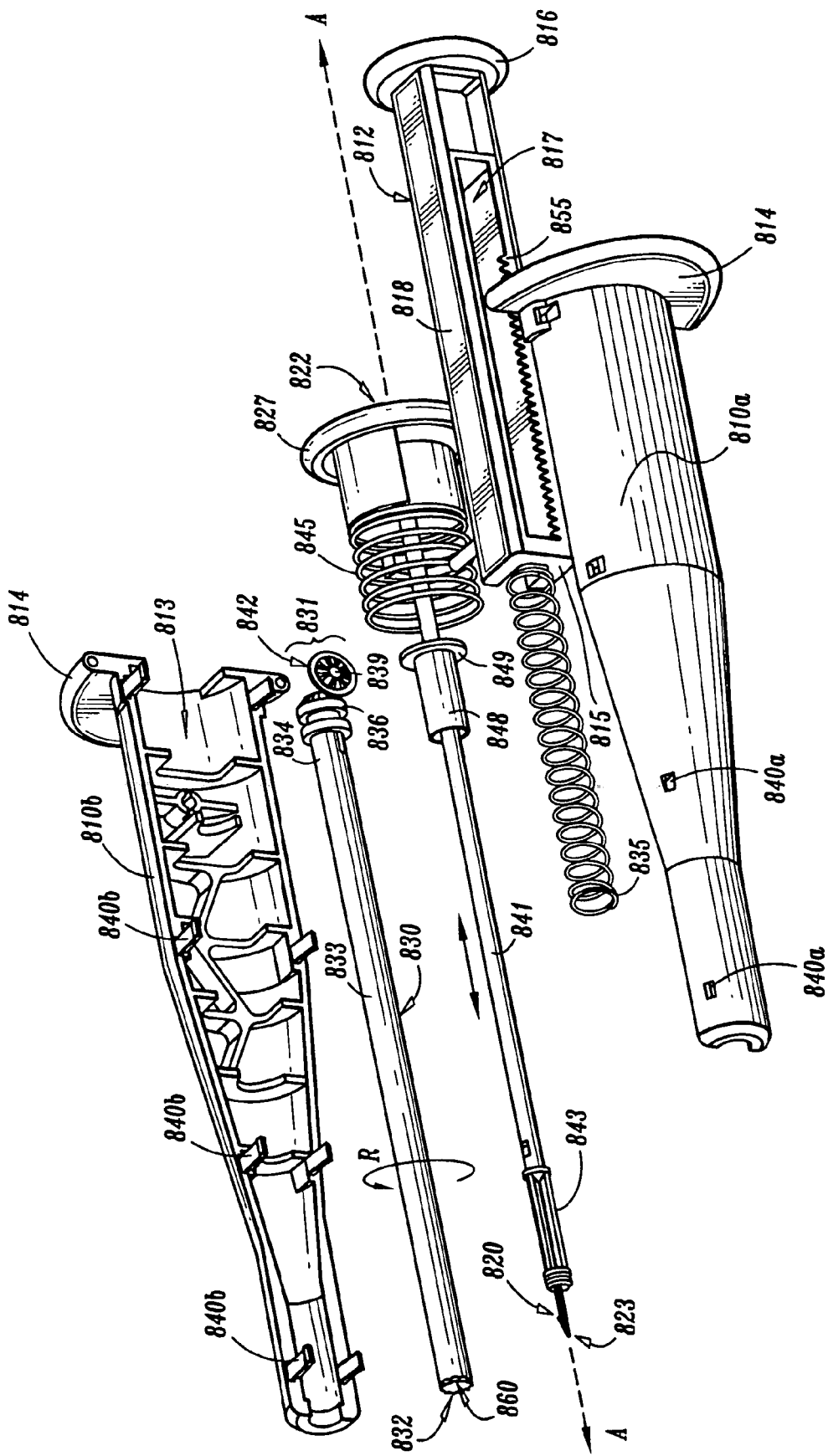
FIG. 32B is a left, perspective view with parts separated of the aortic punch of FIG. 31.

More particularly and as best illustrated in FIGS. 32A and 32B, distal movement of plunger 822 relative to flange 814a, 814b by the user exposes the needle 820 along axis "A" and, when inserted by the user, will pierce the aortic wall 310. A return spring 845 is preferably associated with the plunger 822 such that distal movement of the needle 820 along axis "A" relative to flange 814 biases the spring 845 against flange 814. The plunger 822 also includes an elongated sleeve 841 having a spline 843 at the distal end and a proximal end (not shown) which affixes to the plunger 822. It is envisioned that spline 843 facilitates rotational movement of the cutting assembly 830 relative to the needle 820 during movement of plunger 812 as described below.

Plunger 822 also includes a flange-like proximal end 827, which permits facile activation of the plunger 822 by the user. A cap 848 is affixed to the sleeve 841 and includes a skirt or shoulder portion 849 which biases spring 835 when the plunger 812 is activated as explained in more detail below with respect to the operation of the punch 800.

Needle 820 preferably includes a barb 823 which is dimensioned to catch the side of the aortic wall 310 upon return of spring 845 such that the needle 820 remains in tension against the aortic wall 310. The purpose of maintaining the barb 823 in tension against the aortic wall 310 is described in more detail below with respect to the operation of the punch 800. It is envisioned that other mechanisms or methods may be employed to hold the needle 820 in tension against the aortic wall 310, e.g., vacuum, hydraulic, magnetic, etc.

As mentioned above, plunger 812 actuates the cutting assembly 830, which creates the aortotomy in the aortic wall 310. Plunger 812 includes an elongated body 818 having a distal end 815 which mounts a return spring 835 and a flange-like proximal end 816 which is dimensioned to permit facile activation of the plunger 812 by the user. As best seen in FIG. 32B, elongated body 818 defines a cavity 817 therein which houses an elongated rack 855 which meshes with a corresponding pinion gear assembly 831 to convert linear movement of the plunger along axis "A" to rotational movement of the cutting assembly 830. Cutting assembly 830 also includes a circular knife tube 833 having a serrated tip 832 at the distal end thereof and the gear assembly 831 engaged at the proximal end 834 thereof. Other configurations of the circular knife 833 are also contemplated, e.g., non-serrated tips and/or angled/beveled tips. The gear assembly 831 includes a pinion gear 842 which is positioned transversally to axis "A" which has a plurality of teeth 839 (FIG. 32B) on one side thereof which mesh and engage the rack 855 and a beveled gear 847 (FIG. 32A) on the opposite side thereof which meshes and engages gear 836 disposed at the proximal end 834 of the cutting tube 833. As can be appreciate, movement of the pinion gear 842 along rack 855 rotates gear 836 which causes knife tube 833 to rotate.

During assembly, the knife tube 833 is fed through plunger body 818, through return spring 835, through plunger 822, through cap 848 and atop sleeve 841 such that the serrated tip 832 of the knife tube 833 encompasses the spline 843 and needle 820. The proximal end 834 of knife tube 830 and the gear assembly 831 are positioned within cavity 817 such that the gear assembly 831 engages rack 855 (See FIG. 32A. A positioning post 844 may be employed to ensure proper engagement of gear assembly 831 the rack 855. The return spring 835 is positioned between shoulder 849 of spring cap 848 and the distal end 815 of plunger 812 such that forward linear movement of plunger 812 will bias spring 835 against shoulder 849.

As can be appreciated, linear movement of the plunger 812 along axis "A" moves the rack 855 relative to the flange 814 which, in turn, rotates pinion gear 842 and, therefore, cutting assembly 830 in the direction of arrow "R" about needle 820. As mentioned above this biases spring 835 against shoulder 849 such that a release of the pressure on plunger 812 will return plunger 812 to its initial, pre-activated position. It is contemplated that a release of the pressure on plunger 812 may also reverse the rotation of knife tube 830 depending upon a particular purpose. Alternatively, it is also envisioned that a clutch, neutral gear or other mechanism (not shown) may be employed to limit the rotation of knife tube 830 in a single direction depending upon a particular purpose.

An aortotomy is created in the luminal structure 310 in the following manner: The instrument is held in the user hand in a syringe-like manner. Plunger 822 is activated, i.e., depressed, which exposes the barb 823 of needle 820 from the interior of knife tube 830 along axis "A". The user then pierces the tissue 310 with the exposed needle 820 and barb 823. Plunger 822 is then released and the return spring 845 provides tension on the barb 823 to retain the needle 820 in the tissue 310 against serrated tip 832. Plunger 812 is then depressed which moves the rack 855 relative to the flange 814 causing gear assembly 831 to rotate in the manner described above. As the user depresses the plunger 812 distally along axis "A", the circular knife tube 833 rotates the serrated tip 832 about needle 820 to cut the tissue 310. Once the tissue is cored from the surrounding tissue 310, the barb 823 loses tension against the aortic wall 310 and the return spring 845 retracts the needle 820 and the tissue core into a cavity 860 in the circular knife tube 833. The user then releases the plunger 812 to return the punch 800 to the pre-activated configuration for re-use. It is contemplated that the punch 800 can be equipped with a lock-out mechanism (not shown) which prevents the punch 800 from being re-used.

Turning now in detail to the operation of the surgical instrument 10 and in particular, the operation of the SULU 100 as detailed in FIGS. 17-24, once the saphenous vein 320 has been harvested, the user inserts the free end 322 into opening 133 of the SULU and pull via a surgical hook or graspers the free end 322 towards the distal end of the SULU 100. The user then everts the saphenous vein 320 over the anvils 118a, 118b of the SULU 100 such that the free end 322 of the saphenous vein 320 is retained by end 269 of the surgical fasteners 260. Everting of the saphenous vein 320 may be achieved by any suitable known instruments and/or techniques such as by using graspers.

Figure 18:
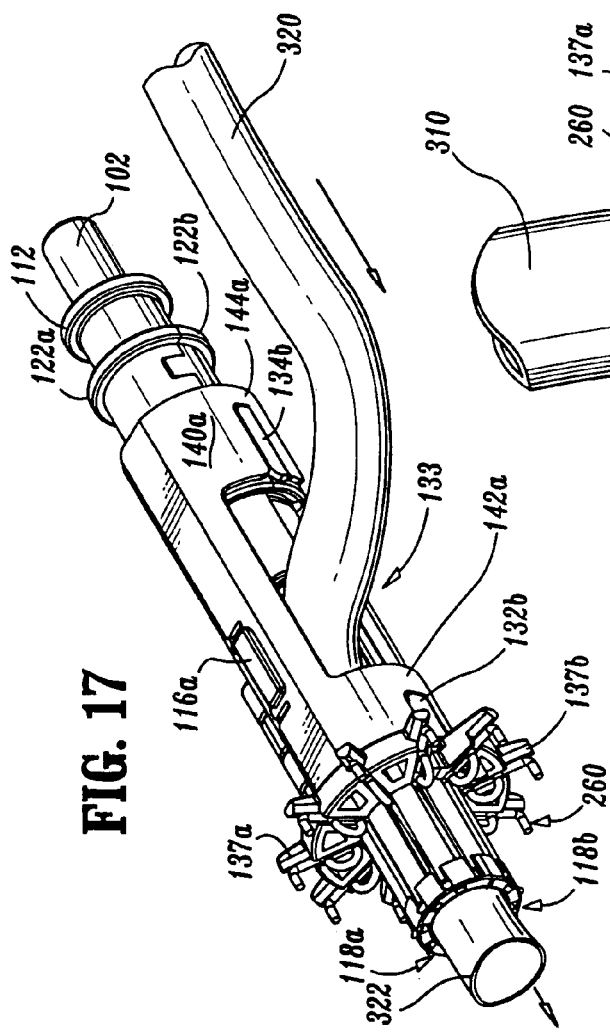
FIG. 18 is perspective of the SULU with an end of the first vessel everted over a distal end of the disposable unit being inserted into an incision in a second vessel.

The remaining portion of the saphenous vein 320 is preferably positioned away from the instrument 10 to facilitate insertion of the saphenous vein 320 into the aorta 310 as shown in FIG. 18. The user then inserts the end of the SULU 100 into an incision 312 in the aorta such that the distal end 269 of each of the plurality of fasteners 260 and the everted end portions 322 of the saphenous vein 320 are sufficiently inserted into and through incision 312 (FIGS. 19 and 20). As seen best in the enlarged view of FIG. 20, the support leg 262, convexity 263 and prong 267 of each surgical fastener 260 remains outside incision 312. The instrument is now preset for firing.

FIGS. 21-22 show the firing sequence of instrument 10, i.e., when the handle 12 is depressed by the user. As best shown in FIGS. 21 and 21A, as handle 12 is depressed downwardly in the direction of reference arrow "A", lever 16 simultaneously imparts movement to both handle lock 40 and cam 60. More particularly, downward movement of handle 12 causes flanges 14a and 14b of lever 16 to urge flanges 42a and 42b of handle lock 40 distally against spring 45 in the direction of reference arrow "B" (FIG. 21). At the same time, handle 12 causes recess 17 of lever 16 to bias nub 66 which, in turn, causes cam 60 to deflect downwardly and proximally as best seen in FIG. 21A. Preferably, recess 17 in lever 16 is dimensioned to control the specific movement of nub 66 within recess 17, which, in turn, controls the overall movement of cam 60. Downward and proximal movement of cam 60 causes cam followers 51 a and 51b to move within the first cam stages 64a and 62a of slots 64 and 62, respectively, which, in turn, moves the first retractor 80 and protective cover 95 proximally in the direction of reference arrow B .

As seen best in FIG. 21, as retractor 80 moves proximally as a result of the movement of cam followers 51a and 51b within slots 64 and 62, slot 85 moves proximally until it abuts pin 54. Preferably, when slot 85 abuts pin 54, cam 60 is forced more downwardly about pin 54 such that cam followers 51a and 51b move more proximally to engage the second stages 64b and 62b of the cam slots 64 and 62, respectively.

As mentioned above, the first retractor 80 retracts the first retracting sleeve 110 (FIG. 21) which, in turn, causes surgical fasteners 260 to deform as shown in FIGS. 21B and 21D. More particularly and as best shown in FIG. 21B, proximal movement of the first retractor 80 causes both the first retracting sleeve 110 and the second retracting sleeve 120 to move proximally relative to biasing post 102 until biasing post 102 abuts the end 69 of elongated stop 65. As a result, anvils 118a and 118b deform the distal ends 269 of surgical fasteners 260 upwardly and proximally towards braces 137a and 137b, respectively, i.e., arc-like distal ends 184a and 184b cause surgical fasteners 260 to deform upwardly and proximally upon retraction of the first retracting sleeve 110. At the same time, the aorta 310 is forced slightly proximally and extending prongs 267 penetrate to hold the aorta 310 in position as best seen in FIG. 22A.

It is anticipated that the radially offset orientation of the opposite ends 186a, 186b and 184a, 184b of the support channels 119a and 119b, respectively will cause the opposite ends 267 and 269 of the surgical fasteners 260 to deform at an angle ∀ relative to one another as best shown in FIG. 21D. This allows end 269 to deform proximal to braces 137a and 137b. Preferably, braces 137a and 137b have a tapered cross section to deform end 269 of surgical fastener 260 radially from end 267 during deformation.

FIG. 21C shows the resulting position of the spacer 104 of the biasing post 102 after the first retractor 80 retracts the first and second retracting sleeves 110 and 120, respectively. More particularly, spacer 104 frictionally locks the first retracting sleeve 110 relative to the second retracting sleeve 120 and prevents the first retracting sleeve 110 from recoiling after firing.

FIG. 21E shows the proximal movement of the locking sleeve 140a as a result of the movement of the first retracting sleeve 110. More particularly, when the first retracting sleeve 110 is retracted proximally, locking tab 116a retracts within slot 131 a of support 130a and biases locking sleeve 140a in a proximal direction as well as seen by reference arrow "C". Proximal movement of the locking sleeve 140a relative to support 130a disengages flanges 142a and 144a from shoulders 132b and 134b, respectively, of support 130b which, in turn, unlocks supports 130a and 130b from one another thus permitting pivotal movement of the support members 130a, 130b as best seen in FIGS. 21E and 23.

Continued downward movement of handle 12 results in both proximal movement of the second retractor 50 and engagement of the handle lock 40 with the handle 12. More particularly and as best illustrated in FIG. 22, as the user continues to move the handle 12 in a downward direction, flanges 14a and 14b clear corresponding flanges 42a and 42b and spring 45 biases handle lock 40 proximally in the direction of reference arrow "D" to lock the handle 12 in position. Simultaneously, cam 60 is rotated about pin 54 to a point where the second stages 64a and 62a of the cam slots 64 and 62 effect the movement of the cam followers 51a and 51b. More particularly, as cam 60 is forced downwardly, the second stage 62a of cam slot 62 moves cam follower 51b proximally which, in turn, moves the second retractor 50 proximally. The second stage 64a of cam slot 64 is generally vertically oriented and, as a result, cam follower 51a moves vertically upon continued downward movement of handle 12. Slot 57 of retractor 50 allows the second retractor 50 to slide proximally relative to cam follower 51a.

As mentioned above, second retractor 50 moves the key-like end 53 of the second retracting sleeve 120 within carriage 86 relative to the first retracting sleeve 110 as illustrated by reference arrow "E" of FIG. 22A. Proximal movement of the second retracting sleeve 120 retracts the prongs 127a and 127b of fingers 124a, 124b, respectively, which releases the surgical fasteners 260 as illustrated by reference arrow "E" of FIG. 22B.

It is envisioned that the surgical instrument 10 and/or the SULU 100 may need to be manipulated to assure consistent and tactful release of the surgical fasteners 260 from the SULU. For example, it is contemplated that after and/or simultaneously with activation of the handle 12, the presently disclosed methods described herein may include the step of manipulating the surgical instrument 10 or SULU 100 relative to the surgical fasteners 260 to facilitate release thereof, e.g., rotational or off-axis manipulation relative to axis "A" (See FIG. 5), vertical manipulation, horizontal manipulation, pivotal manipulation and/or any simultaneous or sequential combination of these aforedescribed manipulative movements.

Further, it is contemplated that the surgical instrument 10 or the SULU 100 may be manufactured to include an additional activator, lever, handle, pivot element, linkage or the like (not shown) which upon activation thereof will manipulate the surgical instrument 10 and/or SULU 100 relative to the surgical fasteners 260 in one of the manners described above to facilitate consistent and tactful release of the surgical fasteners 260.

As mentioned above, after sleeve 110 is retracted, locking sleeve 140a moves proximally to allow the two supports 130a and 130b to pivot away from one another as shown in FIG. 23 to permit the removal of the saphenous vein 320 from within the SULU thereby completing the vascular anastomosis as shown in FIG. 24.

Figure 26A:
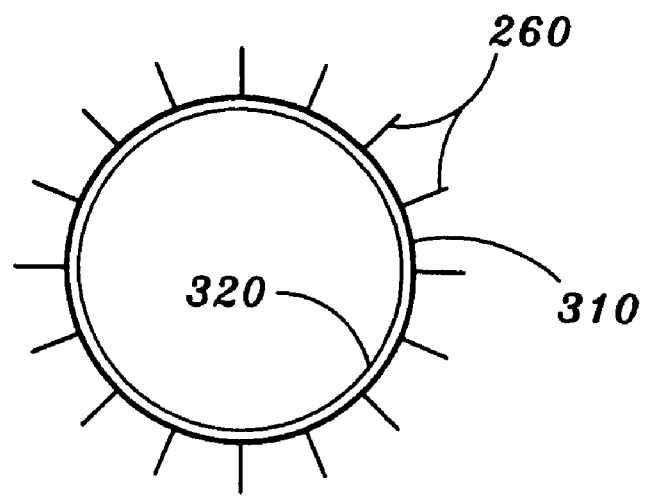
FIG. 26A is a view showing the surgical fastener staple pattern of the instrument described with respect to FIGS. 1-26.
Figure 26B:
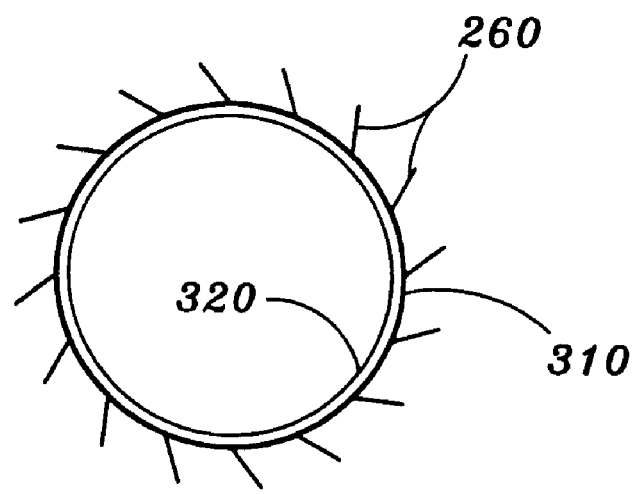
FIG. 26B. is a view showing one possible alternative surgical fastener staple pattern.
Figure 28:
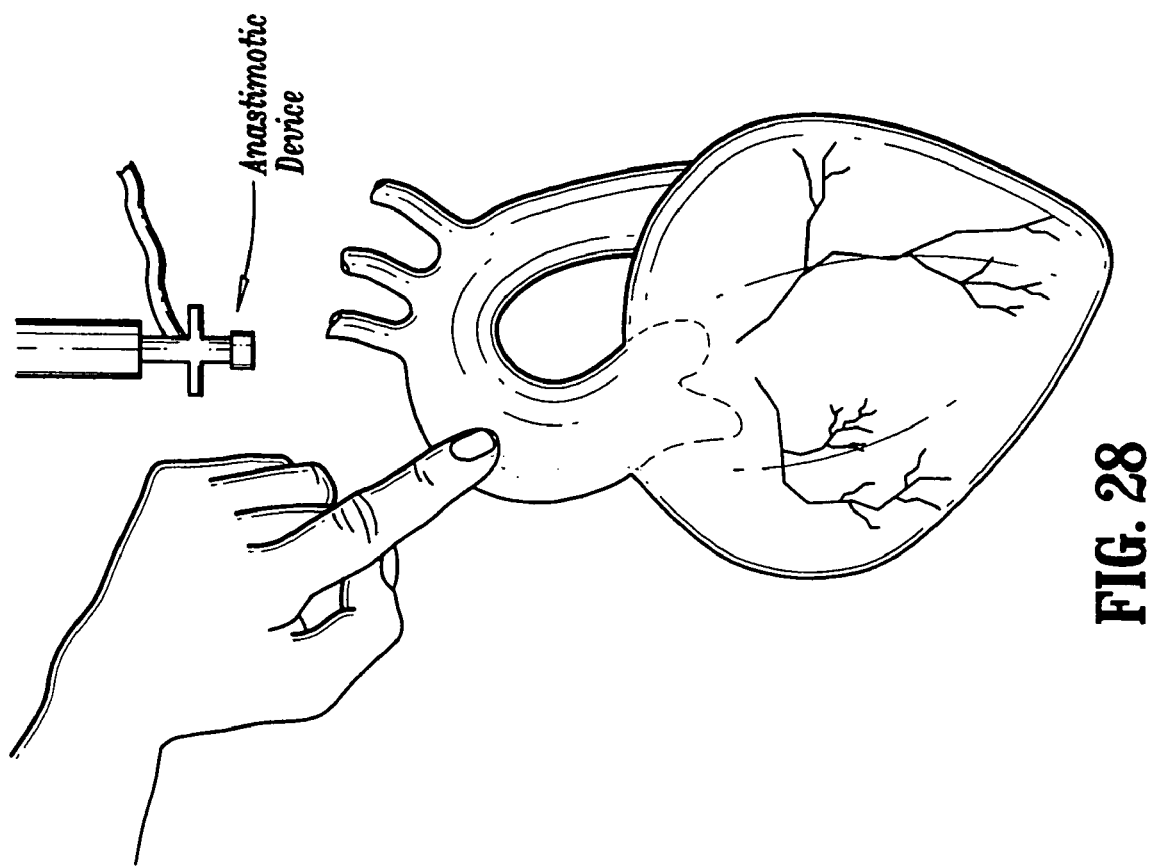
FIGS. 27-30 are schematic illustrations depicting a method of creating an anastomosis according to the present disclosure.
Figure 27:
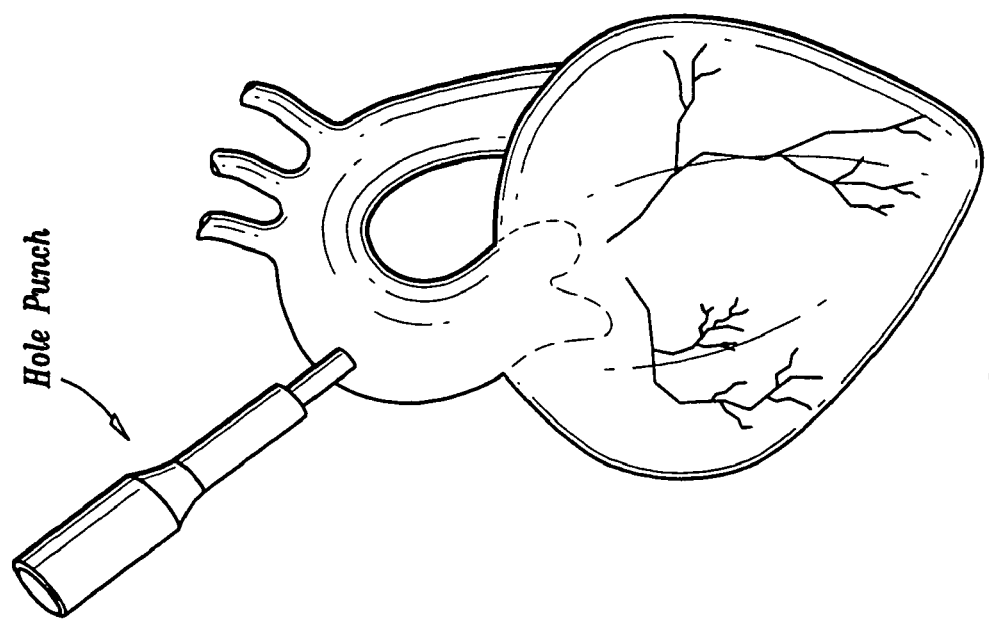
Figure 30:
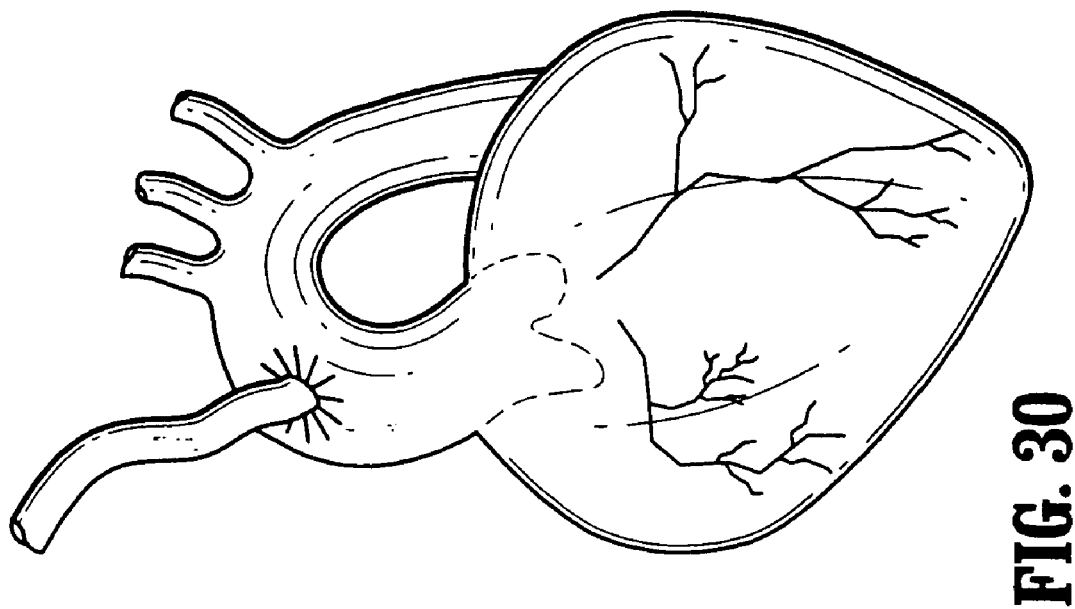
Figure 29:
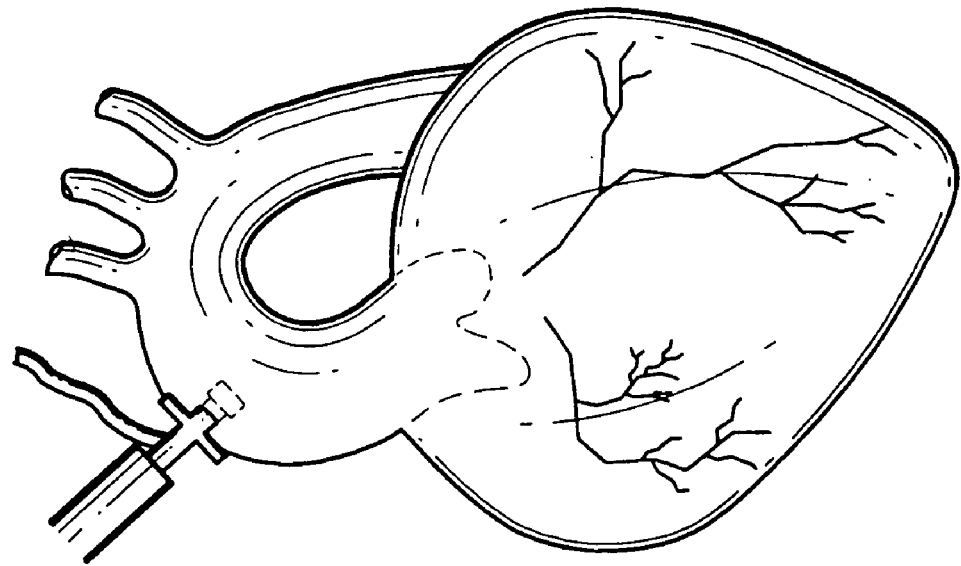

FIG. 26A shows a schematic diagram of the surgical fastener staple pattern, which is formed upon actuation of the instrument, described above with respect to FIGS. 1-26. More particularly, the surgical fasteners are supported by the fastener support braces 137a, 137b in a normal manner relative to a longitudinal axis "A" (FIG. 5) extending through the SULU. It is envisioned that other surgical fastener staple patterns, e.g., spiral, tangential or angular relative to axis "A", may be utilized to achieve hemostasis between vessels, FIG. 26B. For example, it is contemplated that arranging the surgical fasteners 260 in one of the aforedescribed patterns may enable more surgical fasteners 260 to be employed within the same spatial considerations, which may achieve a more consistent and/or more reliable hemostasis between vessels.

It will be understood that various modifications may be made to the embodiment shown herein. For example, the instrument may be sized to perform an anastomosis for other vessels and luminal tissue. Moreover, although the various internal components of the instrument 10 are shown engaged by particular mechanical interfaces it is envisioned that other types of mechanical interfaces can be employed to achieve the same or similar purpose, e.g., snap-fit, tongue and groove, press fit, etc. Therefore, the above description should not be construed as limiting, but merely as exemplifications of preferred embodiment. Those skilled in the art will envision other modifications within the scope and spirit of the claims appended hereto.

What is claimed is:

1. A surgical instrument for anastomosis of first and second blood vessels, comprising:
    a housing having distal and proximal ends and a horizontal axis and an actuator disposed therebetween, the actuator including:
    a handle which is moveable from a first position relative to the housing to at least one subsequent position in closer proximity to the housing; and
    a link assembly mechanically engaged with the handle and being moveable through a firing stroke in response to the movement of the handle from the first position to the at least one subsequent position, the link assembly includes a three bar link assembly at least three links linked together;
    a disposable loading unit releasably attached to the distal end of the housing in mechanical cooperation with the actuator, the disposable loading unit including a plurality of surgical fasteners which are deformed and released upon movement of the actuator through the firing stroke,
    wherein the firing stroke of the handle and the link assembly includes:
    a first stage wherein:
        the links are each respectively disposed at a first angle relative to the horizontal axis disposed through the housing;
        the handle is in the first position relative to the housing, and
        the plurality of surgical fasteners are maintained within the disposable loading unit;
    an intermediate stage wherein:
        the links move through a range of motion to a fully-extended and substantially parallel position relative to the horizontal axis,
        the handle moves to a position in closer proximity to the housing, and
        the plurality of surgical fasteners deform within the disposable loading unit; and
    a third, post-firing stage wherein:
        the links each move through a range of motion to a respective angle relative to the horizontal axis,
        the handle moves to a position in closest proximity to the housing, and
        the plurality of surgical fasteners release from engagement within the disposable loading unit.

2. A surgical instrument according to claim 1 wherein the link assembly biases a spring through the first and intermediate stages of the firing stroke.

3. A surgical instrument according to claim 2 wherein the biasing of the spring during the movement of link assembly through the first and intermediate stages mechanically facilitates movement of the link assembly from the intermediate to third stages to release the surgical fasteners.

4. A surgical instrument according to claim 2 wherein the link assembly unbiases the spring through the third stage of the firing stroke.

5. A surgical instrument according to claim 1 further comprising a second handle to facilitate activation of the actuator.

6. A surgical instrument according to claim 1 wherein the handle includes a tab which locks the handle in proximate relation to the housing after completion of the firing stroke.

7. A surgical instrument according to claim 1, wherein the links are in a substantially linear arrangement in the intermediate stage.

8. A surgical instrument according to claim 1, wherein the arrangement of the link assembly in the third, post-firing stage locks the handle.

9. A surgical instrument for deploying surgical fasteners, comprising:
    a housing having distal and proximal ends and a horizontal axis defined therethrough and between the distal and proximal ends;
    a handle which is moveable in a stroke from a first position relative to the housing to at least one subsequent position in closer proximity to the housing;
    a link assembly mechanically engaged with the handle and being moveable through the stroke in response to the movement of the handle from the first position to at least one subsequent position, the link assembly including at least three links linked together;
    a loading unit releasably attached at the distal end of the housing and including a plurality of surgical fasteners which are deformed and released upon movement of the actuator through the stroke,
    wherein the stroke of the handle and the link assembly includes a first stage wherein the links each are positioned at a respective angle relative to the horizontal axis and, a second stage wherein the links move to a fully-extended and substantially parallel position relative to the horizontal axis, and a third stage wherein the links each are positioned at a respective angle relative to the horizontal axis and the handle is in a position in closest proximity to the housing.

10. The surgical instrument of claim 9, wherein the surgical fasteners are deformed in the second stage.

11. The surgical instrument of claim 10, wherein the surgical fasteners are released in the third stage.

12. The surgical instrument of claim 9, further comprising a handle lock.

* * * * *